(12) United States Patent
Sonderegger et al.

(10) Patent No.: US 10,112,006 B2
(45) Date of Patent: Oct. 30, 2018

(54) NEEDLE SHIELDING ASSEMBLIES AND INFUSION DEVICES FOR USE THEREWITH

(71) Applicant: Becton, Dickinson and Company, Franklin Lakes, NJ (US)

(72) Inventors: Ralph Sonderegger, Farmington, UT (US); Victor Politis, Framingham, MA (US); Stephen Richards, Carrywood, ID (US); Gary Searle, Norfolk, MA (US); Eric Bené, Lynn, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 60 days.

(21) Appl. No.: 15/445,766

(22) Filed: Feb. 28, 2017

(65) Prior Publication Data

US 2017/0224914 A1    Aug. 10, 2017

Related U.S. Application Data

(63) Continuation of application No. 14/362,102, filed as application No. PCT/US2012/068604 on Dec. 7, 2012, now Pat. No. 9,889,255.

(Continued)

(51) Int. Cl.
*A61M 31/00* (2006.01)
*A61M 5/158* (2006.01)
(Continued)

(52) U.S. Cl.
CPC ............ *A61M 5/158* (2013.01); *A61M 5/142* (2013.01); *A61M 5/326* (2013.01);
(Continued)

(58) Field of Classification Search
CPC .. A61M 2005/1581; A61M 2005/1585; A61M 2005/3249; A61M 5/158;
(Continued)

(56) References Cited

U.S. PATENT DOCUMENTS

| 2,748,769 A | 6/1956 | Huber |
| 2,928,633 A | 6/1957 | Holmes et al. |

(Continued)

FOREIGN PATENT DOCUMENTS

| EP | 2598188 A1 | 1/1982 |
| EP | 1704889 A1 | 9/2006 |

(Continued)

*Primary Examiner* — Rebecca E Eisenberg
(74) *Attorney, Agent, or Firm* — Dickinson Wright PLLC

(57) ABSTRACT

A needle assembly includes a needle and a needle shield device. The needle shield device includes an inner shield connectable to at least one a base and a fluid connector connectable to the base, and an outer shield fixedly connected to the opposing end the needle and displaceable relative to the inner shield between a first position, in which the sharpened end of the needle is exposed outside the inner shield, and a second position, in which the sharpened end of the needle is shielded by the inner shield. Interaction between portions of the inner and outer shields during or after proximal displacement of the outer shield from the first position to the second position automatically releases or permits release of the inner shield from connection to the at least one of the base and the fluid connector.

6 Claims, 47 Drawing Sheets

Related U.S. Application Data

(60) Provisional application No. 61/568,074, filed on Dec. 7, 2011, provisional application No. 61/692,985, filed on Aug. 24, 2012.

(51) Int. Cl.
*A61M 5/32* (2006.01)
*A61M 5/142* (2006.01)

(52) U.S. Cl.
CPC ........ *A61M 5/3216* (2013.01); *A61M 5/3243* (2013.01); *A61M 5/3275* (2013.01); *A61M 2005/1581* (2013.01); *A61M 2005/1585* (2013.01)

(58) Field of Classification Search
CPC .. A61M 5/3216; A61M 5/3243; A61M 5/326; A61M 5/3275
See application file for complete search history.

(56) References Cited

U.S. PATENT DOCUMENTS

| | | |
|---|---|---|
| 3,658,061 A | 4/1972 | Hall |
| 3,782,671 A | 1/1974 | Igwe |
| 4,123,091 A | 10/1978 | Cosentino et al. |
| 4,219,912 A | 9/1980 | Adams |
| 4,311,137 A | 1/1982 | Gerard |
| 4,362,156 A | 12/1982 | Feller, Jr. et al. |
| 4,664,259 A | 5/1987 | Landis |
| 4,752,292 A | 6/1988 | Lopez et al. |
| 4,781,680 A | 11/1988 | Redmond et al. |
| 4,834,718 A | 5/1989 | McDonald |
| 4,894,055 A | 1/1990 | Sudnak |
| 4,982,842 A | 1/1991 | Hollister |
| 5,017,189 A | 5/1991 | Boumendil |
| 5,137,529 A | 8/1992 | Watson et al. |
| 5,188,611 A | 2/1993 | Orgain |
| 5,257,980 A | 11/1993 | Van Antwerp et al. |
| 5,300,034 A | 4/1994 | Behnke et al. |
| 5,350,363 A | 9/1994 | Goode et al. |
| 5,360,408 A | 11/1994 | Vaillancourt |
| 5,368,801 A | 11/1994 | Vaillancourt |
| 5,472,138 A | 12/1995 | Ingram |
| 5,490,841 A | 2/1996 | Landis |
| 5,522,803 A | 6/1996 | Teissen-Simony |
| 5,545,143 A | 8/1996 | Fischell |
| 5,562,631 A | 10/1996 | Bogert |
| 5,575,769 A | 11/1996 | Vaillancourt |
| 5,591,138 A | 1/1997 | Vailancourt |
| 5,688,254 A | 11/1997 | Lopez et al. |
| 5,725,503 A | 3/1998 | Arnett |
| 5,776,116 A | 7/1998 | Lopez et al. |
| 5,797,897 A | 8/1998 | Jepson et al. |
| 5,810,792 A | 9/1998 | Fangrow et al. |
| 5,817,074 A | 10/1998 | Racz |
| 5,848,990 A | 12/1998 | Cirelli et al. |
| 5,851,197 A | 12/1998 | Marano et al. |
| 5,871,500 A | 2/1999 | Jepson et al. |
| 5,891,099 A | 4/1999 | Nakajima et al. |
| 5,935,109 A | 8/1999 | Donnan |
| 5,968,011 A | 10/1999 | Larsen et al. |
| 6,017,328 A | 1/2000 | Fischell et al. |
| 6,056,718 A | 5/2000 | Funderburk et al. |
| 6,093,172 A | 7/2000 | Funderburk et al. |
| 6,162,206 A | 12/2000 | Bindokas et al. |
| 6,261,272 B1 | 7/2001 | Gross et al. |
| 6,273,869 B1 | 8/2001 | Vaillancourt |
| 6,293,925 B1 | 9/2001 | Safabash et al. |
| 6,302,866 B1 | 10/2001 | Marggi |
| 6,346,095 B1 | 2/2002 | Gross et al. |
| 6,355,021 B1 | 3/2002 | Nielsen et al. |
| 6,447,498 B1 | 9/2002 | Jepson et al. |
| 6,485,473 B1 | 11/2002 | Lynn |
| 6,520,938 B1 | 2/2003 | Funderburk et al. |
| 6,605,076 B1 | 8/2003 | Jepson et al. |
| 6,607,509 B2 | 8/2003 | Bobroff et al. |
| 6,685,674 B2 | 2/2004 | Douglas et al. |
| 6,689,100 B2 | 2/2004 | Connelly et al. |
| 6,702,779 B2 | 3/2004 | Connelly et al. |
| D488,230 S | 4/2004 | Ignotz et al. |
| 6,736,797 B1 | 5/2004 | Larsen et al. |
| 6,740,063 B2 | 5/2004 | Lynn |
| 6,830,562 B2 | 12/2004 | Mogensen et al. |
| 6,840,922 B2 | 1/2005 | Nielsen et al. |
| 6,926,694 B2 | 8/2005 | Marano-Ford et al. |
| 6,949,084 B2 | 9/2005 | Marggi et al. |
| 6,972,002 B2 | 12/2005 | Thorne |
| 6,991,620 B2 | 1/2006 | Marano-Ford et al. |
| 6,997,907 B2 | 2/2006 | Safabash et al. |
| 7,022,108 B2 | 4/2006 | Marano-Ford et al. |
| 7,070,580 B2 | 7/2006 | Nielsen |
| 7,128,730 B2 | 10/2006 | Marano-Ford et al. |
| 7,129,389 B1 | 10/2006 | Watson |
| 7,147,623 B2 | 12/2006 | Mathiasen |
| 7,207,974 B2 | 4/2007 | Safabash et al. |
| 7,297,138 B2 | 11/2007 | Fangrow et al. |
| 7,300,419 B2 | 11/2007 | Fangrow et al. |
| 7,303,544 B2 | 12/2007 | Buetikofer et al. |
| 7,309,326 B2 | 12/2007 | Fangrow |
| 7,311,694 B2 | 12/2007 | Fangrow |
| 7,314,463 B2 | 1/2008 | Fangrow |
| 7,331,939 B2 | 2/2008 | Fangrow |
| 7,338,465 B2 | 3/2008 | Patton |
| 7,377,908 B2 | 5/2008 | Buetikofer et al. |
| 7,407,491 B2 | 8/2008 | Fangrow |
| 7,407,493 B2 | 8/2008 | Cane |
| D576,267 S | 9/2008 | Mogensen et al. |
| 7,481,794 B2 | 1/2009 | Jensen |
| 7,494,481 B2 | 2/2009 | Moberg et al. |
| 7,520,867 B2 | 4/2009 | Bowman et al. |
| 7,524,300 B2 | 4/2009 | Patton |
| 7,594,902 B2 | 9/2009 | Horisberger et al. |
| 7,621,395 B2 | 11/2009 | Mogensen et al. |
| 7,682,341 B2 | 3/2010 | Nakajima |
| 7,699,807 B2 | 4/2010 | Faust et al. |
| 7,699,808 B2 | 4/2010 | Marrs et al. |
| 7,704,228 B2 | 4/2010 | Patton |
| 7,727,198 B2 | 6/2010 | Nakajima |
| 7,731,691 B2 | 6/2010 | Cote et al. |
| 7,744,568 B2 | 6/2010 | Douglas et al. |
| 7,744,570 B2 | 6/2010 | Fangrow |
| 7,731,680 B2 | 7/2010 | Patton |
| 7,771,412 B2 | 8/2010 | Anderson et al. |
| 7,850,658 B2 | 12/2010 | Faust et al. |
| 7,879,010 B2 | 2/2011 | Hunn et al. |
| 7,892,216 B2 | 2/2011 | Fangrow |
| 7,931,615 B2 | 4/2011 | Fangrow |
| 7,935,090 B2 | 5/2011 | Patton |
| 7,985,199 B2 | 7/2011 | Kornerup et al. |
| 7,993,306 B2 | 8/2011 | Marrs et al. |
| 8,012,126 B2 | 9/2011 | Tipsmark et al. |
| 8,105,279 B2 | 1/2012 | Mernoe et al. |
| 8,152,769 B2 | 4/2012 | Douglas et al. |
| 8,152,771 B2 | 4/2012 | Mogensen et al. |
| 8,162,892 B2 | 4/2012 | Mogensen et al. |
| 8,172,805 B2 | 5/2012 | Mogensen et al. |
| 8,177,745 B2 | 5/2012 | Brechbuehler et al. |
| 8,216,208 B2 | 7/2012 | Patton |
| 8,221,361 B2 | 7/2012 | Patton |
| 8,221,362 B2 | 7/2012 | Patton |
| 8,221,386 B2 | 7/2012 | Patton |
| 8,226,614 B2 | 7/2012 | Turner et al. |
| 8,231,577 B2 | 7/2012 | Carter et al. |
| 8,262,627 B2 | 9/2012 | Patton |
| 8,317,759 B2 | 11/2012 | Moberg et al. |
| 8,366,683 B2 | 2/2013 | Patton |
| 8,449,504 B2 | 5/2013 | Carter et al. |
| D684,685 S | 6/2013 | Schneider et al. |
| D685,083 S | 6/2013 | Schneider et al. |
| 8,469,929 B2 | 6/2013 | Hunn et al. |
| 8,551,047 B2 | 10/2013 | Burns et al. |
| 8,628,498 B2 | 1/2014 | Safabash et al. |
| 8,657,788 B2 | 2/2014 | Fangrow |

(56) References Cited

U.S. PATENT DOCUMENTS

| | | |
|---|---|---|
| 8,771,227 B2 | 7/2014 | Connelly et al. |
| 8,777,925 B2 | 7/2014 | Patton |
| 8,790,311 B2 | 7/2014 | Gyrn |
| 8,795,309 B2 | 8/2014 | Lacy |
| 8,801,660 B2 | 8/2014 | Hunn et al. |
| 8,808,254 B2 | 8/2014 | Lynn |
| 8,814,833 B2 | 8/2014 | Farrell et al. |
| 8,827,957 B2 | 9/2014 | Searle et al. |
| 8,905,974 B2 | 12/2014 | Carter et al. |
| 8,945,057 B2 | 2/2015 | Gym et al. |
| 8,956,330 B2 | 2/2015 | Fangrow, Jr. |
| 2002/0173774 A1 | 11/2002 | Olsen |
| 2002/0177813 A1 | 11/2002 | Adams et al. |
| 2003/0018303 A1 | 1/2003 | Sharp |
| 2003/0105431 A1 | 6/2003 | Howell |
| 2003/0220610 A1 | 11/2003 | Lastovich et al. |
| 2004/0049155 A1 | 3/2004 | Schramm |
| 2004/0092893 A1 | 5/2004 | Haider et al. |
| 2004/0102740 A1 | 5/2004 | Meloul |
| 2004/0193120 A1 | 9/2004 | Ferguson et al. |
| 2005/0038378 A1 | 2/2005 | Lastovich et al. |
| 2005/0090784 A1 | 4/2005 | Nielsen et al. |
| 2005/0101932 A1 | 5/2005 | Cote et al. |
| 2005/0245895 A1 | 11/2005 | Haider et al. |
| 2007/0088271 A1 | 4/2007 | Richards |
| 2007/0191771 A1 | 8/2007 | Moyer |
| 2007/0191772 A1 | 8/2007 | Wojcik |
| 2007/0191774 A1 | 8/2007 | Carrez et al. |
| 2007/0244448 A1 | 10/2007 | Lastovich et al. |
| 2007/0276355 A1 | 11/2007 | Nielsen et al. |
| 2008/0177238 A1 | 7/2008 | Follman et al. |
| 2008/0243085 A1 | 10/2008 | DeStefano |
| 2008/0249471 A1 | 10/2008 | DeStefano et al. |
| 2008/0281297 A1 | 11/2008 | Pesach et al. |
| 2008/0287874 A1 | 11/2008 | Elmouelhi |
| 2009/0069752 A1 | 3/2009 | Raj et al. |
| 2009/0076453 A1 | 3/2009 | Mejlhede et al. |
| 2009/0082734 A1 | 3/2009 | Walters et al. |
| 2009/0143763 A1 | 6/2009 | Wyss et al. |
| 2009/0163878 A1 | 6/2009 | Moberg et al. |
| 2009/0221971 A1 | 9/2009 | Mejlhede et al. |
| 2009/0264825 A1 | 10/2009 | Cote et al. |
| 2009/0299289 A1 | 12/2009 | Karmen et al. |
| 2010/0137829 A1 | 3/2010 | Nielsen |
| 2010/0179508 A1 | 7/2010 | Mogensen et al. |
| 2011/0118672 A1 | 5/2011 | Hanson et al. |
| 2011/0130722 A1 | 6/2011 | Fangrow |
| 2011/0213340 A1 | 9/2011 | Howell et al. |
| 2011/0288482 A1 | 11/2011 | Farrell et al. |
| 2011/0313357 A1 | 12/2011 | Skutnik et al. |
| 2012/0123344 A1 | 5/2012 | Hornig et al. |
| 2012/0179106 A1 | 7/2012 | Cote et al. |
| 2012/0226242 A1 | 9/2012 | Nielsen et al. |
| 2013/0006216 A1 | 1/2013 | Taylor et al. |
| 2013/0012881 A1 | 1/2013 | Lacy |
| 2013/0023834 A1 | 1/2013 | Turner et al. |
| 2013/0245555 A1 | 9/2013 | Dirac et al. |
| 2013/0281974 A1 | 10/2013 | Kamen et al. |
| 2013/0282974 A1 | 10/2013 | Joisha |
| 2014/0039453 A1 | 2/2014 | Sonderegger |
| 2014/0039458 A1 | 2/2014 | Constantineau et al. |
| 2014/0058353 A1 | 2/2014 | Politis et al. |
| 2014/0074033 A1 | 3/2014 | Sonderegger et al. |
| 2014/0074037 A1 | 3/2014 | Bornhoft |
| 2014/0088509 A1 | 3/2014 | Sonderegger et al. |
| 2014/0088549 A1 | 3/2014 | Cole et al. |
| 2014/0088550 A1 | 3/2014 | Bene et al. |
| 2014/0100544 A1 | 4/2014 | Hwang |
| 2014/0135696 A1 | 5/2014 | Ruan et al. |
| 2014/0276416 A1 | 9/2014 | Nelson et al. |
| 2014/0276576 A1 | 9/2014 | Cole et al. |
| 2014/0316379 A1 | 10/2014 | Sonderegger et al. |
| 2014/0371715 A1 | 12/2014 | Farrell et al. |
| 2015/0045745 A1 | 2/2015 | Patton |

FOREIGN PATENT DOCUMENTS

| | | |
|---|---|---|
| EP | 1949926 A1 | 7/2008 |
| EP | 2158929 A1 | 3/2010 |
| JP | 2001-190683 | 7/2001 |
| JP | 2005-529717 | 10/2005 |
| JP | 2007-507288 | 3/2007 |
| WO | WO-9109637 A1 | 7/1991 |
| WO | WO-03026728 A1 | 4/2003 |
| WO | WO-2006062680 A1 | 6/2006 |
| WO | WO-2006085176 A1 | 8/2006 |
| WO | WO-2006097111 A2 | 9/2006 |
| WO | WO-2006116613 A1 | 11/2006 |
| WO | WO-2007056309 A1 | 5/2007 |
| WO | WO-2008014792 A1 | 2/2008 |
| WO | WO-2008092958 A2 | 8/2008 |
| WO | WO-2009139857 A1 | 11/2009 |
| WO | WO-20100142641 A1 | 12/2010 |

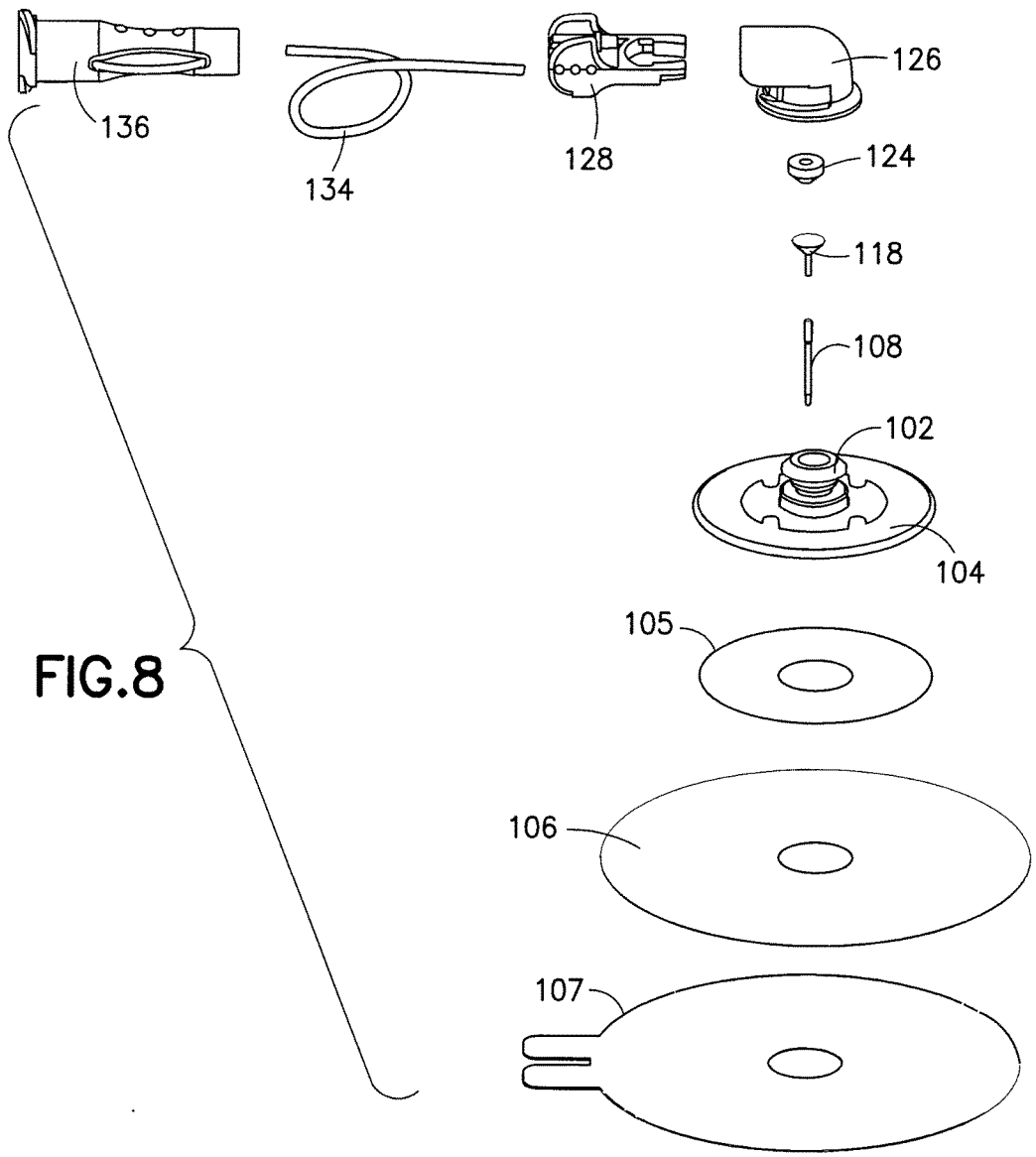

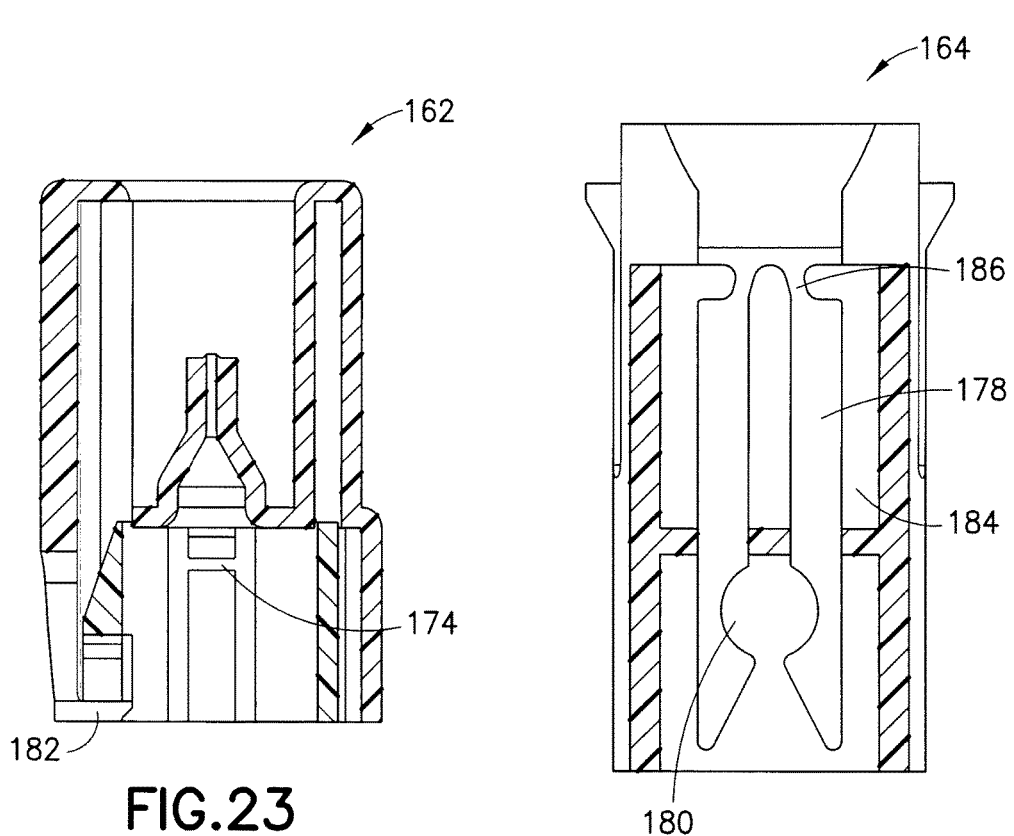

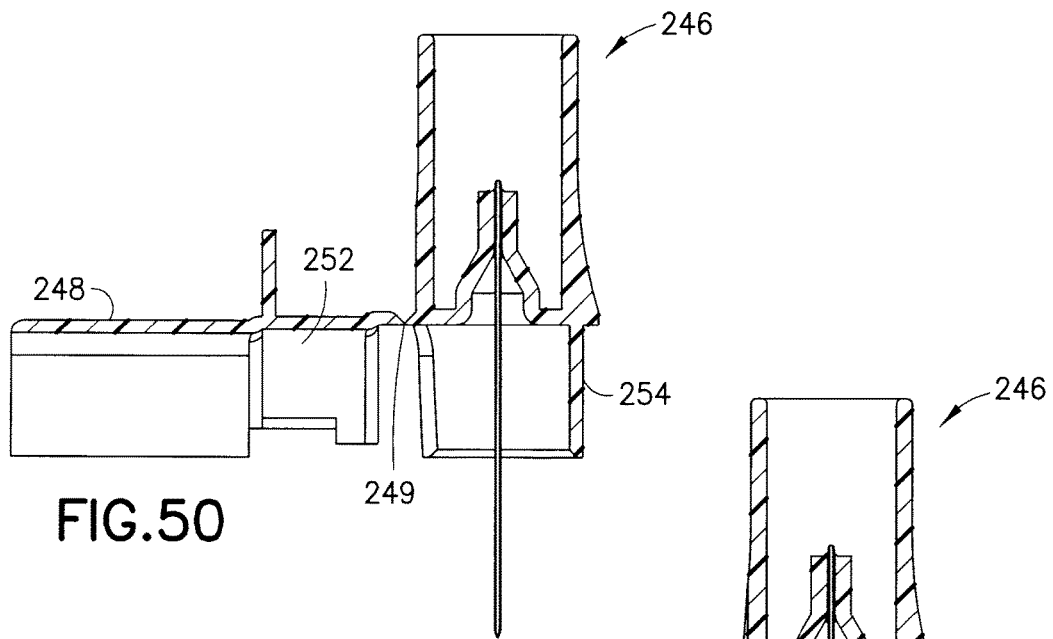
FIG.50
FIG.51
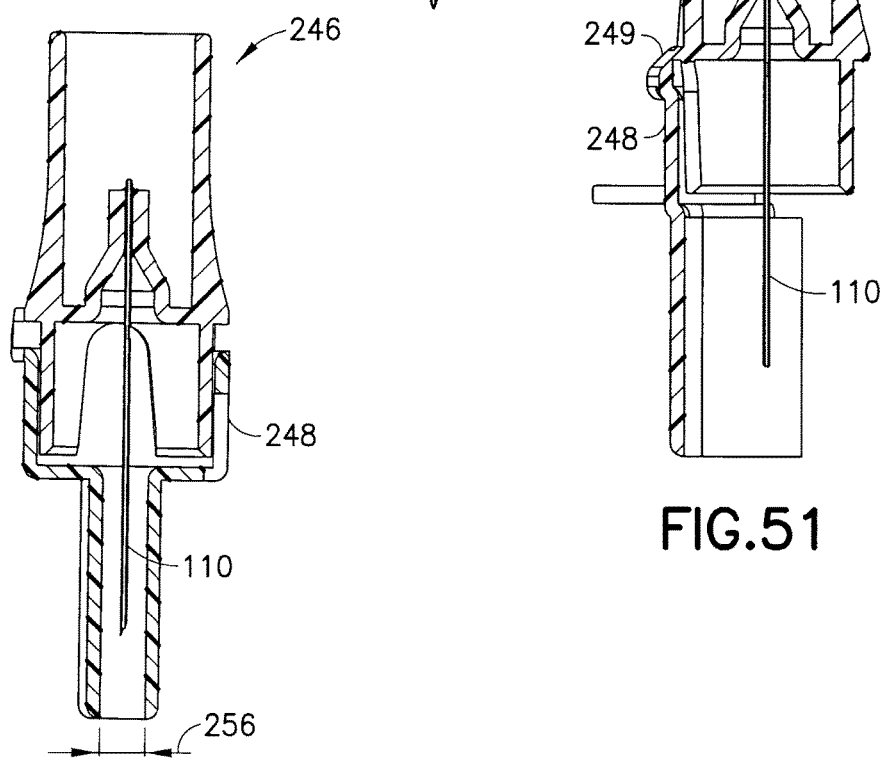
FIG.52

NEEDLE SHIELDING ASSEMBLIES AND INFUSION DEVICES FOR USE THEREWITH

CROSS-REFERENCE TO RELATED APPLICATIONS

This application is a continuation of U.S. patent application Ser. No. 14/362,102, filed May 30, 2014, which is the U.S. national stage of international patent application Ser. No. PCT/US12/68604, filed Dec. 7, 2012, which claims priority under 35 USC § 119(e) from U.S. provisional patent applications Ser. Nos. 61/568,074 and 61/692,985, filed on Dec. 7, 2011 and Aug. 24, 2012, respectively, the disclosures of each of these applications being hereby incorporated by reference in its entirety.

FIELD OF THE INVENTION

The present invention relates generally to needle shielding assemblies, and more particularly, to introducer needle shielding assemblies for use with infusion devices, such as subcutaneous infusion devices used in conjunction with an infusion pump in the infusion of insulin and other medicaments.

BACKGROUND OF THE INVENTION

One mode of insulin infusion treatment for diabetes includes infusion pump therapy via a catheter, needle or other type of cannula. Infusion pumps offer the advantages of continuous infusion of insulin, precision dosing, and programmable delivery schedules. Together, these advantages result in more accurate blood glucose control. In this mode of insulin infusion treatment, the infusion pump remains attached to the user and required doses of insulin are delivered to the user via the pump.

One type of cannula is a catheter, which generally is a tube that can be inserted into the body to permit the administration of fluids. In infusion pump therapy, the types and sizes of the catheter may vary, but generally, the catheter is a thin, flexible tube. In some uses, however, it may be larger and/or rigid.

One type of conventional infusion set is sold as the Quick-Set® infusion set by Medtronic. In such devices, the infusion pump includes a catheter assembly connected to a pump via a tubing set, and a separate insertion device inserts and/or attaches the catheter assembly into to a user via an introducer needle provided as part of the infusion set. The infusion set and insertion device can also be combined, as in the Mio® infusion set sold by Medtronic, which is an "all-in-one" design that combines the infusion set and insertion device into one unit.

A conventional infusion device can include a fluid connector hub, which may be releasably attached to a base that can be secured to a user's skin. An infusion pump supplies fluid to a catheter via the fluid connector hub/base engagement.

With conventional infusion devices, however, there are concerns that, after insertion of the catheter and removal of the insertion device, the introducer needle is exposed and may cause physical damage from a needle stick. There are also concerns over the difficulty of balancing the force required to disconnect the tubing without pulling the catheter from the user's skin versus having enough retention force to secure the infusion components for everyday infusion. Another concern is that there may be a need to design a rotational lock between the fluid connector hub and the base post. Yet another concern is that the separation force needs to be designed such that if a user accidentally snags the extension tubing on an external structure (e.g., a doorknob), the extension tubing will disconnect from the fluid connector hub without removing the catheter from the user's skin, thus saving the patient from the need to obtain, re-insert, and connect a new infusion set.

SUMMARY OF THE INVENTION

An object of embodiments of the present invention is to substantially address the above and other concerns, and to provide improved infusion devices. Another object of embodiments of the present invention is to provide an improved needle shield device configured to conceal and/or protect an introducer needle after insertion of a catheter.

These and other objects are substantially achieved by providing an introducer needle assembly including a needle and a needle shield device. The needle has a sharpened end and an opposing end, and is insertable through a base. The needle shield device includes an inner shield connectable to at least one of the base and a fluid connector connectable to the base, and an outer shield fixedly connected to the opposing end of the needle and displaceable relative to the inner shield between a first position, in which the sharpened end of the needle is exposed outside the inner shield, and a second position, in which the sharpened end of the needle is shielded by the inner shield. Interaction between portions of the inner and outer shields during or after proximal displacement of the outer shield from the first position to the second position automatically releases or permits release of the inner shield from connection to the at least one of the base and the fluid connector.

These and other objects are also substantially achieved by providing a needle assembly including a needle and a needle shield device. The needle has a sharpened end and an opposing end, and is insertable through a base. The needle shield device includes an inner shield connectable to at least one of the base and a fluid connector connectable to the base, and an outer shield fixedly connected to the opposing end of the needle. Interaction between portions of the inner and outer shields during or after the outer shield is proximally displaced relative to the inner shield by a predetermined distance causes automatic release or permits release of the inner shield from connection to the at least one of the base and the fluid connector.

These and other objects are also substantially achieved by providing a method, including providing a needle assembly that includes a needle and a needle shield device. The needle has a sharpened end and an opposing end, the needle being insertable through a base. The needle shield device includes an inner shield connectable to at least one of the base and a fluid connector connectable to the base, and an outer shield fixedly connected to the opposing end of the needle. The method also includes displacing the outer shield by a predetermined distance relative to the inner shield, and, by interaction between portions of the inner and outer shields during or after the outer shield is proximally displaced, releasing the inner shield from connection to the at least one of the base and the fluid connector.

These and other objects are also substantially achieved by providing a needle assembly that includes a needle and a needle shield device. The needle has a sharpened end and an opposing end, and is insertable through a base. The needle shield device includes a first shield, a second shield, and a biasing element. The first shield is connectable to one of the base and a fluid connector connectable to the base, the first shield being fixedly connected to the opposing end of the needle and having at least one cantilevered arm with a tapered edge. The second shield has a stop. In a first position of the second shield relative to the first shield, in which the sharpened end of the needle is exposed outside the second shield, the stop engages with the tapered edge of the first shield to create a jam connection with the one of the base and the fluid connector.

The first and second shields having a common central axis. The biasing element biases the first shield axially away from the second shield. Proximal displacement of the second shield relative to the one of the base and the fluid connector proximally displaces the first shield along with the second shield until the first shield is no longer connected to the one of the base and the fluid connector. When the first shield is no longer connected to the one of the base and the fluid connector, under the force of the spring, the cantilevered arm of the first shield deflects relative to the stop and the first shield displaces axially relative to the second shield to cover the sharpened end of the needle.

These and other objects are also substantially achieved by providing a needle assembly that includes a and a needle shield device. The needle has a sharpened end and an opposing end, and is insertable through a base. The needle shield device includes a needle hub and a shield. The needle hub is fixedly connected to the opposing end of the needle. The needle hub has a hub base disposed at a proximal end thereof shrouding a portion of the needle. The shield has an inner cavity and is hingedly connected to the needle hub. The shield is also rotatable relative to the needle hub between a first position in which the sharpened end of the needle is exposed outside the needle shield device, and a second position, in which the sharpened end of the needle is covered within the cavity. Upon rotating to the second position, the shield engages and latches with the hub base.

These and other objects are also substantially achieved by providing a needle assembly that includes a needle and a needle shield device. The needle has a sharpened end and an opposing end, and is insertable through a base. The needle shield device includes first and second shields. The second shield is displaceable relative to the first shield between a first position, in which the sharpened end of the needle is exposed outside the first and second shields, and a second position, in which the sharpened end of the needle is shielded by the first and second shields. One of the first and second shields is connectable to at least one of the base and a fluid connector connectable to the base. One of the first and second shields is fixedly connected to the opposing end of the needle. Interaction between portions of the inner and outer shields during or after proximal displacement of the second shield from the first position to the second position automatically releases or permits release of the one of the first and second shields from connection to the at least one of the base and the fluid connector.

These and other objects are also substantially achieved by providing an infusion set, including a base and a locking fluid connector. The base includes a base portion, a septum, and a cannula. The base portion has a column extending proximally therefrom. The column includes a plurality of inverted J-shaped engagement structures with cantilevered ends. The engagement structures form engagement pockets therein and are circumferentially arrayed around the column and separated by a plurality of slots. The septum is disposed within the column. The cannula protrudes distally from the base portion and is in fluid communication with a distal side of the septum.

The locking fluid connector includes a tubing portion having a tubing port for connecting tubing thereto, and a hub portion for connecting with the base. The hub portion includes a domed portion and a blunt cannula for penetrating the septum. The blunt cannula extends from the domed portion and is fluidly connected with the tubing port. The hub portion also includes a plurality of engagement fingers protruding radially inward, and a spring element held within the domed portion by the engagement fingers. The engagement fingers are alignable with the aligning the slots. The locking fluid connector is displaceable toward the base when the blunt cannula is aligned with the septum and the engagement fingers are aligned with the slots, thereby compressing the spring element. The locking fluid connector is rotatable about the column once the engagement fingers have distally cleared the cantilevered ends of the engagement structures. The locking fluid connector is displaceable away from the base under the force of the spring element with the engagement fingers disposed within the engagement pockets to lock the fluid connector to the base in one of a plurality of discrete rotational orientations.

These and other objects are also substantially achieved by providing an infusion set, including a base and a fluid connector. The base includes a base portion, a septum, and a cannula. The base portion has a column extending proximally therefrom. The column includes a ball-shaped base latch at its proximal end. The septum is disposed within the column. The cannula protrudes distally from the base portion and is in fluid communication with a distal side of the septum.

The locking fluid connector includes a tubing portion having a tubing port for connecting tubing thereto, and a hub portion for connecting with the base. The hub portion includes a domed portion and a blunt cannula for penetrating the septum. The blunt cannula extends from the domed portion and is fluidly connected with the tubing port. The hub portion also includes a plurality of distally cantilevered snap latches, each having an internal angular profile to snap over the base latch to connect the fluid connector with the base.

BRIEF DESCRIPTION OF THE DRAWINGS

The various objects, advantages and novel features of the exemplary embodiments of the present invention will be more readily appreciated from the following detailed description when read in conjunction with the appended drawings, in which:

FIG. 8 is an exploded view of the fluid connector and base of FIG. 5;

FIGS. 19-24 are perspective and cross-sectional views of a needle shield device in accordance with an exemplary embodiment of the present invention;

FIG. 50 is a cross-sectional view of the needle shield device of FIG. 47 prior to deployment of the needle shield;

FIGS. 51 and 52 are cross-sectional views of the needle shield device of FIG. 48 after deployment of the needle shield;

DETAILED DESCRIPTION OF EXEMPLARY EMBODIMENTS

Figure 1:
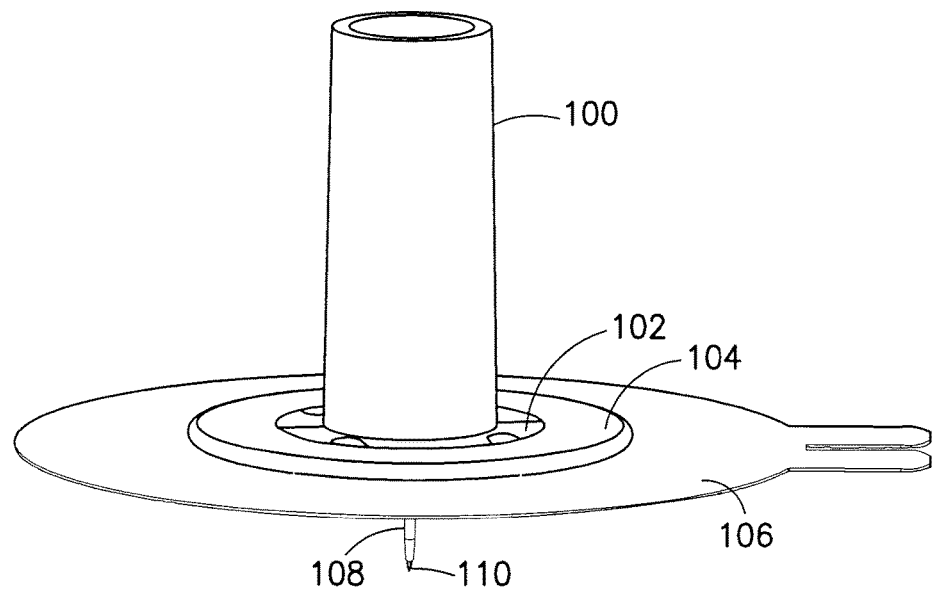
FIG. 1 is a perspective view of a needle hub connected to an infusion set base in accordance with an exemplary embodiment of the present invention.

As will be appreciated by one skilled in the art, there are numerous ways of carrying out the examples, improvements and arrangements of infusion-associated devices disclosed herein. Although reference will be made to the exemplary embodiments depicted in the drawings and the following descriptions, the embodiments disclosed herein are not meant to be exhaustive of the various alternative designs and embodiments that are encompassed by the disclosed invention. As will be understood by one skilled in the art, terms such as up, down, bottom, top, proximal, and distal are relative, and are employed to aid illustration, but are not limiting.

FIG. 1 illustrates an exemplary embodiment of an infusion set comprising an introducer needle hub 100 engaged with a base 102. The base 102 engages a flexible disc 104 positioned between the base 102 and a user. The flexible disc 104 provides improved comfort and mobility of the device because it moves with the user during physical activity while minimizing contact of the rigid portions of the base 102 with the user. The flexible disc 104 is attached to an adhesive patch or pad 106 having an adhesive backing, which is used to secure the base 102 to the user's skin. FIG. 1 illustrates a state in which the introducer needle hub 100 and base 102 are ready to facilitate insertion of a soft (flexible) catheter 108 and an introducer needle 110 into the user.

Figure 2:
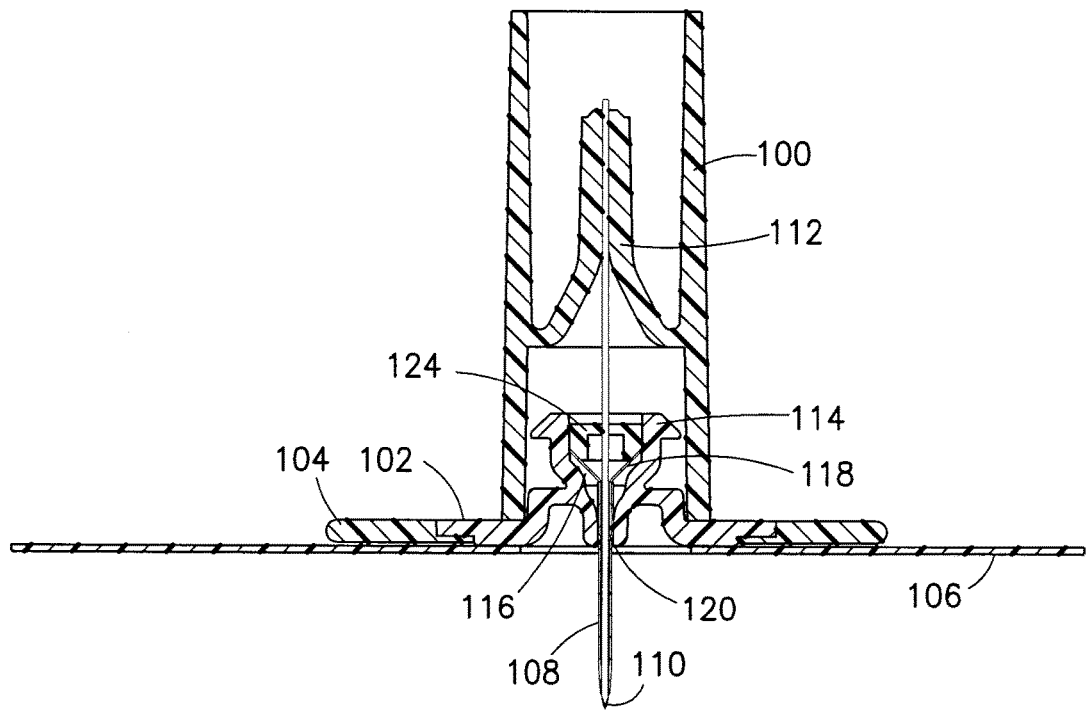
FIG. 2 is a cross-sectional view the needle hub and base of FIG. 1.

FIG. 2 is a cross-sectional view of the base 102 and introducer needle hub 100 configuration shown in FIG. 1. The introducer needle 110 is fixed to a needle mounting structure 112 within the introducer needle hub 100, thus fixing the introducer needle 110 against axial movement relative to the hub 100. The introducer needle hub 100 is used to insert the introducer needle 110 and the catheter 108 into the user without requiring the user to hold or manipulate the introducer needle 110 directly. The introducer needle 110 is preferably a hollow stainless steel needle with a sharp beveled distal end.

Figure 3:
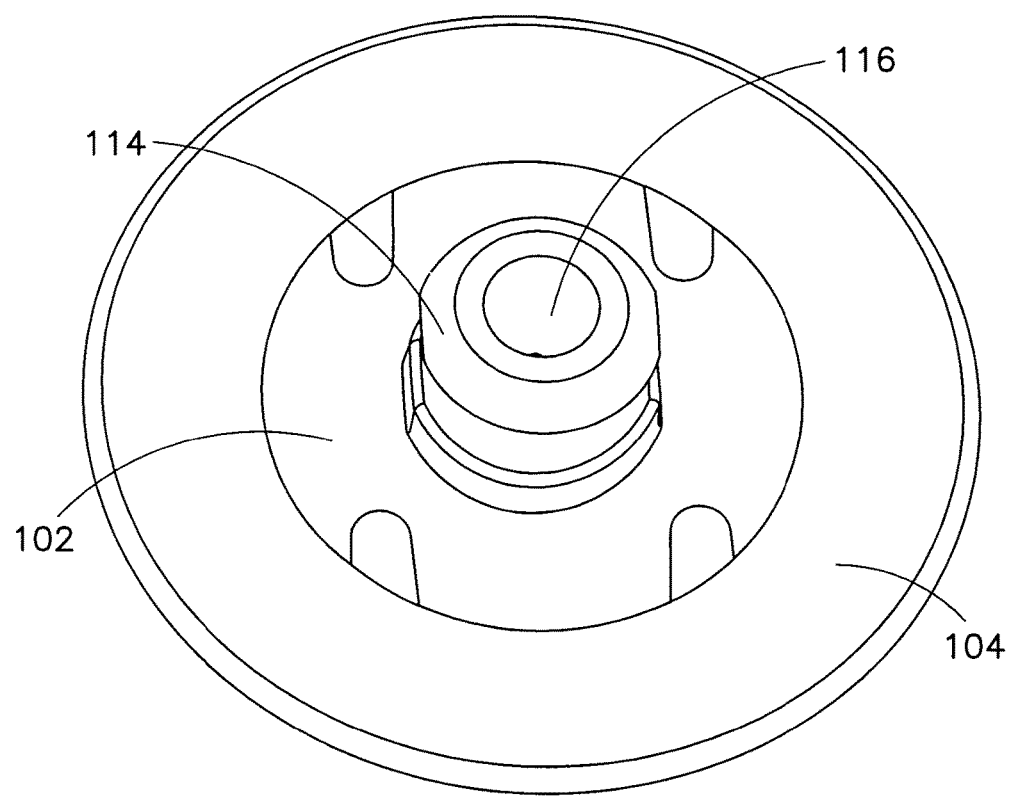
FIG. 3 is a perspective view of the base of FIG. 1.
Figure 4:
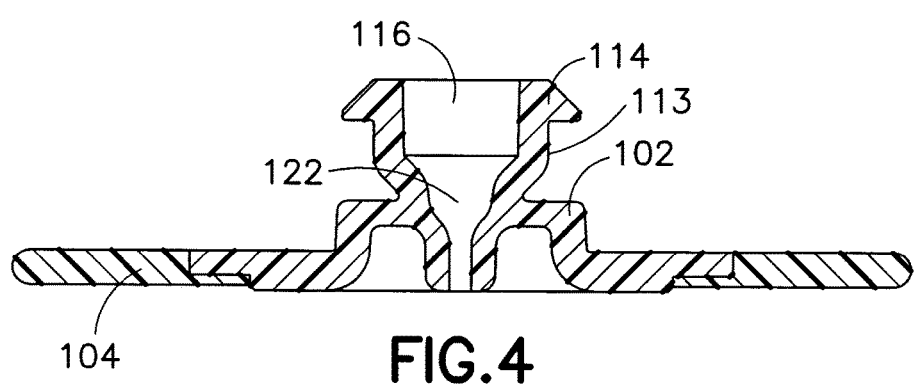
FIG. 4 is a cross-sectional view of the base of FIG. 1.

FIGS. 2-4 further illustrate features of the base 102. The base 102 includes a columnar post 113 surrounding an internal cavity 116. A mushroom-shaped base latch 114 is disposed at the proximal end of the post 113 The internal cavity 116 generally extends through the center of the base 102 providing a fluid passageway through the base 102. As shown, for example, in FIG. 2, the internal cavity 116 of the base 102 receives a retaining wedge 118 and a catheter 108. The wedge 118 has a funnel shape with a hollow center portion that narrows from a broad end to a narrow end 120. The narrow end 120 of the wedge 118 has a tapered end used to receive a terminal end of the catheter 108. The catheter 108 is forced over the narrow end 120 of the wedge 118 and the wedge/catheter assembly is inserted into the internal cavity 116 of the base 102.

Due to the flexible characteristics of the catheter 108, it may have a tendency to bunch up within the base 102 and therefore, the base 102 provides an additional cavity area 122 to accommodate excess catheter 108 material that may accumulate within the base 102 during the installation of the catheter onto the wedge 118. A pre-slit resilient septum 124 is also retained within the internal cavity 116 of the base 102. According to an exemplary embodiment, the septum 124 is held in place within the base 102 by a press fit, which provides a friction force between the septum 124 and both the base 102 and the wedge 118. Alternatively, the septum 124 may be fixed within the base 102 by an adhesive or by swaging plastic material from the base 102 over the top of the septum.

FIGS. 3 and 4 also illustrate first and second molded shots used in manufacturing base 102. The second molded shot (disc 104) may be of the same material as the first shot or may be of a different, more flexible material, which may include a silicone or thermoplastic elastomer, and thus, may be the flexible disc 104. As shown in FIG. 3, cutouts or holes 103 in the base 102 become filled with the material for the flexible disc 104, and thus, facilitate bonding between the base 102 and the flexible disc 104.

Figure 5:
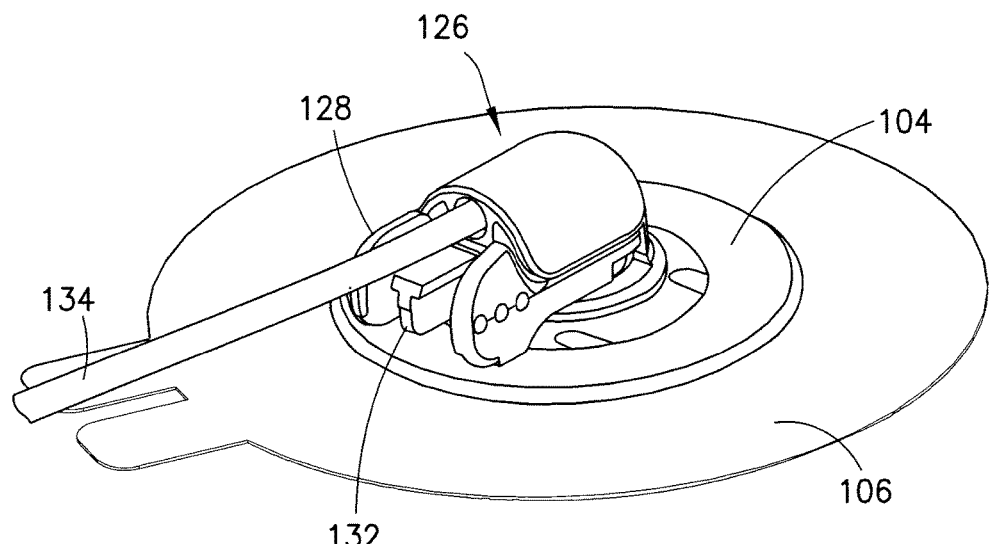
FIG. 5 is a perspective view of a fluid connector attached to the base of FIG. 1 in accordance with an embodiment of the present invention.
Figure 6:
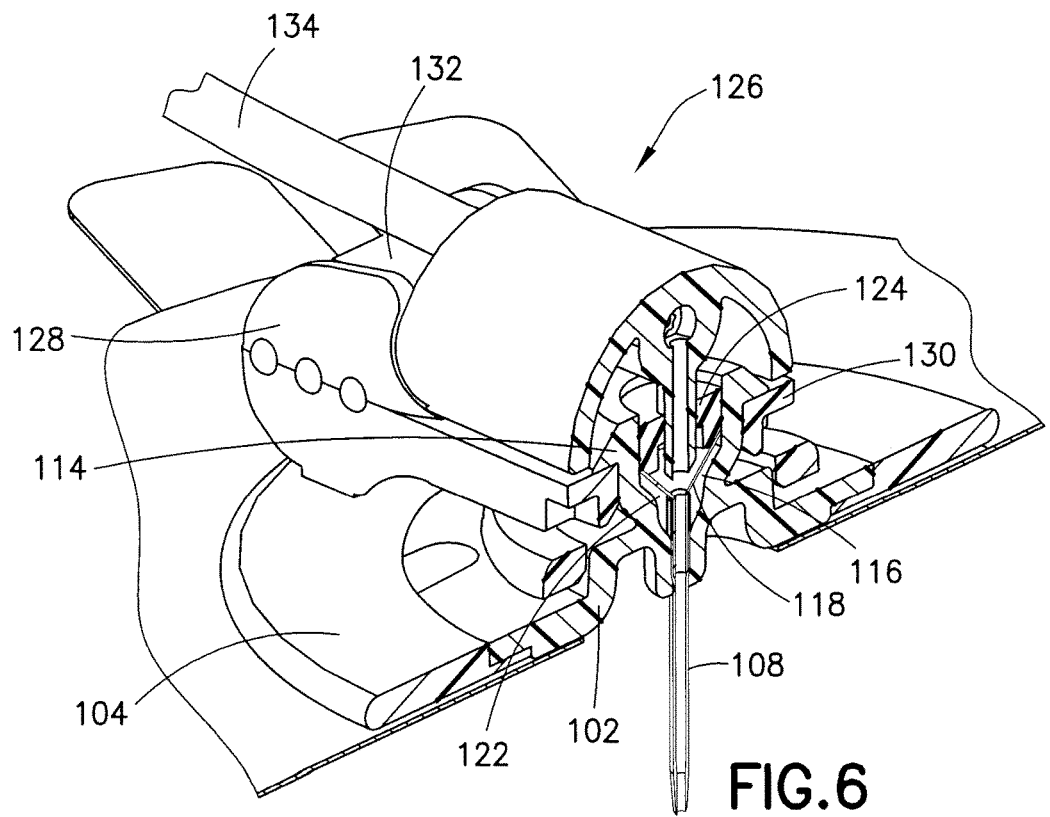
FIG. 6 is a cross-sectional view of the fluid connector and base of FIG. 5.
Figure 7:
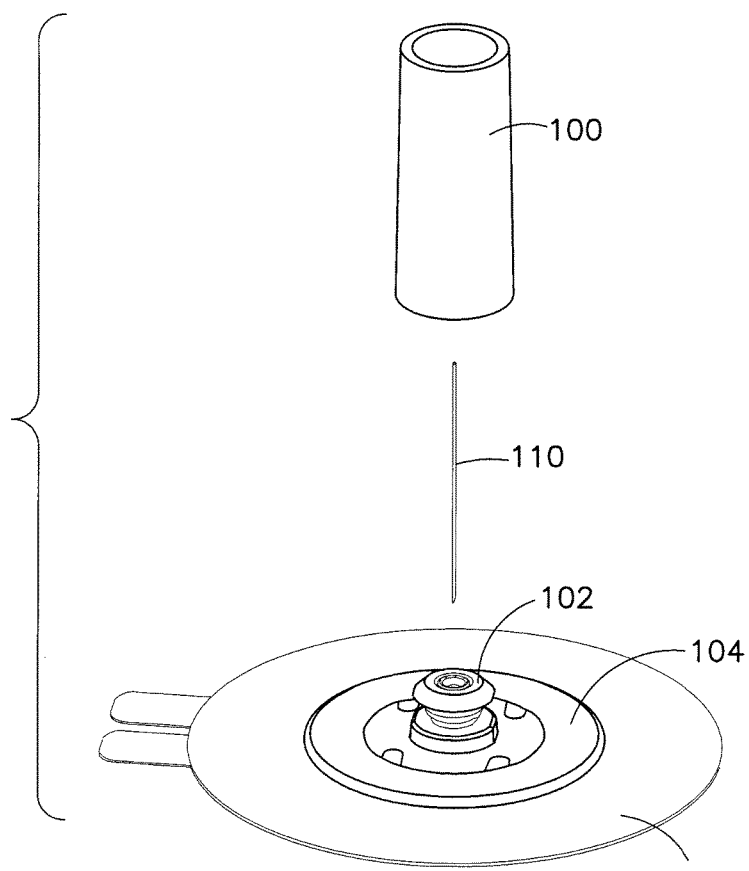
FIG. 7 is an exploded view of the needle hub of FIG. 1.

FIGS. 5 and 6 illustrate a fluid connector hub or fluid connector 126 connected to the base 102, and FIG. 7 illustrates an exploded view of the introducer needle hub 100 and base 102. The fluid connector hub 126 includes activation levers 128, fluid connector latches 130, and a rigid stop 132 (best shown in FIG. 11). The user attaches the fluid connector 126 to the base 102 by pressing the fluid connector axially down onto the base 102 and snapping it in place. In this process, the latches 130 and activation levers 128 resiliently deflect to allow the latches to pass over the mushroom-shaped base latch 114. Subsequently, the laches 130 and activation levers 128 return substantially to their undeformed or less deformed positions with the latches resiliently engaging the underside of the mushroom-shaped base latch 114 to prevent axial displacement of the fluid connector 126 relative to the base 102. In other words, during connection, the fluid connector latches 130 slide over the mushroom-shaped base latch 114 and resiliently return to a position where they snap and engage the base 102 via engagement with the post 113 and the base latch 114.

The user removes the fluid connector 126 by pressing the activation levers 128 together until they engage the rigid stop 132, thereby disengaging the latches 130 from the mushroom-shaped base latch 114. The user then lifts the fluid connector 126 axially away from the base 102.

In this exemplary embodiment, the activation levers 128 and the fluid connector latches 130 are molded from a resilient plastic material as a separate component from the fluid connector 126. The activation levers 128 and fluid connector latches 130 pivot on a living hinge. This may simplify manufacturing and reduce mold complexity. The rigid stop 132 ensures that both of the fluid connector latches 130 travel far enough to completely disengage from the mushroom-shaped base latch 114. The rigid stop 132 also provides a stable anchor for the activation levers 128 during the handling of the fluid connector 126. Additionally, according to one embodiment, the fluid connector 126 can freely rotate 360 degrees about the base 102, which provides the user with the ability to position the extension tubing 134, which connects the fluid connector 126 to an infusion pump.

Figure 9:
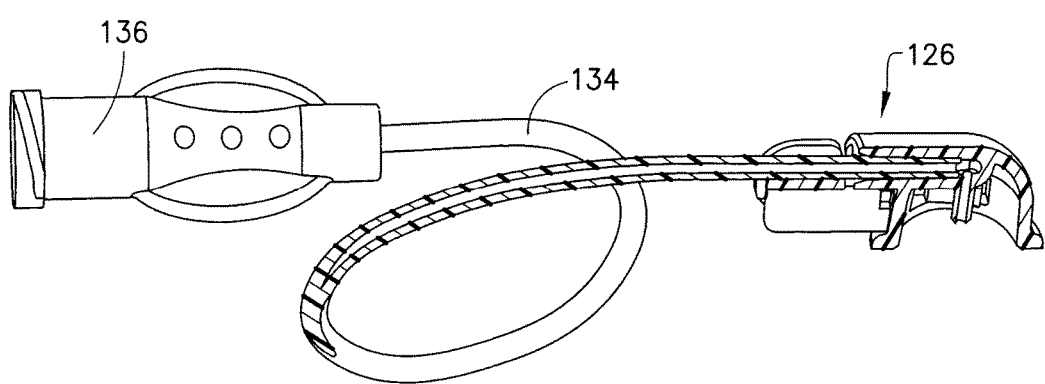
FIG. 9 is perspective view of the fluid connector of FIG. 5 and a reservoir connector.

FIGS. 8 and 9 illustrate an exploded and perspective view, respectively, of the components of an exemplary embodiment of an infusion set. The infusion set includes the fluid connector 126 and the base 102 as described above, and also includes the extension tubing 134 connecting the fluid connector 126 to a reservoir connector 136 that connects to an infusion pump, as well as a base adhesive 105 for connecting the adhesive patch 106 to the base 102 and/or the flexible disc 104, and an adhesive backing 107 for selectively protecting the distal adhesive surface of the adhesive patch 106.

Figure 10:
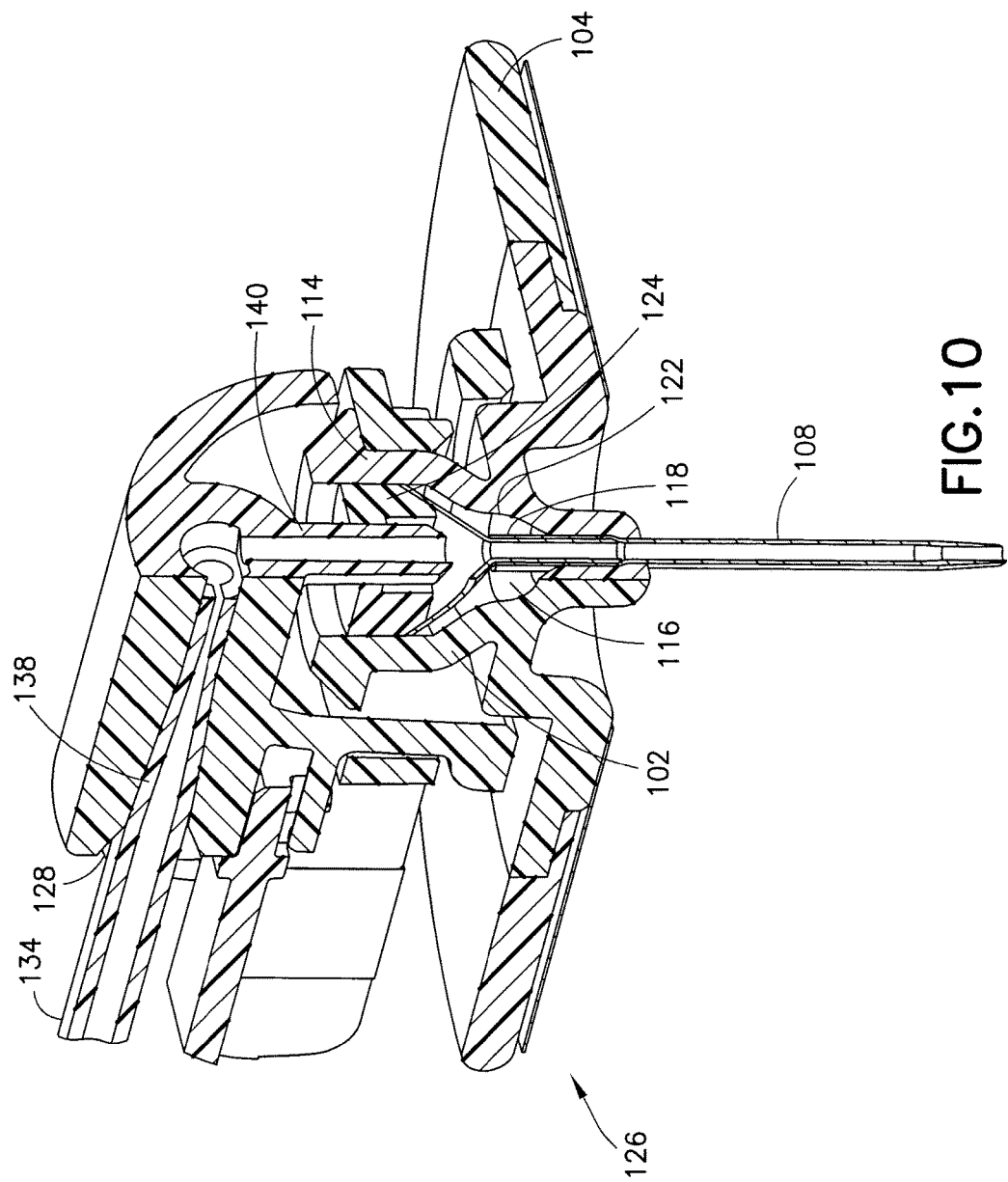
FIG. 10 is another cross-sectional view of the fluid connector and the base of FIG. 5.

FIG. 10 is a sectional view depicting a connected fluid path provided by the fluid connector 126 and the base 102. In this embodiment, the extension tubing 134 is connected to a tubing port 138 on the fluid connector 126. According to one embodiment, the tubing port 138 provides a press fit connection for the extension tubing 134, facilitating fluid flow from the infusion pump, through the extension tubing 134 and into the fluid connector 126. According to another embodiment, glue, or another bonding mechanism, such as solvent bonding, is used to secure the extension tubing 134 to the tubing port 138. The fluid path continues from the tubing port 138 into a molded cannula 140.

The molded cannula 140 extends in a direction substantially perpendicular to the longitudinal direction of the tubing port 138. In this embodiment, the molded cannula 140 is a rigid, substantially tubular member made of plastic and having either a tapered or rounded terminal end. The terminal end of the molded cannula 140 is used to penetrate through a pre-formed slit in the septum 124, thus providing a sealed fluid connection between the extension tubing 134 and the catheter 108. Fluid flows through the molded cannula 140, through the septum 124, then through the wedge 118 and into the catheter 108. The septum 124 provides a self-sealing feature, preventing fluid from exiting or leaking out of the base 102, except through the catheter 108. According to one embodiment, the molded cannula 140 is formed as an integral part of the fluid connector 126.

Figure 11:
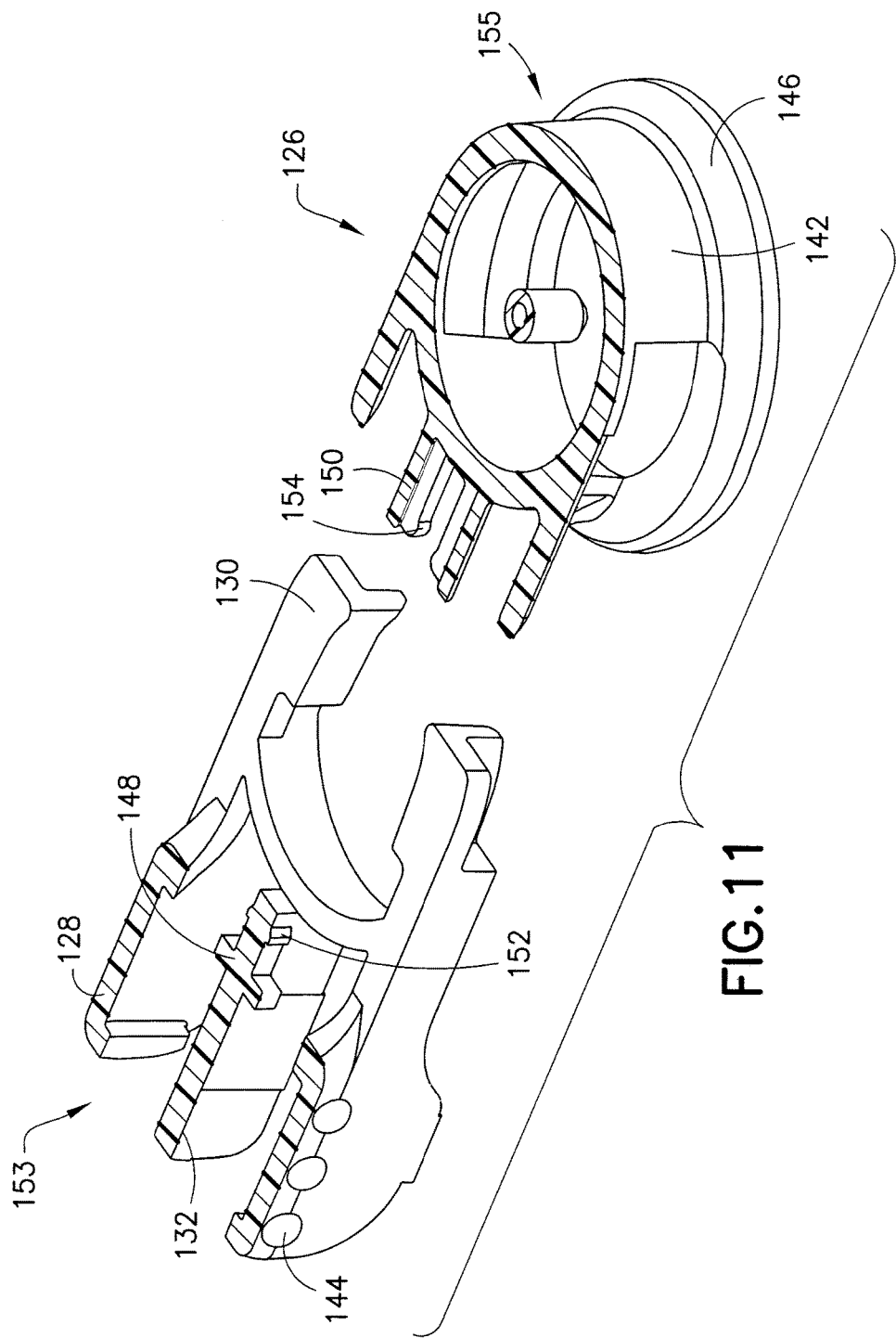
FIG. 11 is an exploded view of the fluid connector of FIG. 5.

FIG. 11 is an exploded, perspective, cross-sectional view of the fluid connector 126. In this exemplary embodiment, the fluid connector 126 is formed using two distinct components: a first component 153, including the fluid connector latches 130 and the corresponding activation levers 128, and a second component 155, including the fluid connector shroud 142 (the top half of each component being omitted for clarity). The activation levers 128 have finger bumps 144 to aid the user in locating and using the activation levers 128. Alternatively, the finger bumps 144 may be replaced with a ridge or divots that can provide tactile feedback to the user regarding where to press to release the fluid connector 126 from the base 102. According to one embodiment, the activation levers 128 can have a different color than the fluid connector 126 to provide a visual indicator for the same purpose. The fluid connector shroud 142 of the fluid connector 126 has a smooth rounded exterior surface that aids in minimizing snagging or catching the fluid connector 126 on clothing or other objects during use. At the base of the fluid connector 126 there is a circular anchoring ring 146. The anchoring ring 146 forms a foundation and provides added stability around the base 102 when the fluid connector 126 engages with the base 102.

FIG. 11 also illustrates how the fluid connector shroud 142 and the fluid connector latches 130 are assembled. A male T-slot 148 feature on the first component 153 engages with a female T-slot 150 feature on the second component 155. Detents 152 and 154 on the first and second components 153 and 155 provide a mechanical lock between the two components. Alternatively, the fluid connector latches 130 and the fluid connector shroud 142 can be formed as a single integral molded plastic piece.

Figure 12:
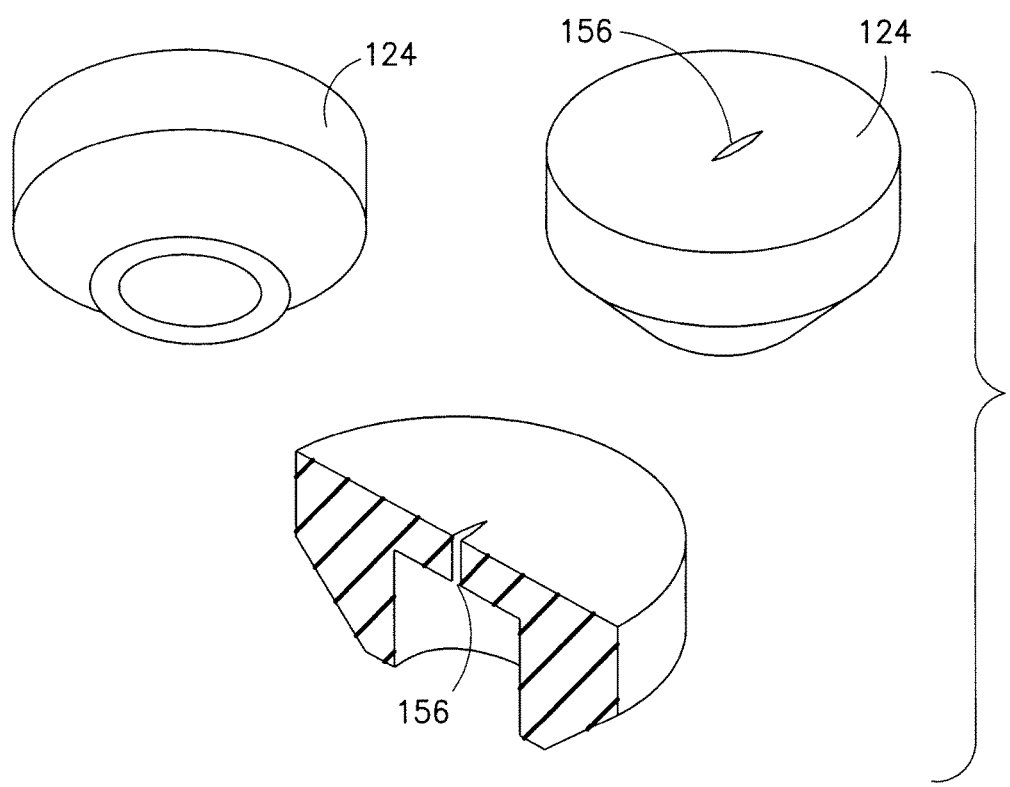
FIG. 12 illustrates opposing perspective views and a cross-sectional view of a split septum in accordance with an exemplary embodiment of the present invention.

FIG. 12 illustrates the self-sealing resilient septum 124, which has a pre-pierced center 156 (shown partially opened for illustrative purposes) to receive the blunt molded cannula 140 from the fluid connector 126 and facilitate penetration of the septum 124. According to one embodiment, the septum 124 I sunder inward radial compression to ensure a seal at all times, with or without the molded cannula 140 being present. The septum 124 can be made of a soft resilient material including, but not limited to silicones, isoprene rubbers, or bromobutyl rubbers. The septum 124 can be made from a combination of these materials as well. The septum 124 ensures a complete seal during infusion and when the fluid connector 126 is disconnected from the base 102. The slit geometry of the septum 124 may be a single straight slit or multiple, intersecting straight slits. The slit may also be curved to ensure a complete seal during infusion and while the connecter hub 126 is disconnected from the base 102.

Figure 13:
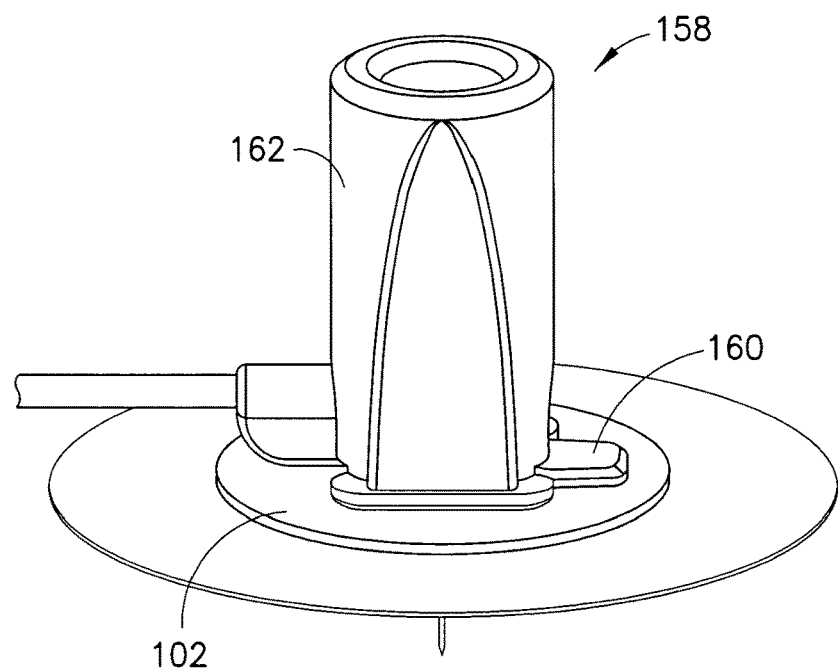
FIG. 13 is a perspective view of a needle shield device in accordance with an exemplary embodiment of the present invention.
Figure 14:
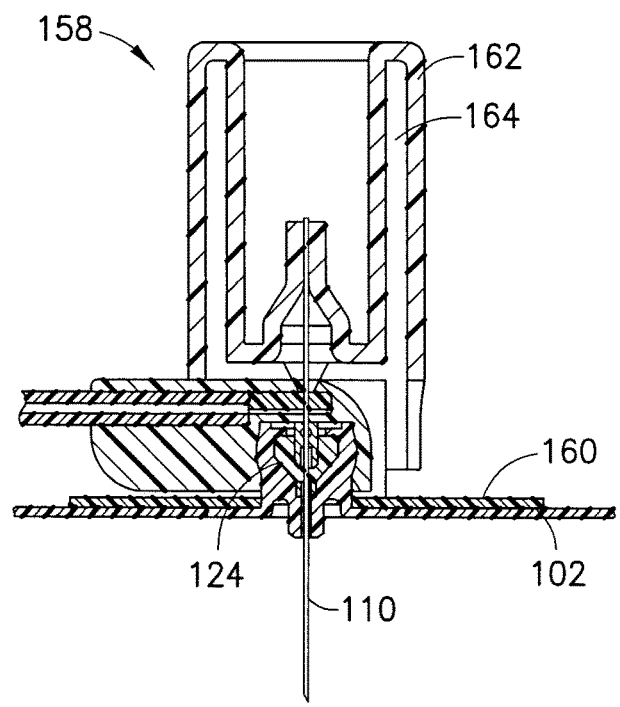
FIG. 14 is a cross-sectional view of the needle shield device of FIG. 13.

FIG. 13 illustrates a needle shield device 158 with a tab 160 connected to the base 102, ready for placement on the skin, and FIG. 14 is a cross-sectional view of the needle shield device 158 fully engaged with the base 102, piercing the septum 124 and catheter with the introducer needle 110. The needle shield device 158 includes an outer shield 162 and an inner shield 164 that is connected to the tab 160. The outer and inner shields 162, 164 are both preferably made of a molded plastic material that is substantially rigid but that has some degree of flexibility.

Figure 15:
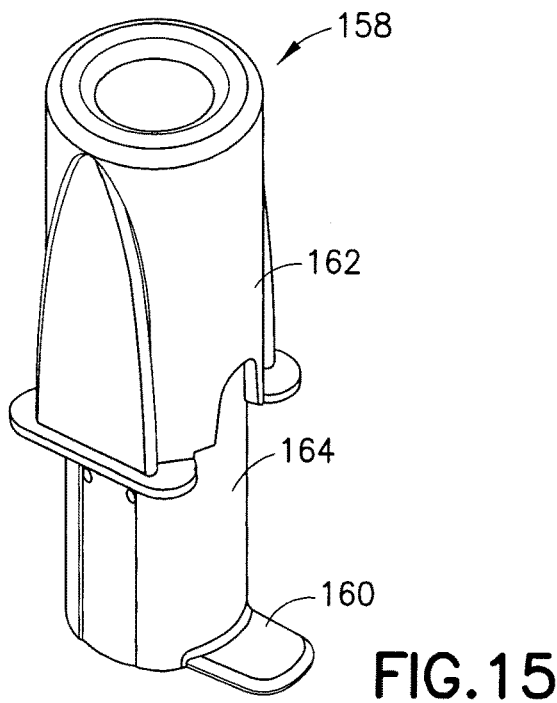
FIG. 15 is a perspective view of the needle shield device of FIG. 13 in a safe state.

FIGS. 15-18 illustrate the sequence of steps that occur to deploy the needle shield device 158 after the user has inserted the catheter 108 and removed the introducer needle 110 from the user's skin. For clarity, the base 102 is omitted from these figures. Briefly, the user holds the tab 160 on the base 102 while pulling up the outer shield 162, thereby extending the inner shield 164 disposed within the outer shield 162 to substantially conceal the introducer needle 110. As illustrated in FIG. 15, the inner shield 164 axially extends from the outer shield 162 to conceal the introducer needle 110.

Figure 16:
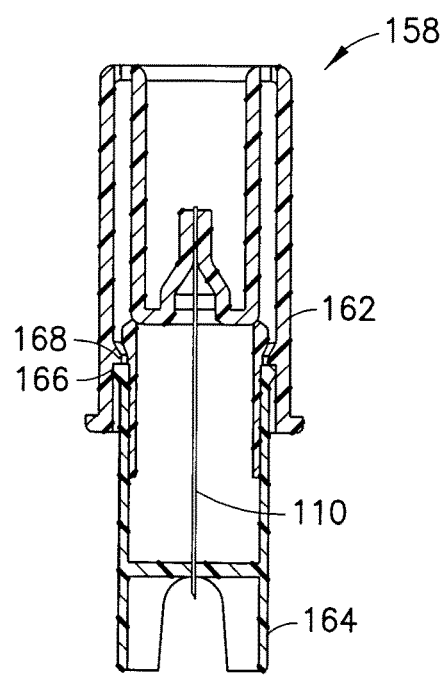
FIG. 16 is a cross-sectional view of the needle shield device of FIG. 13 in the safe state.

FIG. 16 illustrates that the inner shield 164 includes a flexible shield beam or arm 166 and the outer shield includes a shield latch 168. In the completely extended position of the inner shield 164, the shield beam 166 engages the shield latch 168 to prevent the inner shield 164 from moving in the axial direction of the introducer needle 110. The engagement of the shield latch 168 with the shield beam 166 provides the user with a safe needle holder which prevents the possibility of an accidental needle stick.

Figure 17:
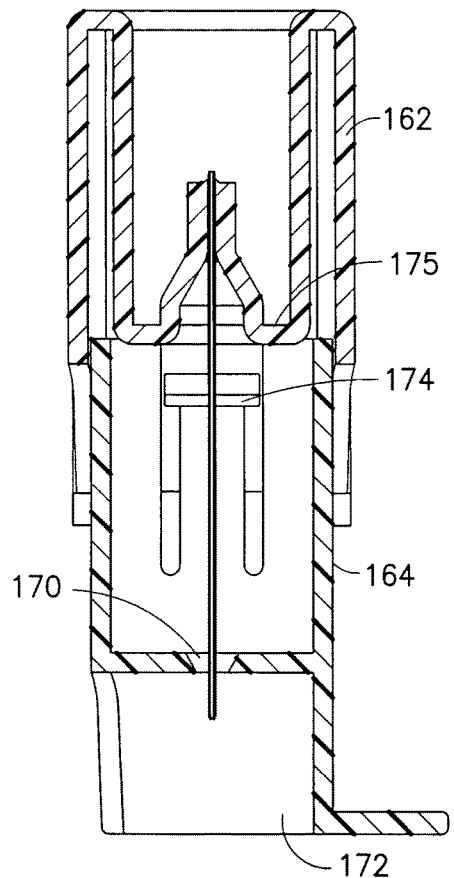
FIGS. 17 and 18 are additional cross-sectional views of the needle shield device of FIG. 13.
Figure 18:
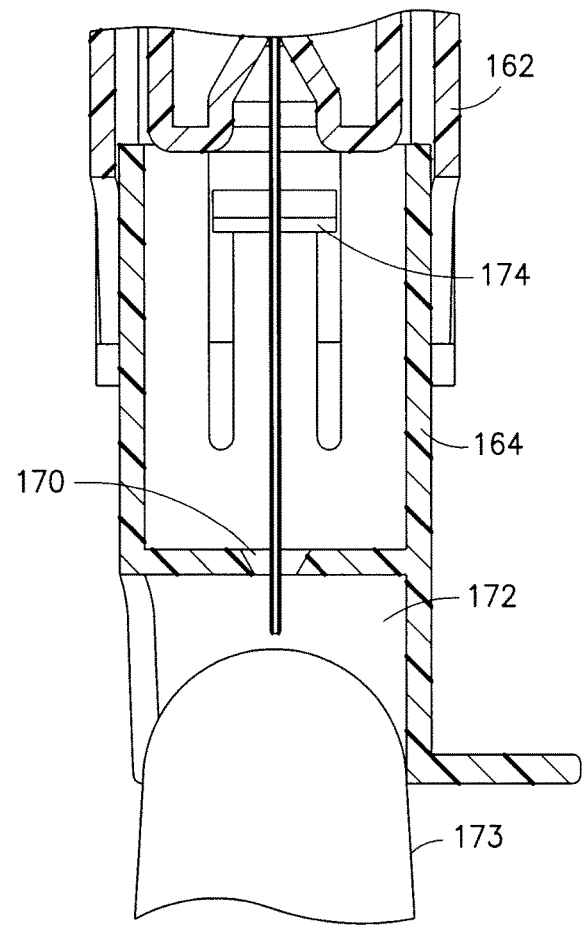

As shown in FIGS. 16 and 17, the inner shield 164 has an opening 170 that the introducer needle 110 extends through. The needle shield device 158 includes a shield well 172 in the inner shield 164 that surrounds the exposed introducer needle 110 such that an average finger 173 will not fit through the shield well 172 opening and contact the concealed introducer needle 110. The inner shield 164 also includes a detent 174 on an internal surface thereof that prevents the inner shield 164 from collapsing once it is fully extended with respect to the outer shield 162. More specifically, once the internal structure 175 (to which the insertion needle is fixed) passes the detent 174 during withdrawal of the needle, the detent 174 engages the structure 175 to prevent axial displacement of the outer shield 162 relative to the inner shield 164. Thus, the detent 174 acts as a secondary mechanism to the shield beam 166 and shield latch 168.

FIGS. 19-24 illustrate another exemplary embodiment of a needle shield device 176. The needle shield device 176 includes an outer shield 162 and an inner shield 164 similar to the example described in connection with FIGS. 13-18. The inner shield 164 includes cantilevered retention beams 178, which have notches 180 for engaging the extension tubing 134 therebetween when the inner shield 164 is retracted within the outer shield 162.

Figures 19, 20:
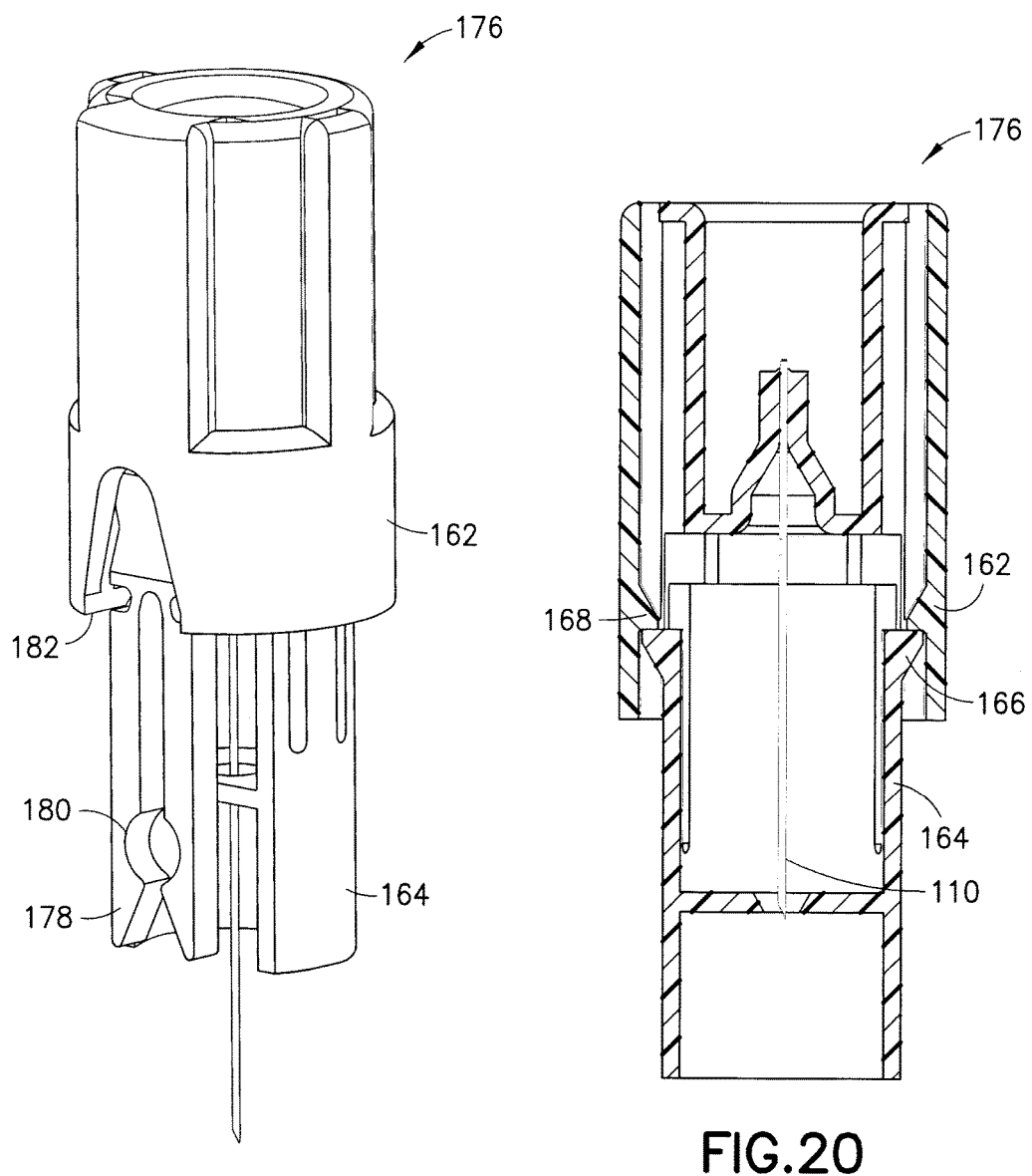

FIG. 20 illustrates a cross-sectional view of the needle shield device 176 with the inner shield 164 extended with respect to the outer shield 162. The inner shield 164 includes a flexible shield beam or cantilevered arm or inner shield latch beam 166 formed with, for example, a tapered edge or inner shield latch 167. The outer shield 162 includes a shield latch or outer shield latch 168 for engaging with the shield beam 166. That is, in the completely extended position of the outer shield 162 with respect to the inner shield 164, the shield beam 166 engages the shield latch 168 to prevent the inner shield 164 from moving in the axial direction of the introducer needle 110.

Figures 21, 22:
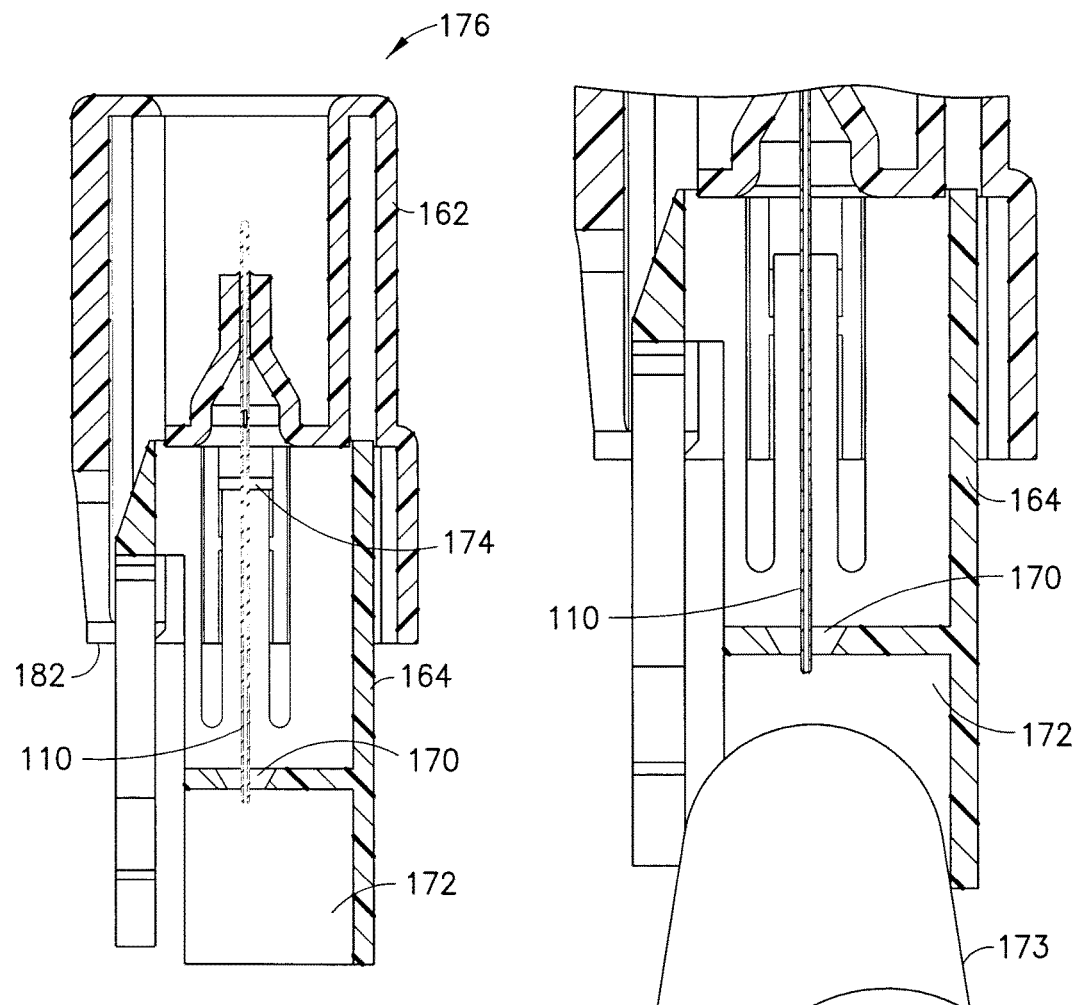

FIGS. 21 and 22 illustrate that the inner shield 164 has an opening 170 that the introducer needle 110 extends through. The needle shield 176 forms a shield well 172 surrounding and concealing introducer needle 110 such that an average finger will not fit through the shield well 172 opening and contact the concealed introducer needle 110. Like the needle shield device 158, the inner shield 164 of the needle shield device 176 includes a detent 174 that prevents the inner shield 162 from collapsing once it is fully extended with respect to the outer shield 162 (that is, a secondary shield mechanism).

FIG. 23 illustrates an example of the outer shield 162 with one or more cams 182. As the outer shield 162 is extended with respect to the inner shield 164, the outer shield cams 182 travel along the retention beams 178 to keep the retention beams 178 biased and in a substantially fixed position. Further, referring back to FIG. 21, the cam or hub latch 182 prevents the separation of the inner shield 164 from the outer shield 162 during extension of the inner shield 164 relative to the outer shield 162.

FIG. 24. illustrates an example of the inner shield 164 with the retention beams 178 having outer edges 184 that are contracted by the cams 182. The base of the retention beams 178 include a tapered base or shield latch 186 to connect the retention beams 178 to the rest of the inner shield 164 and allow the retention beams 178 to bend more freely when not biased. As described above, the retention beams 178 have notches 180 for engaging the infusion tubing hub while the inner shield 164 is retracted within the outer shield and while the outer shield is displaced relative to the inner shield 164. The outer edges 184 of the retention beams 178 are in contact with the cam 182 during displacement of the outer shield 162 relative to the inner shield 164, thereby keeping the retention beams 178 in a substantially fixed position (i.e. secured to the extension tubing 134) until the inner shield 164 is fully extended with respect to the outer shield 162.

When the inner shield 164 is fully extended with respect to the outer shield 162, the cams 182 reach the tapered bases 186. At this point (at the tapered bases 186), the width of the outer edges 184 of the retention beams 178 is less than distance between of the cam 182, and thus, the cams 182 no longer bias or contact the outer edges 184 of the retention beams or cantilevered latch beams 178. This allows the retention beams 178 to bend more freely due to the tapered base 186 and release the extension tubing disposed in in the notches 180 when the user continues to pull the needle shield device 176 axially upward, away from the base 102. That is, the contact between the outer edges 184 of the retention beams 178 and the cams 182 keep the extension tubing fixed to the needle shield device 176 until the inner shield 164 has been fully extended with respect to the outer shield 162. In the described example, the needle shield device 176 also provides the user with a mechanism to protect from an accidental needle stick and release the infusion set tubing hub in a single motion.

Figure 25:
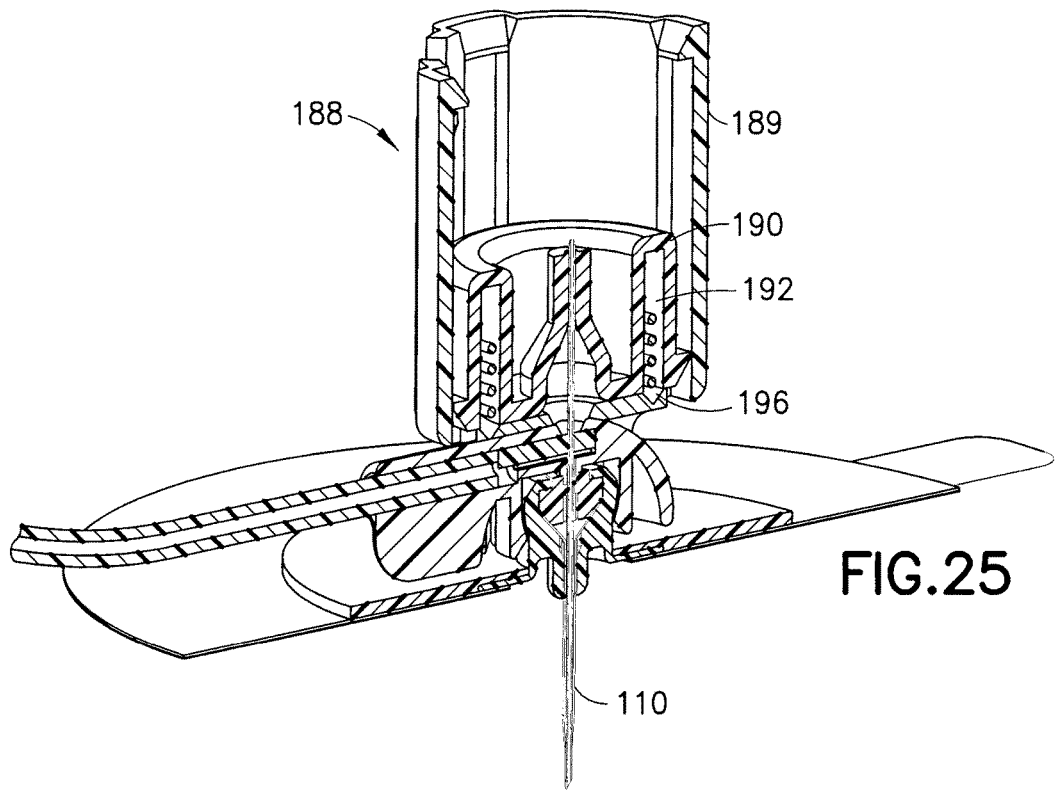
FIGS. 25 and 26 are perspective cross-sectional views of a needle shield device in accordance with an exemplary embodiment of the present invention.
Figure 26:
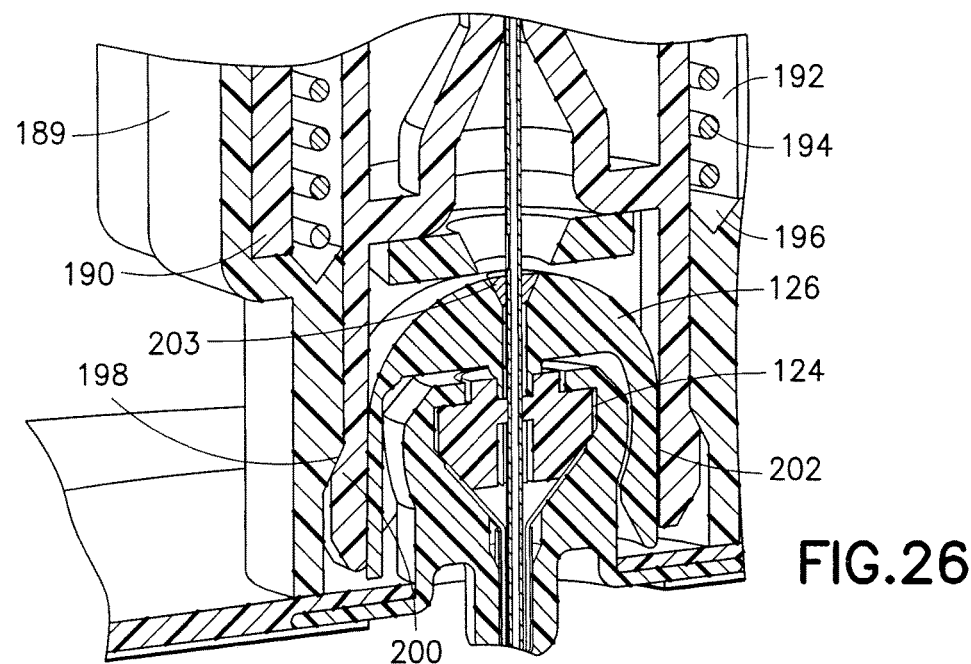

FIGS. 25-31 illustrate another exemplary embodiment of a needle shield device 188. FIG. 25 is a cross-sectional view of the needle shield device 188 that includes an outer shield 189 and a pre-biased inner shield 190. As shown in FIG. 26, the pre-biased inner shield 190 has a chamber 192 for holding a biasing element in the form of a compressed coil spring 194 (or any other suitable biasing element). FIG. 26 also illustrates that at the distal end of the chamber 192, the outer shield 189 includes a groove 196 for engaging the distal end of the spring 194.

The outer shield 189 includes a stop 198 that engages with a tapered edge 200 of the inner shield 190 to create a jam 202 with the fluid connector 126, thereby selectively maintaining the inner shield 190 in a substantially fixed position relative to the outer shield 189 despite the bias of the spring 194. That is, the potential energy stored in the pre-compressed spring 194 is less than the static friction formed between the stop 198, the tapered edge 200, and the jam 202 to keep the inner shield 190 in a substantially fixed position after assembly of the needle shield device 188.

Unlike the previously-described embodiments, in this embodiment, the fluid connector 126 is connected to the base 102 while the introducer needle 110 is installed in the catheter 108, that is, while the assembly is ready for insertion into a patient's skin. Thus, the fluid connector also has a pierceable septum 203 to maintain the integrity and sterility of the fluid path once the introducer needle 110 is removed. The introducer needle 110 is omitted from FIGS. 26-28 and 31 for clarity.

Figure 27:
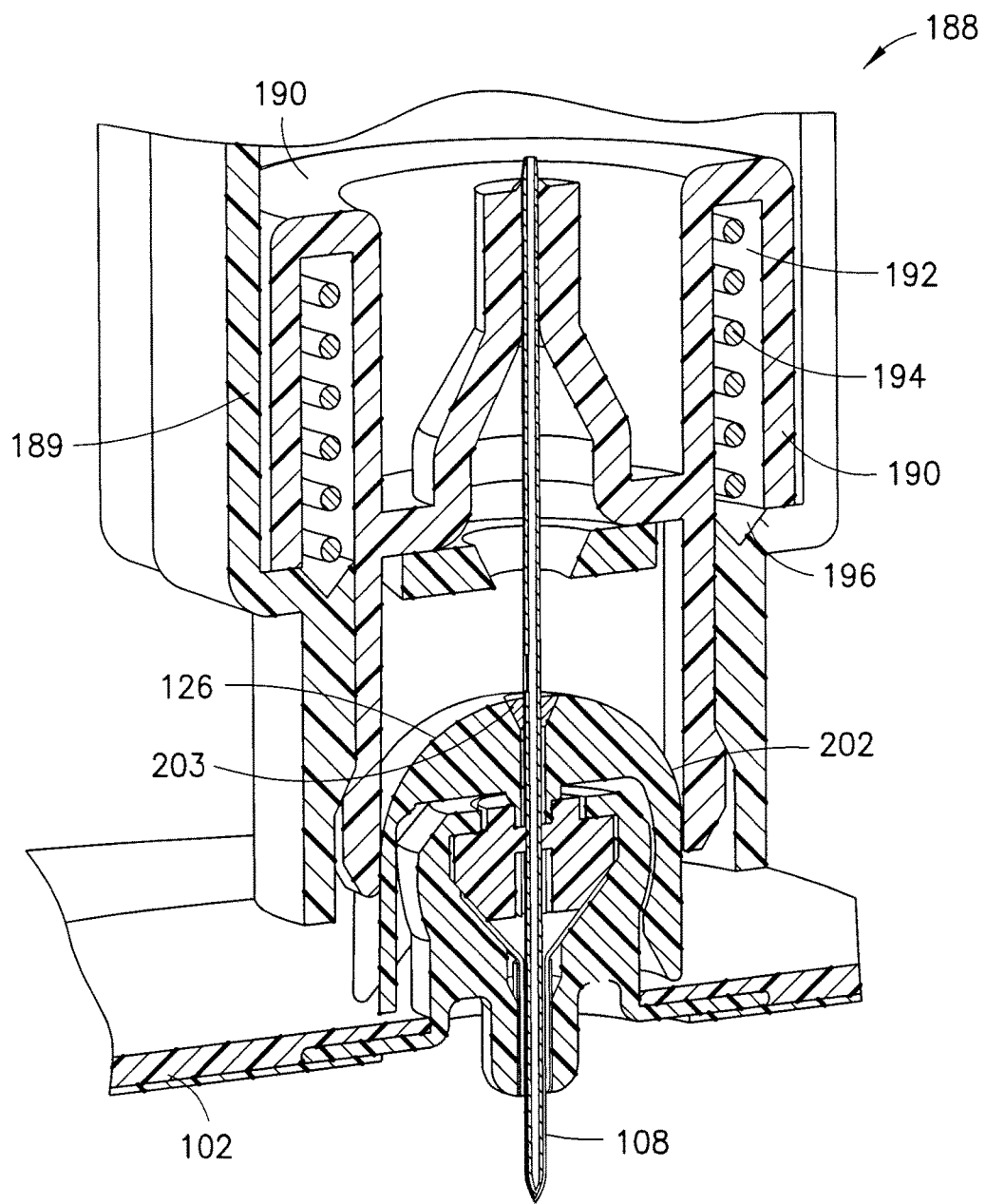
FIGS. 27-31 are additional perspective cross-sectional views illustrating the operation of the needle shield device of FIG. 25.
Figure 28:
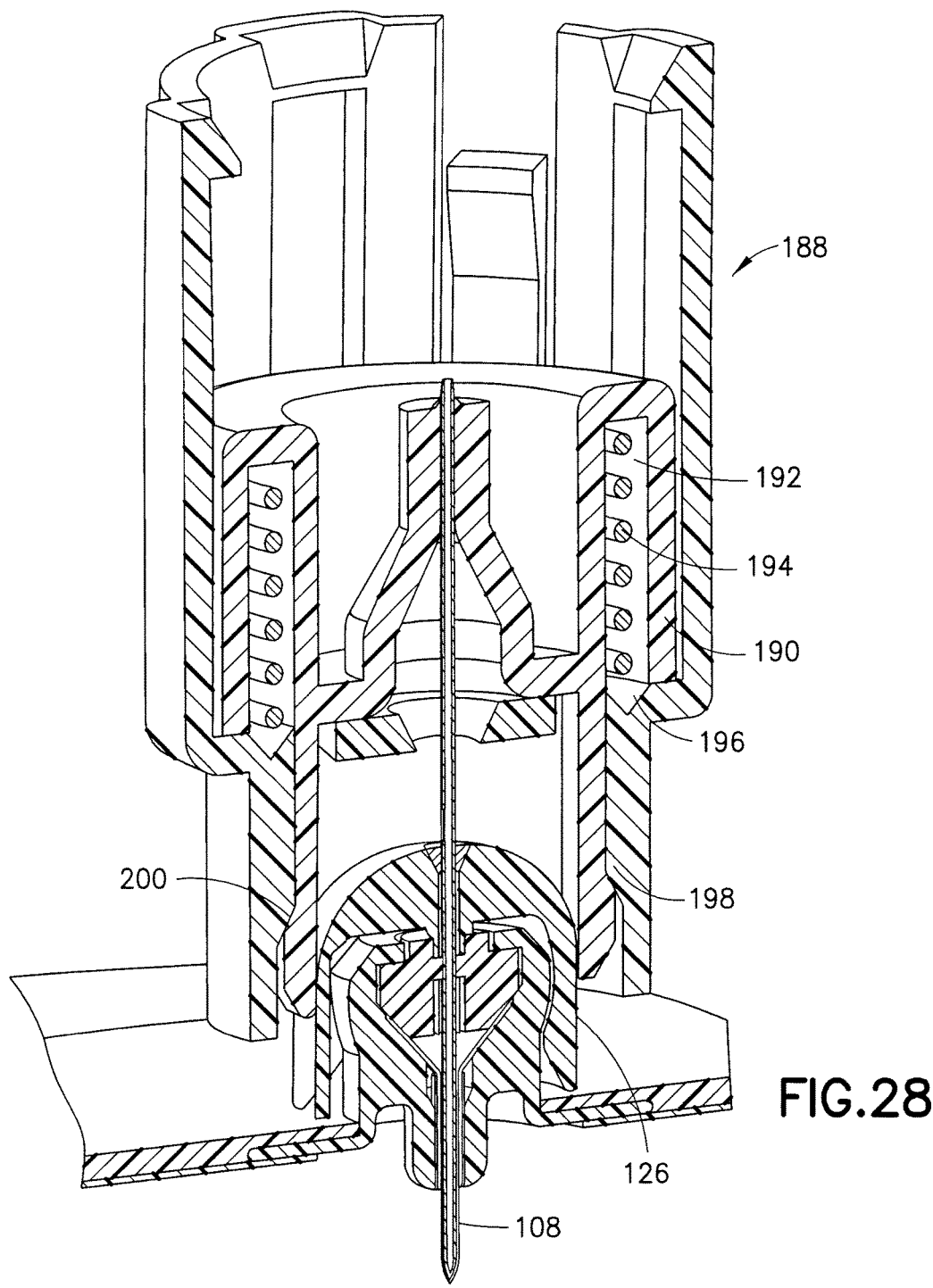
Figure 29:
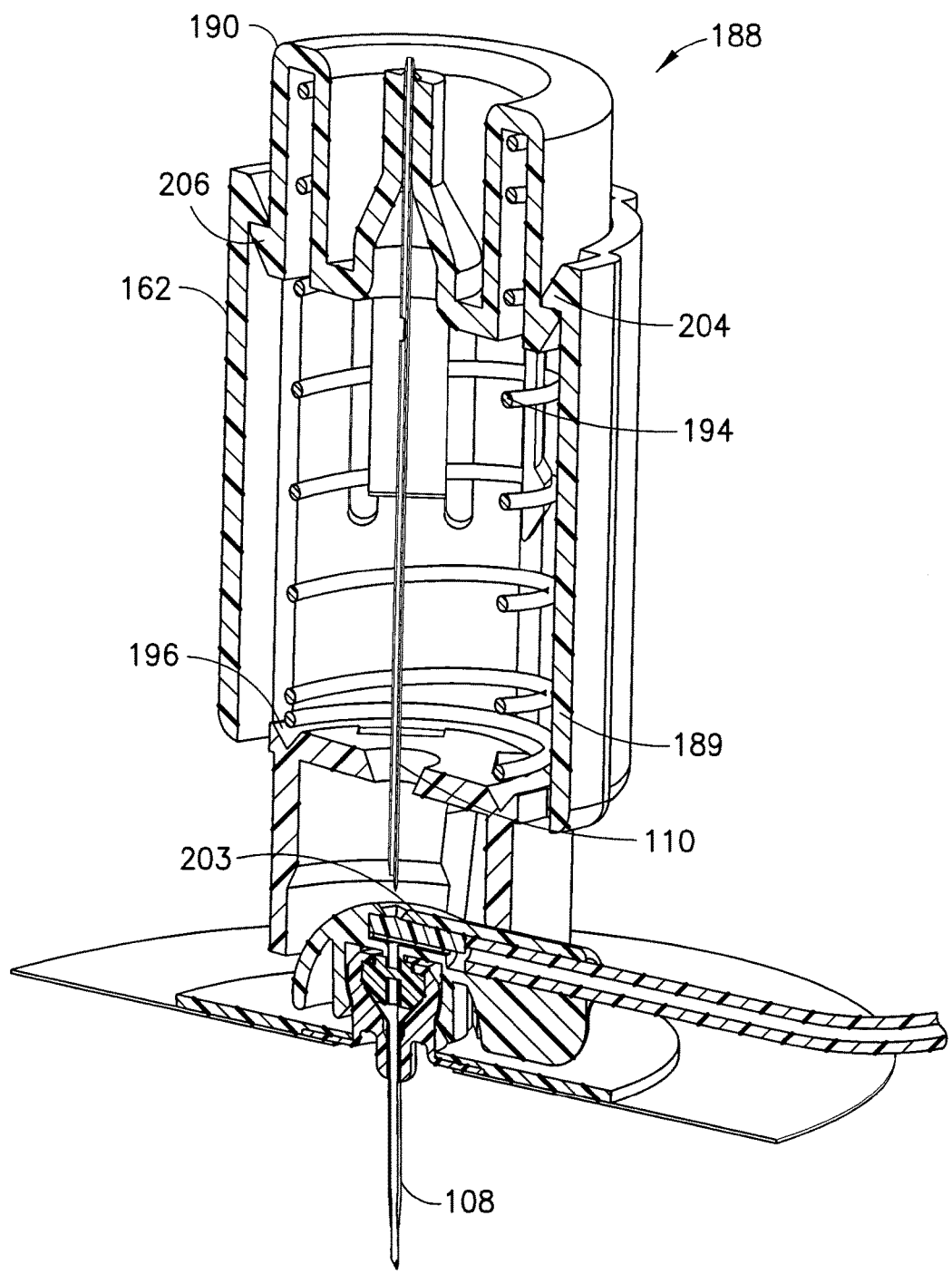

FIGS. 27-30 are exploded views of the needle shield device 188 that illustrate the removal of the introducer needle 110 from the user. FIG. 27 illustrates the needle shield device 188 being pulled away from the base 102 to begin removal of the introducer needle 110. The additional force applied by the user to the outer shield 189 and the potential energy stored in the spring 194 exceed the static friction formed by the stop 198, the tapered edge 200, and the jam 202, thereby causing the needle shield device 188 to displace axially and disengage from the fluid connector 126 and disengage the jam 202 under the force of the user and the spring 194. FIG. 28 illustrates the state during removal in which the inner shield 190 is no longer in contact with the fluid connector 126, thereby fully disengaging the jam 202. In one embodiment, the potential energy stored in the spring 194 exceeds the force required to move the stop 198 past the tapered edge 200 when the jam 202 is removed, as illustrated in FIG. 29, thereby causing the inner shield 190 to displace in the axial direction of the introducer needle 110 after disengaging the jam 202.

Figure 30:
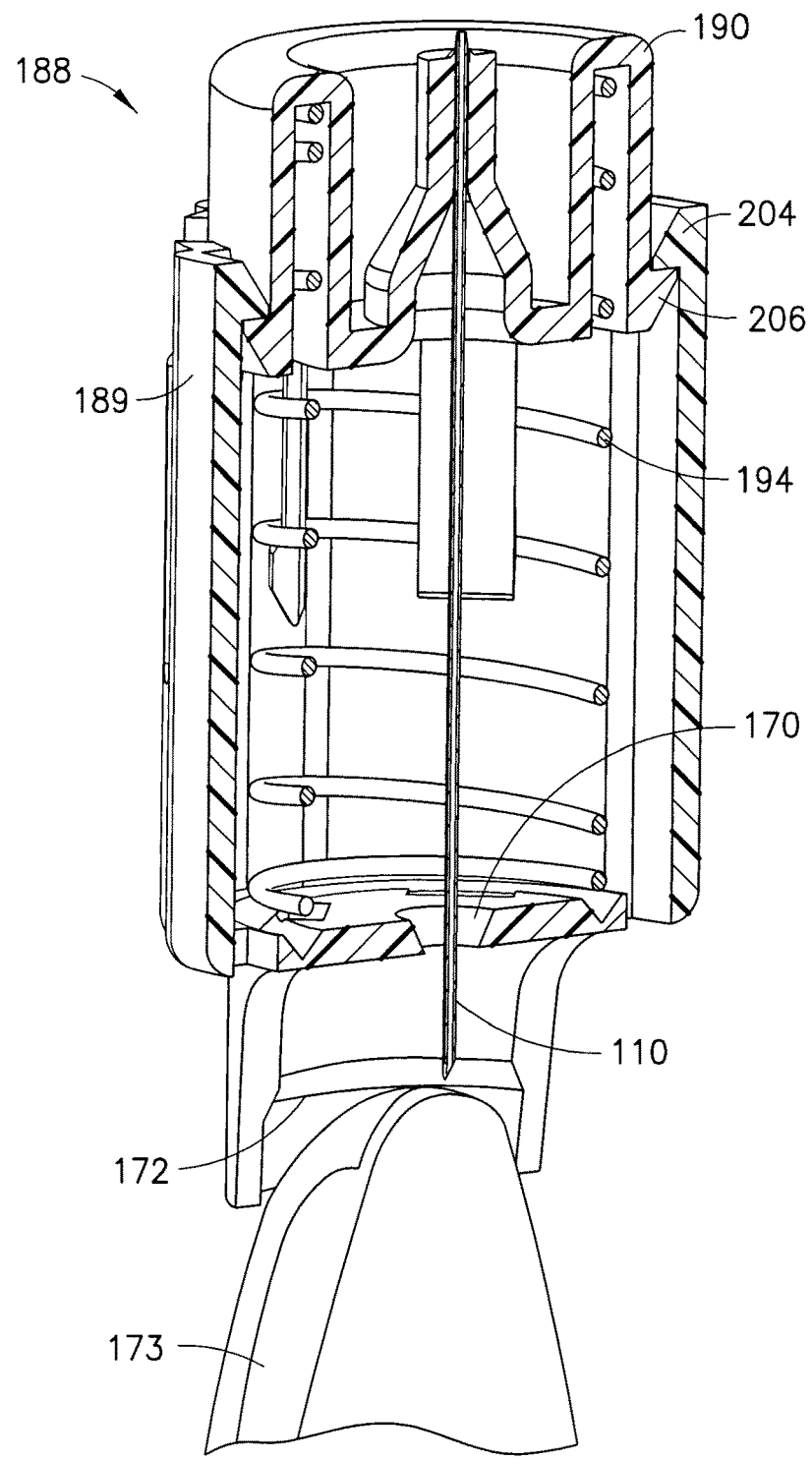

FIG. 30 illustrates the state in which the inner shield 190 has fully displaced and an edge or catch 204 of the outer shield 162 engages with an edge or catch 206 of the inner shield 190. In such an exemplary embodiment, the spring 194 may remain biased to keep the edges 204 and 206 engaged. FIG. 30 also illustrates that the introducer needle 110 extends through an opening 170 into the shield well 172 of the inner shield 190. The well 172 surrounds the concealed introducer needle 110 so that an average finger 173 will not fit through the opening of the shield well 172 and contact the concealed introducer needle 110. In this embodiment, the needle shield device 188 automatically releases the inner shield 190 during withdrawal of the introducer needle 110 in a single motion, and provides the user with a mechanism to protect from an accidental needle stick.

Figure 31:
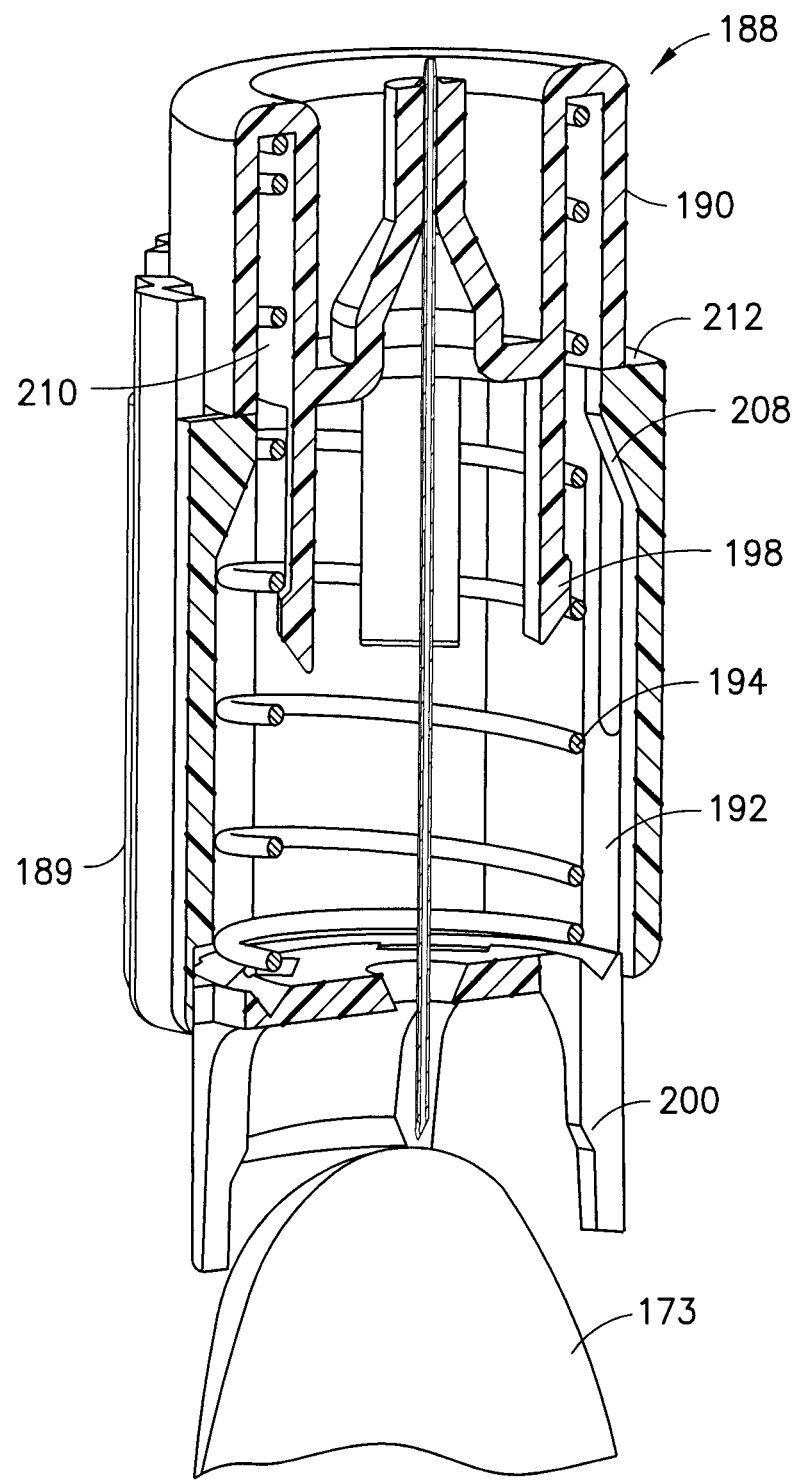

FIG. 31 illustrates an alternative embodiment of the needle shield device 188 in which the outer shield 189 includes cantilevered, tapered edge beams 208 that are circumferentially interposed between the edges 204. The edge beams 208 are biased radially by snap latches 210 of the inner shield 190 when the introducer needle 110 is in an exposed position. As the spring 194 displaces the inner shield 190 upward, the snap latches 210 move past the distal ends of the tapered edge beams 208, and the edge beams 208 move radially inward and latch and an edges 212 of the tapered edge beams 210 latch with the snap latches 210, thereby preventing movement of the inner shield 190 in the axial direction of the introducer needle 110. In other words, once fully-extended, the interaction between the edges 204 and 206 prevent the inner shield 190 from moving upward and the interaction between the edge beams 208 and the snap latches 210 prevent the inner shield from moving downward, thus locking the introducer needle in a covered position, and preventing exposure of the introducer needle 110.

Figure 32:
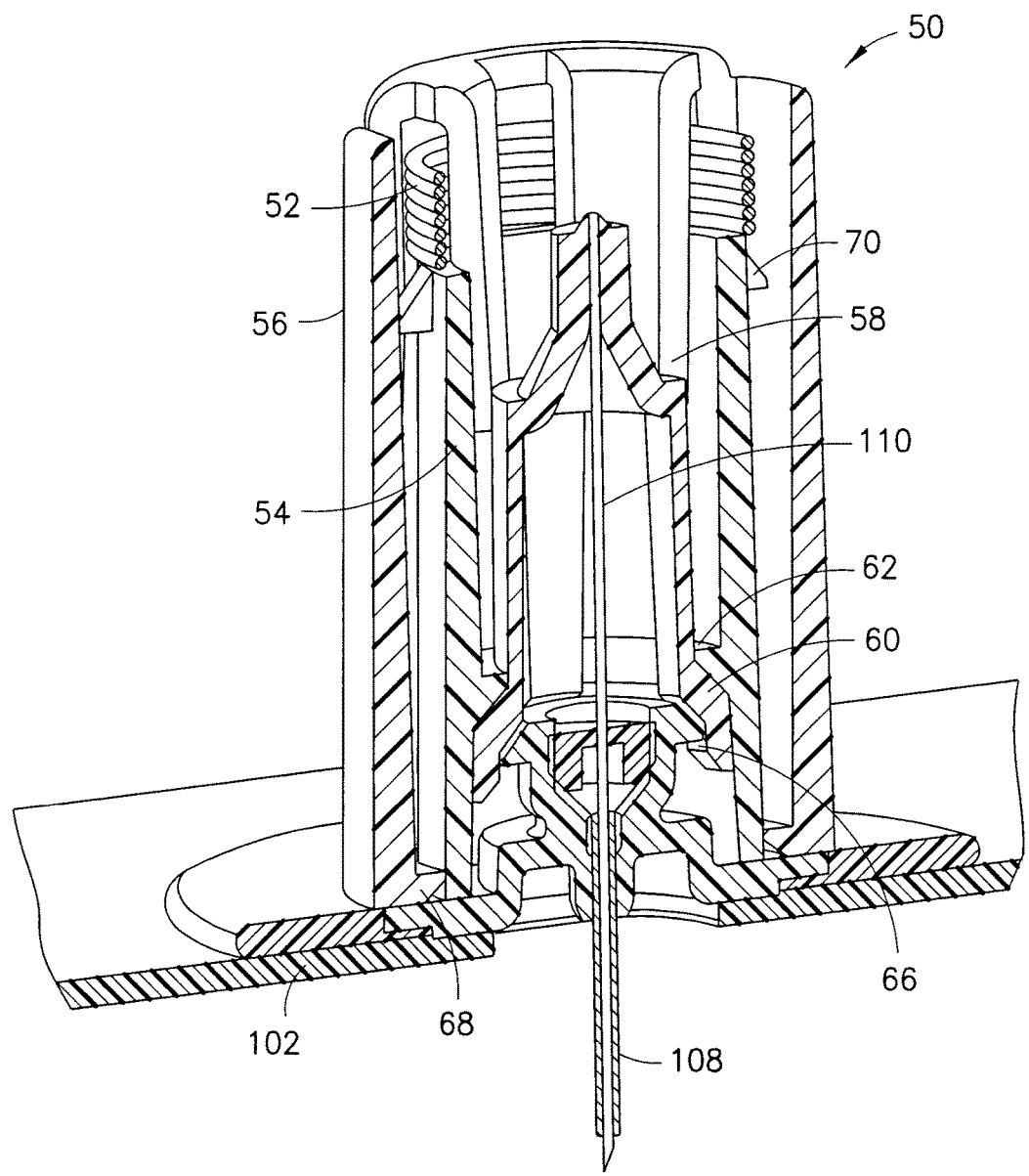
FIGS. 32-34 are perspective cross-sectional views of a needle shield device in accordance with an exemplary embodiment of the present invention.
Figures 33, 34:
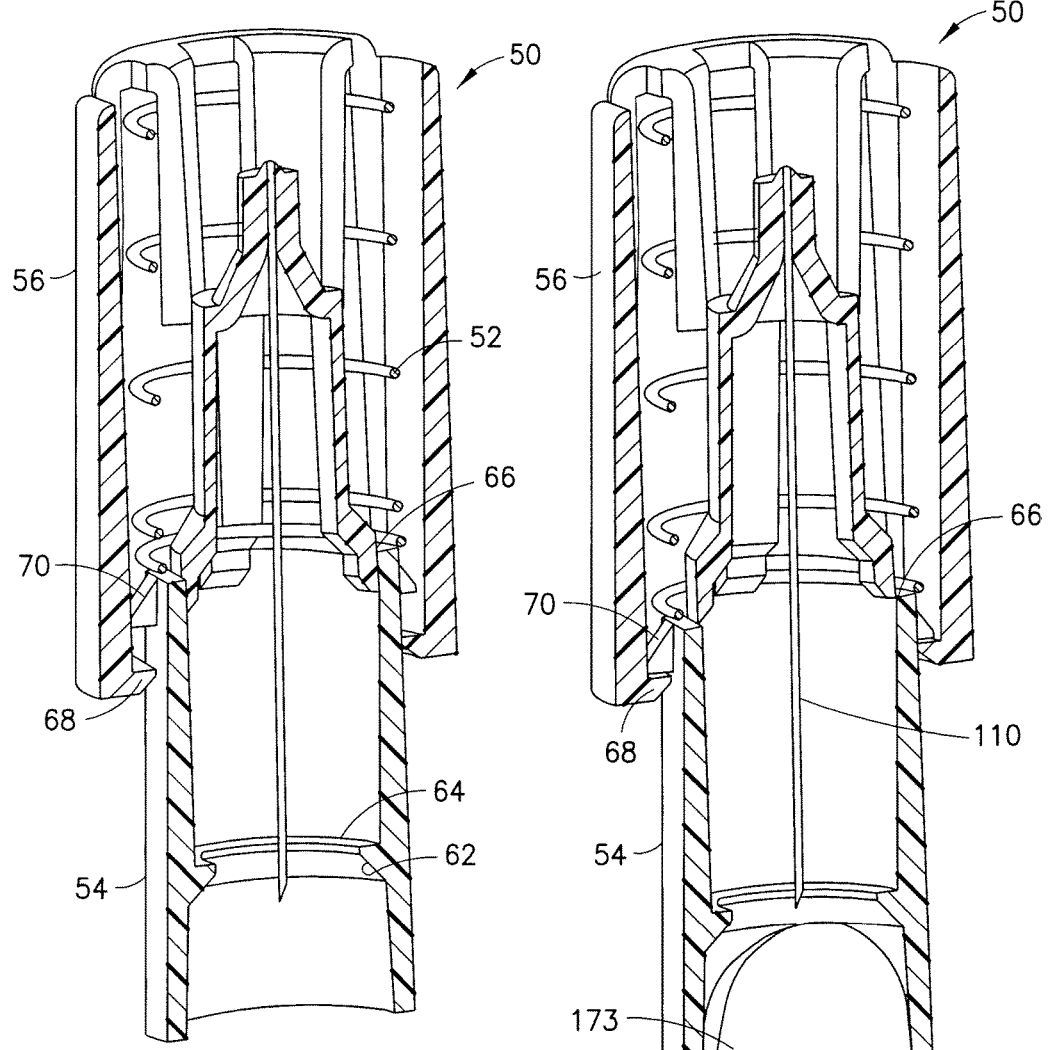

The embodiment of FIGS. 32-34 is similar to the embodiment of FIGS. 25-31, but differs in several respects. For example, rather than connecting to the fluid connector, the needle shield device 50 connects directly to the base 102. Additionally, rather than a pre-compressed spring pushing the inner shield upward relative to the outer shield, the pre-compressed spring 52 pushes the inner shield 54 downward relative to the outer shield 56 after the needle shield device disengages from the base 102. In more detail, the outer shield 56 has an inner portion 58 (to which the introducer needle 110 is connected) that includes a stop 60 at a distal end thereof. When the needle shield device 50 is connected with the base 102, the introducer needle 110 is in an extended position disposed in the catheter 108. In this position, the stop 60 engages a tapered edge 62 of a rim 64 of the inner shield 54 to create a jam 66 with the base 102, thereby selectively maintaining the inner shield 54 in a substantially fixed position relative to the outer shield 56 despite the bias of the spring 52. That is, the potential energy stored in the pre-biased spring 52 is less than the static friction formed between the stop 60, the tapered edge 62, and the jam 66 to keep the inner shield 54 in a substantially fixed position after assembly of the needle shield device 50.

As the needle shield device 50 is pulled away from the base 102 and the jam 66 is disengaged, the force of the spring 52 drives the inner shield 54 downward relative to the outer shield 56. As shown in FIG. 33, which illustrates a state just prior to the inner shield 54 being fully extended and locked out, the jam 66 slides along an internal surface of the inner shield. Once fully extended, as shown in FIG. 34, an edge or catch 68 of the outer shield 56 engages an edge or catch 70 of the inner shield 54 to prevent the inner shield 54 from displacing further distally relative to the outer shield 56. Additionally, the jam 66 engages a proximal surface of the inner shield 54 to prevent the inner shield 54 from displacing proximally relative to the outer shield 56. Thus, the introducer needle 110 is shielded from an average finger 173.

Relative to the embodiment of FIGS. 25-31, the embodiment of 32-34 is simpler to mold, and does not require radial orientation during assembly.

Figure 35:
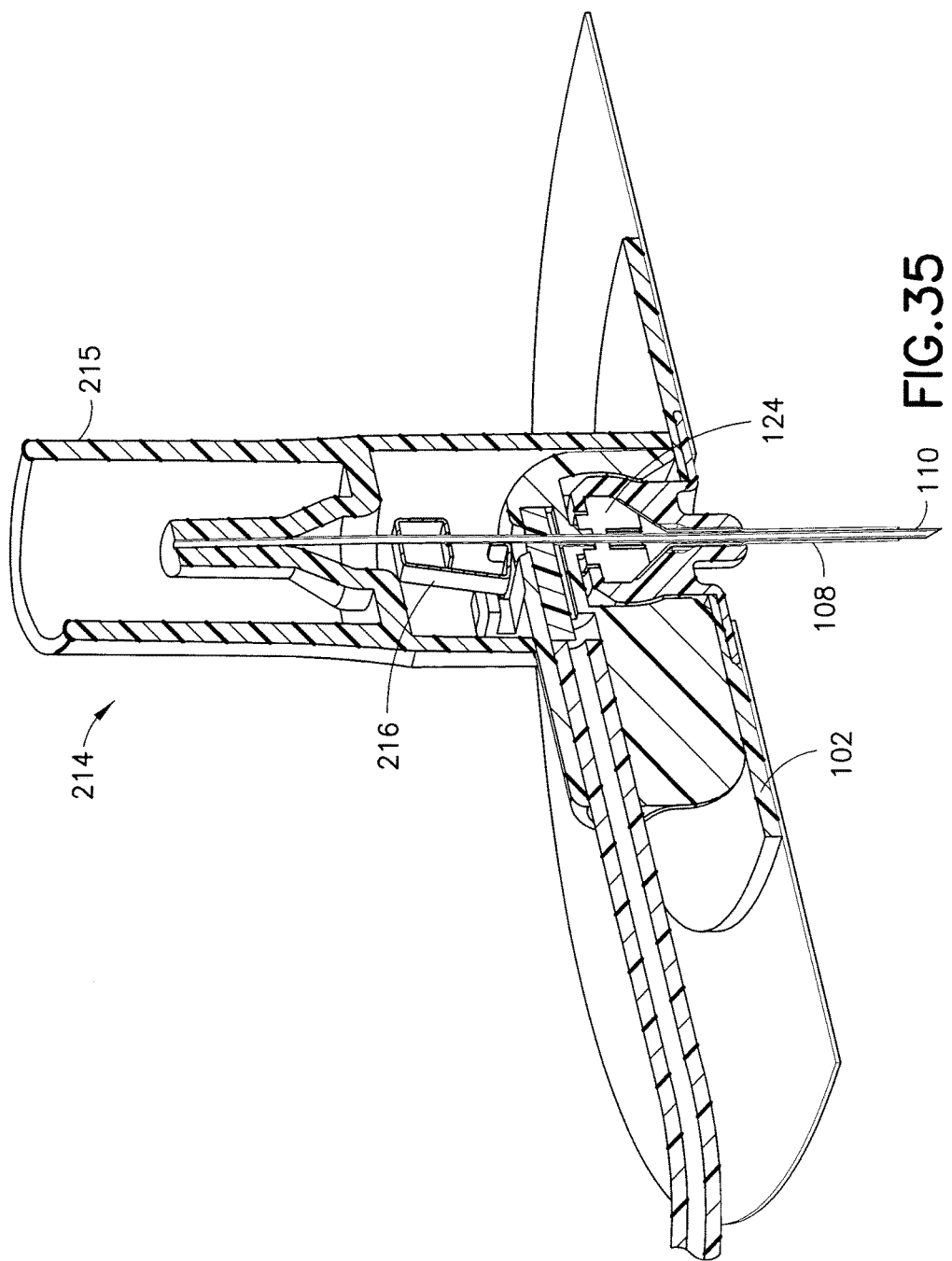
FIG. 35 is a perspective cross-sectional view of a needle shield device in accordance with an exemplary embodiment of the present invention.
Figure 36:
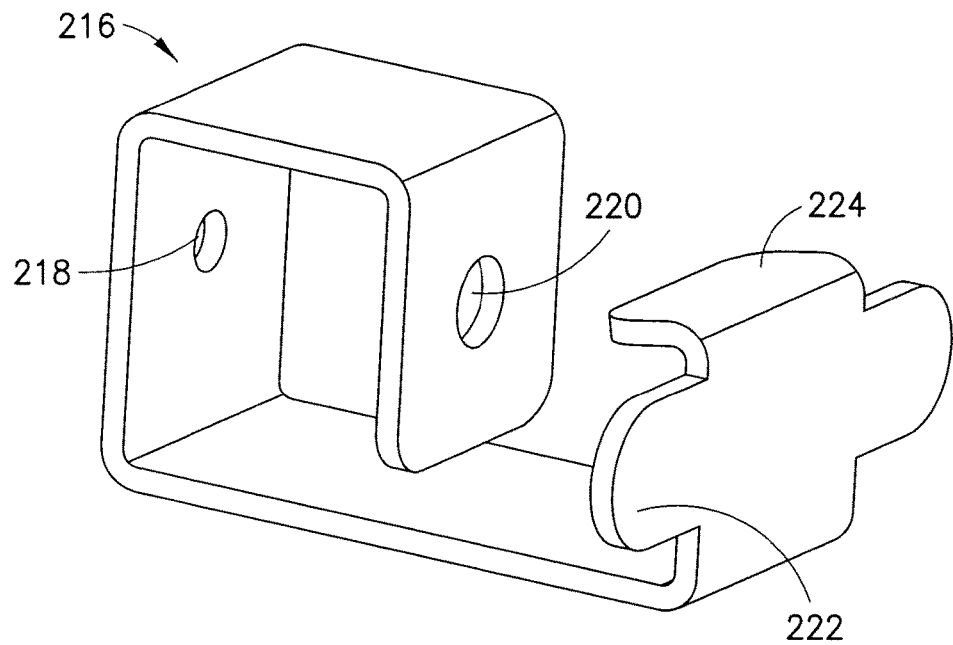
FIG. 36 is a perspective view of a bias spring of the needle shield device of FIG. 35.
Figure 37:
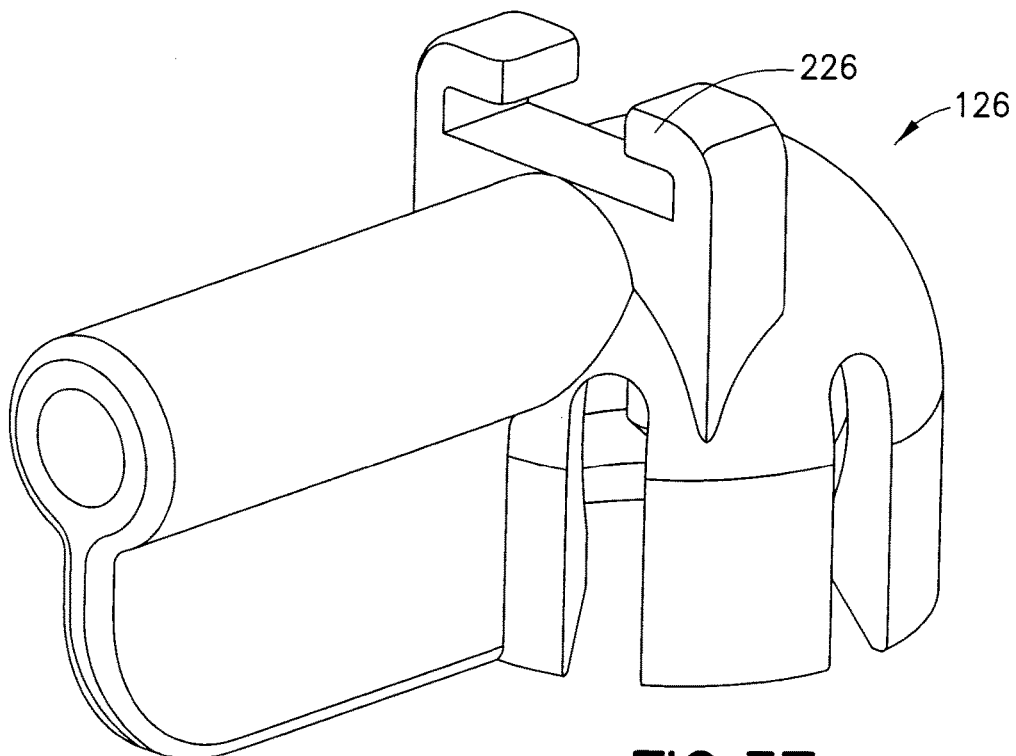
FIG. 37 is a perspective view of a fluid connector used with the needle shield device of FIG. 35.

FIG. 35 is a cross-sectional view of another embodiment of a needle shield device 214 fully engaged with the base 102, piercing the septum 124 and catheter with the introducer needle 110 and ready for placement on the skin. The needle shield device 214 includes a spring element or metal spring clip 216 to protect or shield the tip of the introducer needle 110 after withdrawal from the user's skin. FIG. 36 is a perspective view of the spring clip 216 which has a retention hole 218 for retaining the introducer needle 110 and a large hole 220 for passing a bump on the introducer needle 110 (best shown in FIGS. 39 and 40). The spring clip 216 also includes latch tabs 222 and a trigger 224 for protecting the tip of the introducer needle 110. FIG. 37 is a perspective view of the fluid connector 126 that includes hub latches 226 for engaging the latch tabs 222 and maintaining the spring clip 216 in a substantially fixed position prior to withdrawal of the introducer needle 110 from the base 102.

Figure 38:
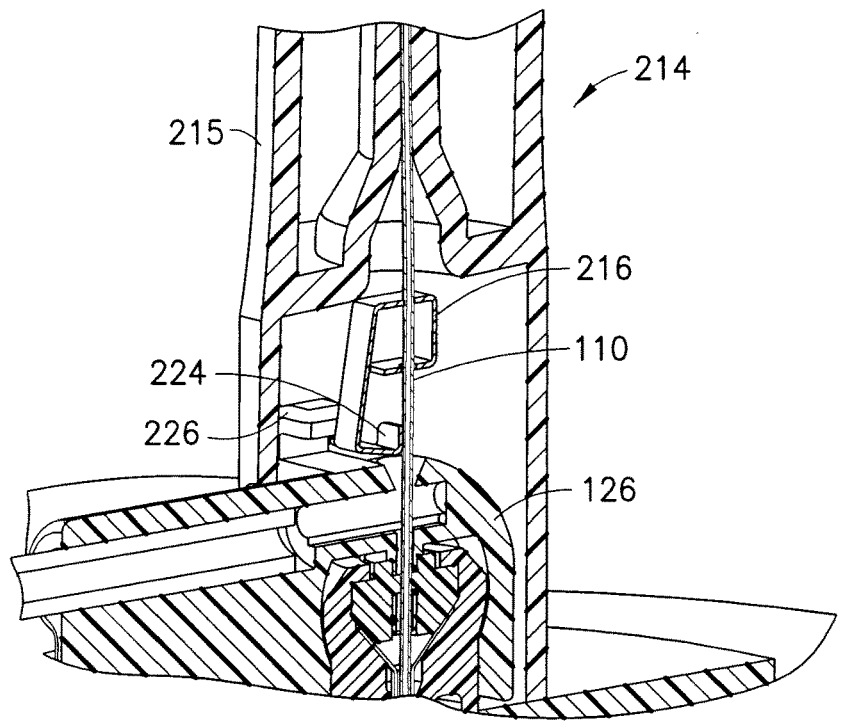
FIGS. 38-40 are perspective cross-sectional views illustrating the operation of the needle shield device of FIG. 35.
Figure 39:
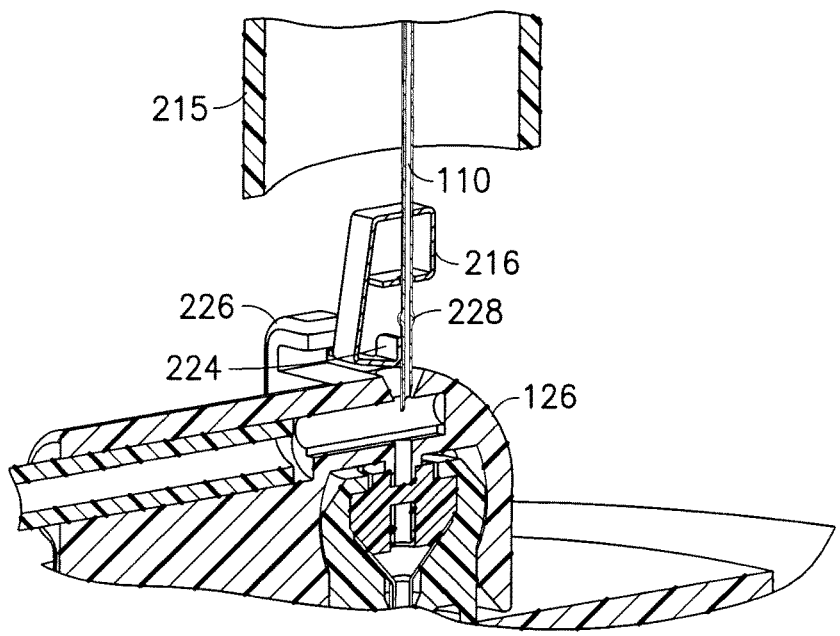
Figure 40:
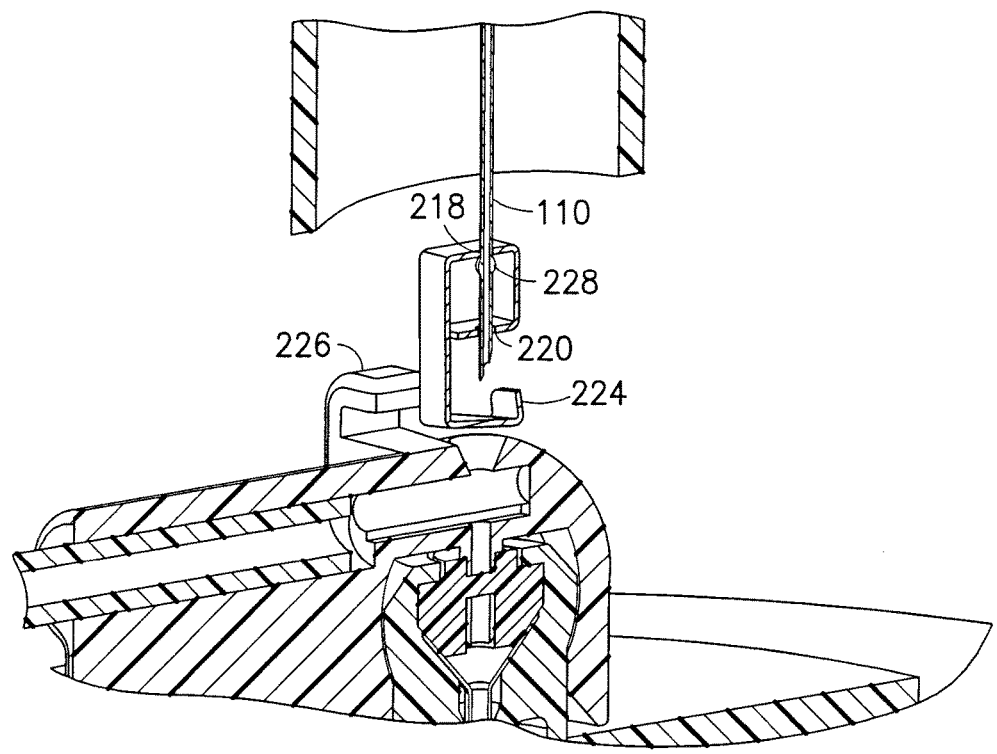

FIGS. 38-40 are cross-sectional views that illustrate the operation of the needle shield device 214 using the spring clip 216. Initially, as shown in FIG. 38, the spring clip 216 is biased by the introducer needle 110 via the trigger 224 so that the latch tabs 222 are retained by the hub latches 226 disposed on the fluid connector 126, thereby substantially retaining the spring clip 216 in the initial position.

As the introducer needle 110 is withdrawn from the fluid connector 126 and the base 102 along with the needle hub or handle 215, as shown in FIG. 40, the introducer needle 110 rides along the trigger 224. In the embodiment of FIG. 39, the introducer needle 110 includes a bump 228 disposed near its distal tip. As the bump 228 passes the trigger 224, the spring clip 216 experiences additional bias due to the bump 228.

FIG. 40 illustrates the state in which the spring clip becomes unbiased as the introducer needle's tip is retracted past the trigger 224. In response to the unbiasing of the spring clip 216, the latch tabs 222, which were prevented from displacing axially by the hub latches, displace forward, thereby unlatching from the hub latches 226 and releasing the spring clip 216 from connection with the hub latches 226 of the fluid connector 126. FIG. 40 further illustrates that, as the introducer needle 110 is retracted, the bump 228 passes through the large hole 220 but does not pass through the retainer hole 218 of the spring clip 216. Further, after becoming unbiased, the spring clip 216 is positioned such that the trigger 224 covers the tip of the introducer needle 110. In this embodiment, the needle shield device 214 automatically releases the spring clip 216 during withdrawal of the introducer needle 110 in a single motion and provides the user with a mechanism to protect from an accidental needle stick.

Figure 41:
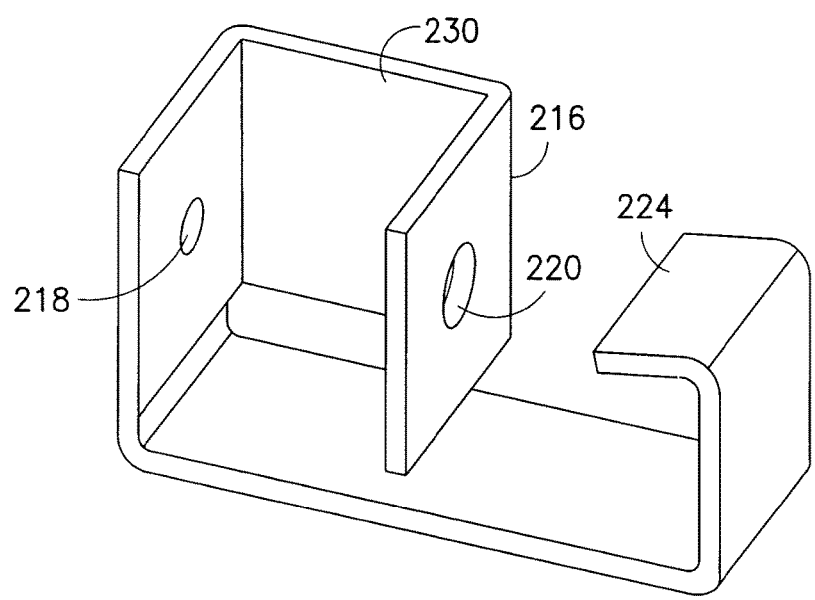
FIG. 41 is a perspective view of an alternative bias spring.

FIG. 41 illustrates an alternative embodiment of the spring clip 216 having a transverse portion 230. The transverse portion 230 reduces the elasticity of the spring clip 216, thereby increasing the bias strength of the spring clip 216.

Figure 42:
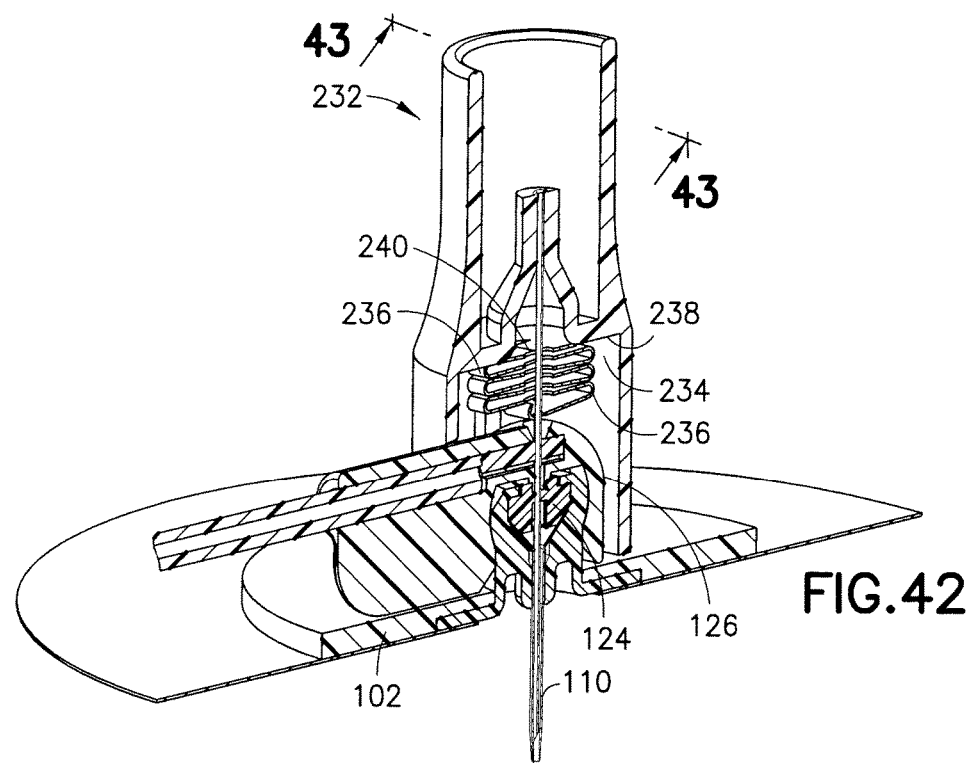
FIG. 42 is a perspective cross-sectional view of a needle shield device in accordance with an exemplary embodiment of the present invention.
Figure 43:
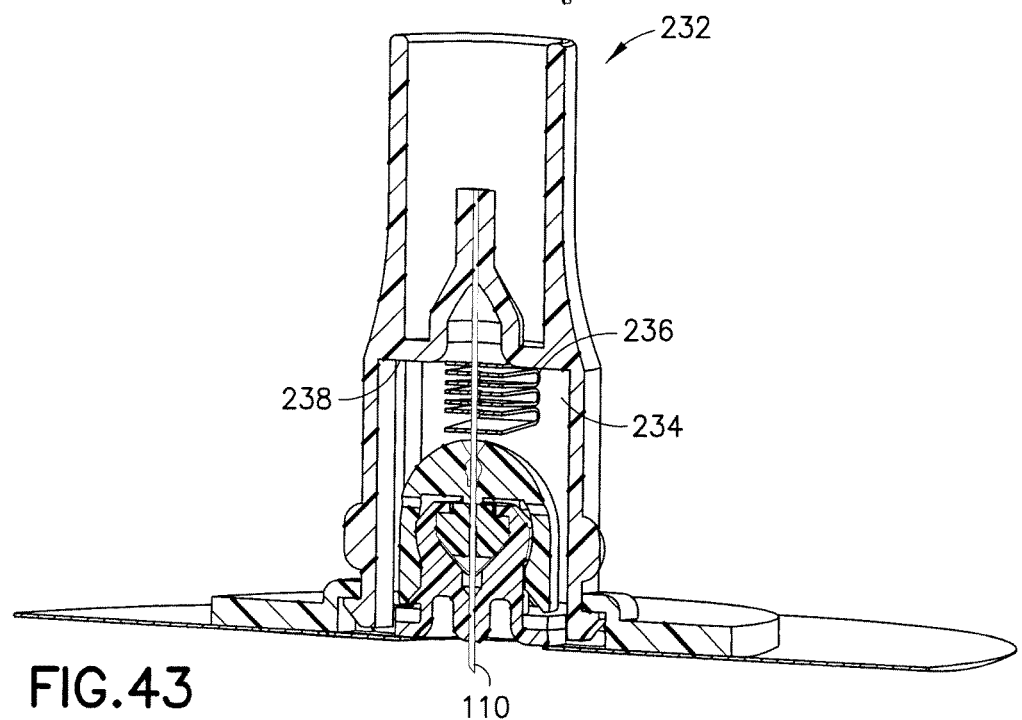
FIG. 43 is a perspective cross-sectional view of the needle shield device of FIG. 42, taken along line 43-43 of FIG. 42.

FIG. 42 is a cross-sectional view of another embodiment of a needle shield device 232 fully engaged with the fluid connector 126 and the base 102, piercing the septum 124 and catheter with the introducer needle 110 and ready for placement on the skin. FIG. 43 is another cross-sectional view of the needle shield device 232 taken at 90 degrees with respect to FIG. 42. The needle shield device 232 includes a cavity 234 over the fluid connector 126 for housing a spring element or biased spring 236. In the example of FIGS. 42 and 43, the spring 236 is biased in contact with the fluid connector 126 and a surface 238 at the proximal end of the cavity 234.

Figure 44:
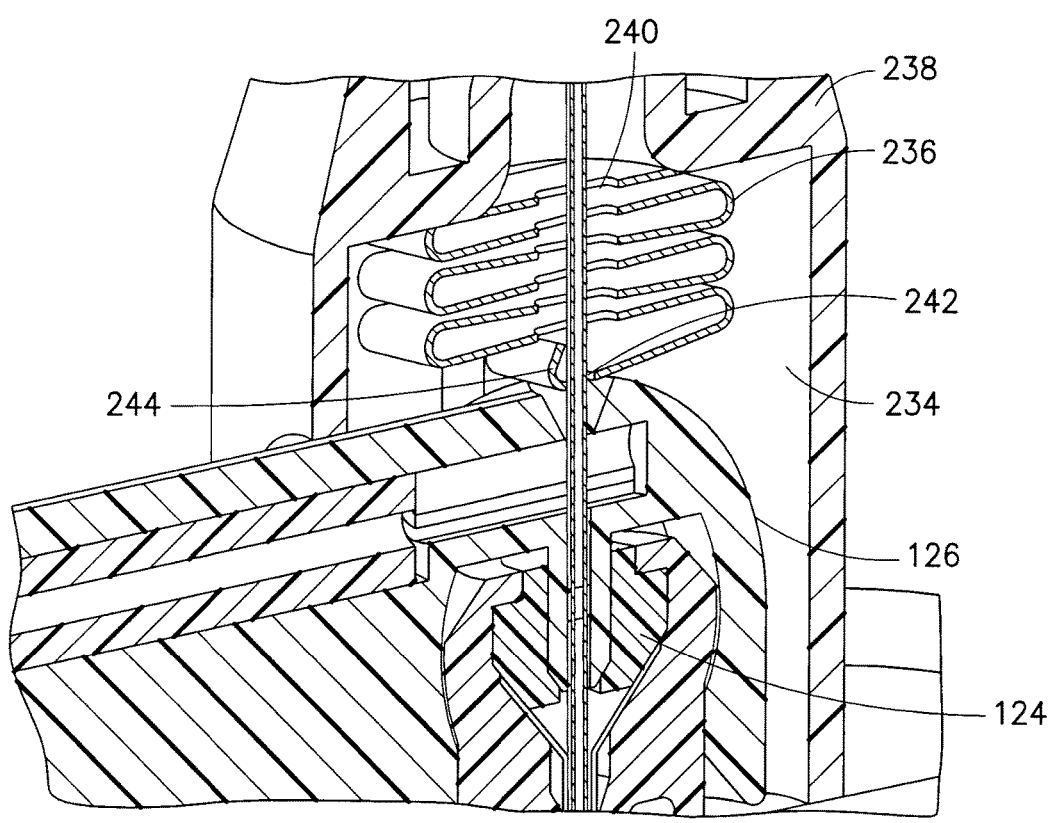
FIG. 44 is partial, perspective cross-sectional view of the needle shield device of FIG. 42 illustrating spring slots.

FIG. 44 is a cross-sectional view of the spring 232 showing that it includes slotted holes 240 for the introducer needle 110 to pass through. The slotted holes 240 are axially aligned with the septum 124. The spring 236 also includes a small hole 242 and a tip pocket 244 at the distal end of the spring 236, which is in contact with the fluid connector 126.

Figure 45:
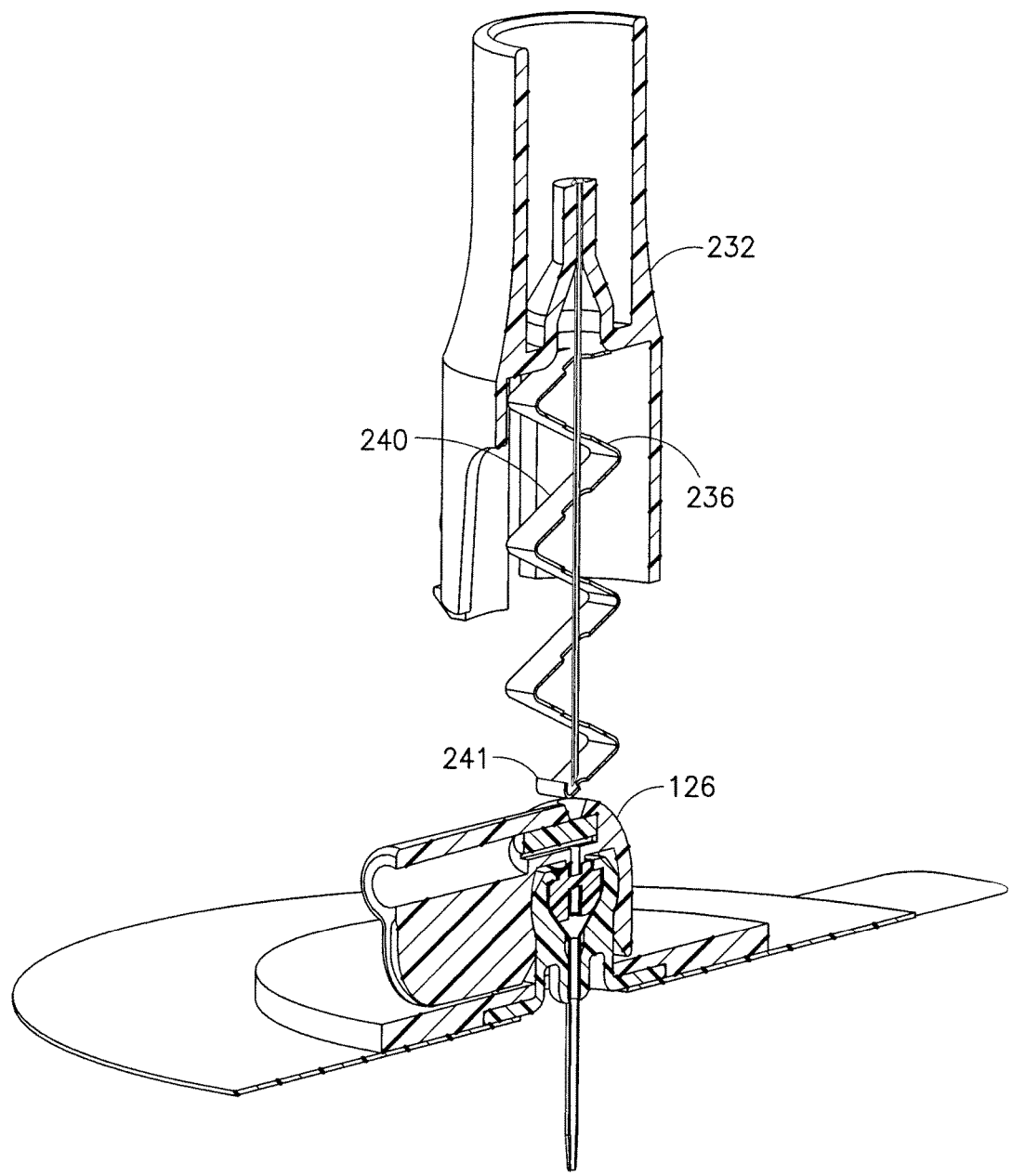
FIGS. 45 and 46 are perspective cross-sectional views illustrating operation of the needle shield device of FIG. 42.
Figure 46:
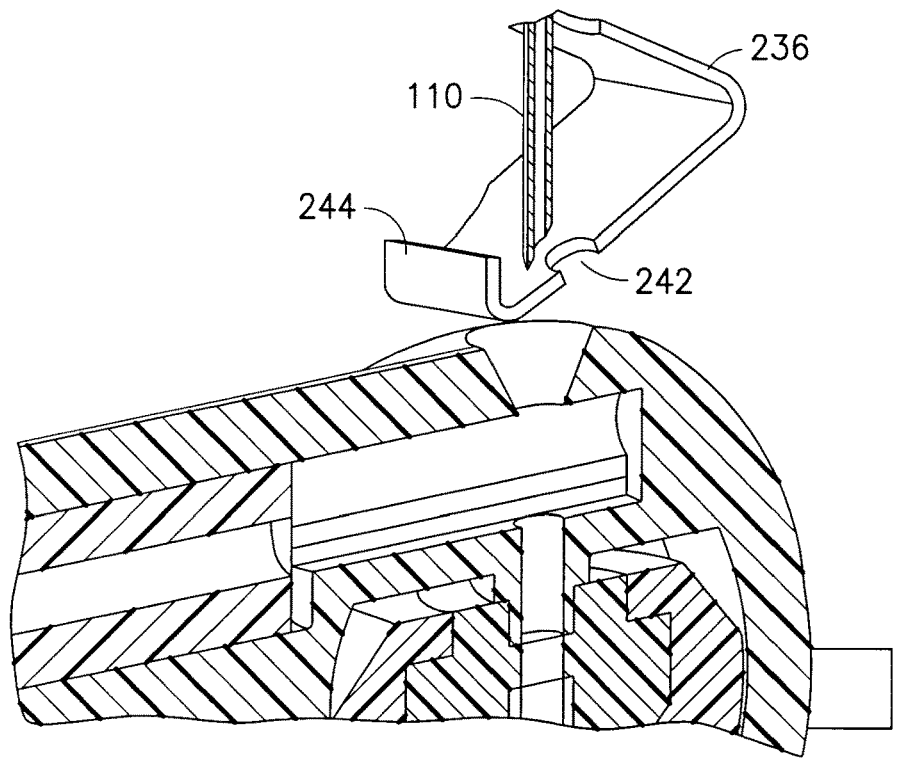

FIGS. 45 and 46 illustrate the removal of the needle shield device 232. In FIG. 45, when the needle shield device 232 is retracted to withdraw the introducer needle 110 from the fluid connector 126 and the base 102, the biased spring 236 unbiases and expands along the axis of the introducer needle 110. According to one embodiment, the slotted holes 240 are longitudinal slots aligned to accommodate the introducer needle 110 as the spring 236 expands.

FIG. 46 illustrates that the needle shield device 232 is fully retracted and the spring 236 extends over the tip of the introducer needle 110, so that the tip is disposed in the tip pocket 244. Further, according to one embodiment, the small hole 242 is biased to one side of the spring 236 so that when the tip of the introducer needle 110 passes through the hole 242, the spring 244 transversely unbiases so that the hole 242 is not axially aligned with the introducer needle 110. That is, a barrier is formed over the tip of the introducer needle 110 when the spring 236 unbiases and substantially covers the introducer needle 110.

According to one embodiment, the spring 236 can be a compression spring (for example, a spiral or coil spring) or a tapered compression spring to provide the force necessary to shield the tip of the introducer needle 110. In such an embodiment, a tip shield can be disposed at the distal end of the spring to cover the tip of the introducer needle 110 after expansion of the spring.

The needle shield device 232 automatically releases the transverse barrier formed by the tip pocket 244 and hole 242 during retraction of the introducer needle 110 in a single motion and provides the user with a mechanism to protect the user from an accidental needle stick.

Figure 47:
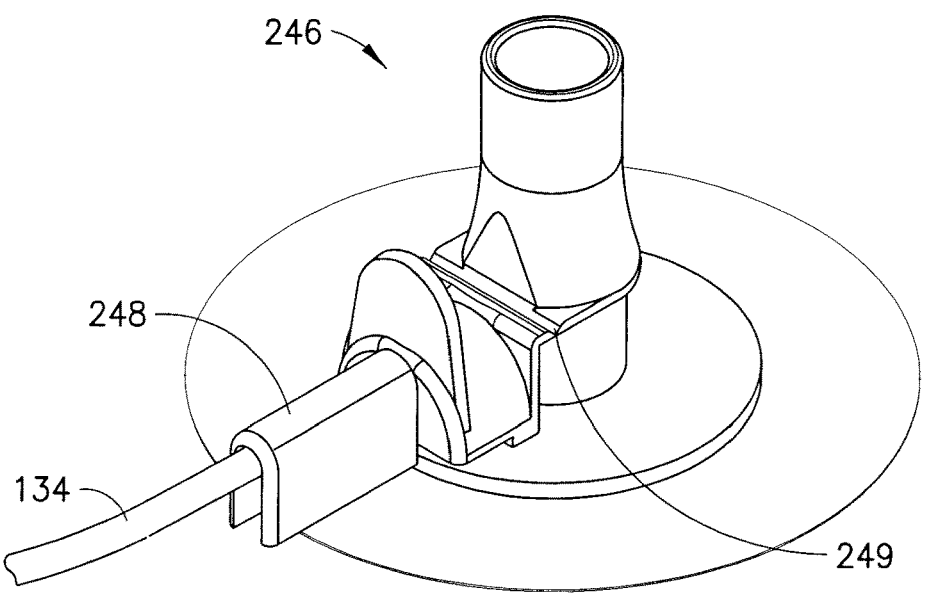
FIG. 47 is a perspective view of a needle shield device in accordance with an exemplary embodiment of the present invention.
Figure 48:
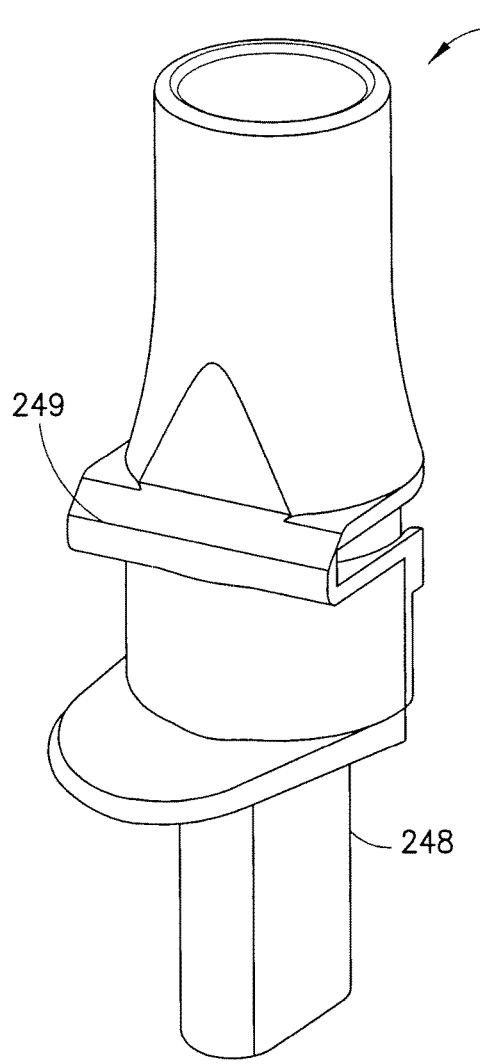
FIGS. 48 and 49 illustrate the needle shield device of FIG. 47 after deployment of a needle shield.
Figure 49:
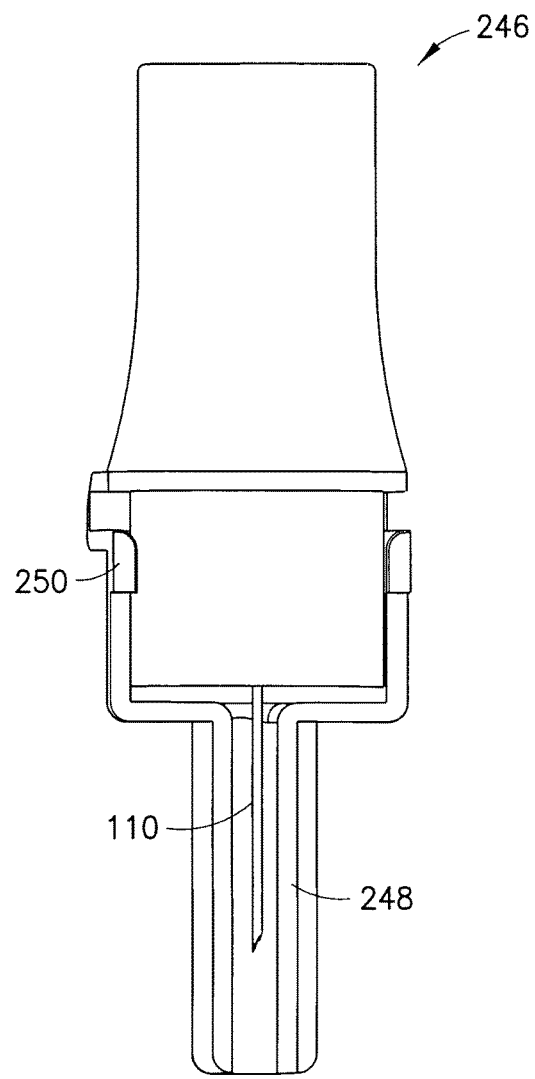

FIGS. 47-52 illustrate another exemplary embodiment of a needle shield device 246. FIG. 47 is a perspective view of the needle shield device 246 with a shield 248 that is disposed over the extension tubing 134 prior to insertion. The shield 248 includes a hinge 249 that may be formed by molding the needle shield device 246 as a single piece. In an alternative exemplary embodiment, the hinge 249 may be molded separately and fixed to the needle shield device 246. The shield 248 generally has a U-shaped profile and is deployed after removal from the fluid connector 126 and/or base 102 by rotating the shield 248 about the hinge 249. FIGS. 48 and 49 illustrate the shield 248 after deployment. The shield 248 includes latches 250 on an inner surface to keep the shield 248 in a substantially fixed position after deployment.

FIG. 50 is a cross-sectional view of the needle shield device 246 and illustrates that the shield 248 has an inner cavity 252 that is press fit and latches with a base 254 of the needle shield device 246. According to one embodiment, the shield 248 latches to the base 254 without contacting or bending the needle 110. FIG. 51 is a cross-sectional view of the needle shield device 246 after deployment, and illustrates that the distal end of the shield 248 extends beyond the tip of the introducer needle 110. FIG. 52 is another cross-sectional view at 90 degrees with respect to FIG. 51 and illustrates that a gap 256 of the shield 248 is smaller than the average finger, to prevent an accidental needle stick.

Figure 53:
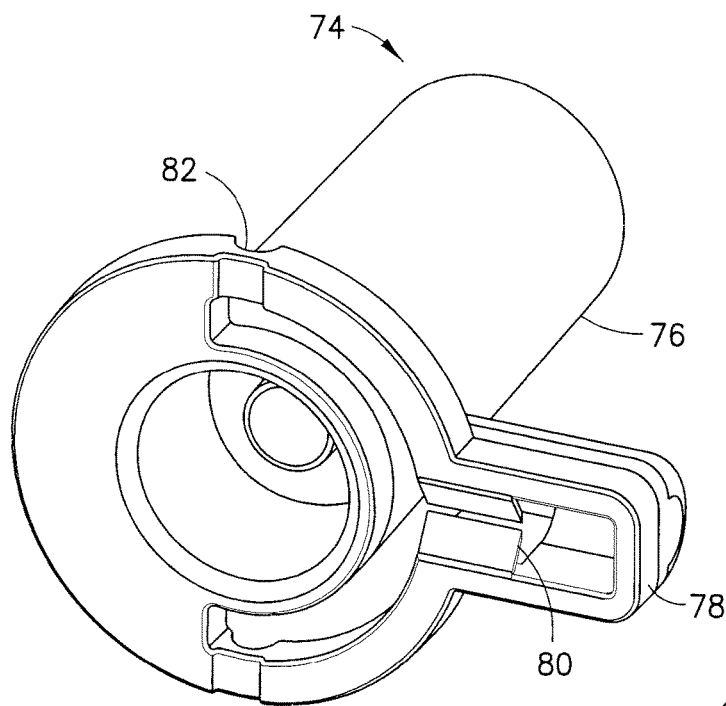
FIGS. 53 and 54 are perspective views of a needle shield device in accordance with an exemplary embodiment of the present invention.
Figure 54:
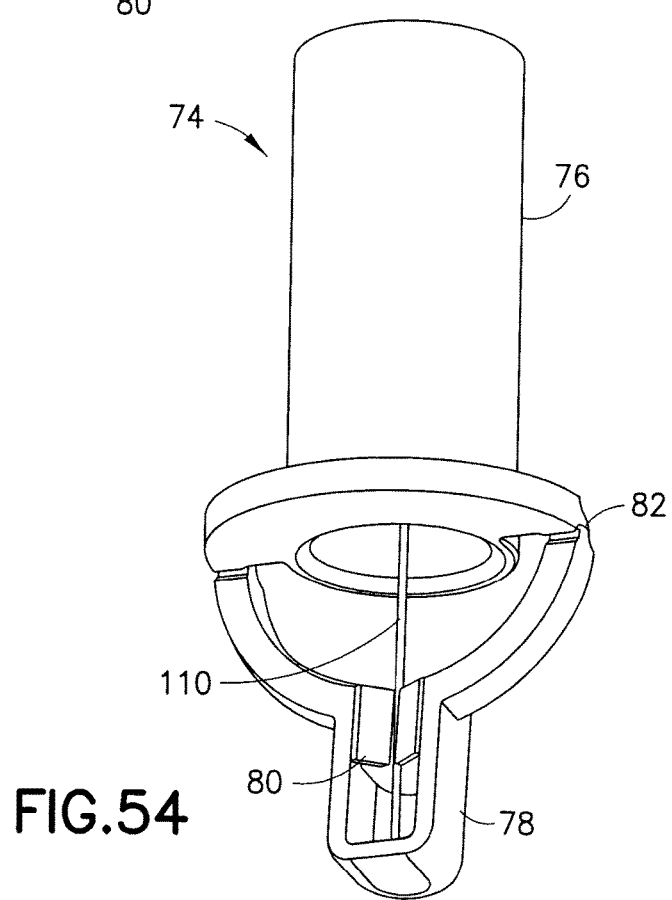

Conventional one-piece protective shields generally have more than a 90-degree rotation and may require the user to bend or break the needle. This requires extra force and/or extra manufacturing (e.g., a notch in the introducer needle to facilitate bending or breaking). Such conventional designs also result in a wider needle holder that is physically larger and more difficult to dispose of. The above-described exemplary embodiment is easier to manufacture by reducing manufacturing steps and also is easier to operate because the integrity of the introducer needle is maintained. Further, the above-described exemplary embodiment is physically smaller than conventional shields and is therefore easier to dispose of FIGS. 53 and 54 are perspective views of another embodiment of a needle shield device 74. The introducer needle 110 is omitted from FIG. 53 for clarity. The needle shield device 74 includes a needle hub 76 and a shield 78 rotatably connected to the needle hub 76 by a hinge 82, such as a living hinge. The shield 78 includes one or more cantilevered needle-engaging flaps 80. When the user rotates the shield 78 to enclose the introducer needle 110, as shown in FIG. 54, the flaps 80 are disposed to permit the flaps 80 to pass the introducer needle 110 in one direction, but prevent the shield from passing the introducer needle in the opposite direction thereafter. In other words, once the shield 78 is deployed to cover the shield, the flaps engage the introducer needle 110 to prevent the shield 78 from returning to its initial position.

Figure 55:
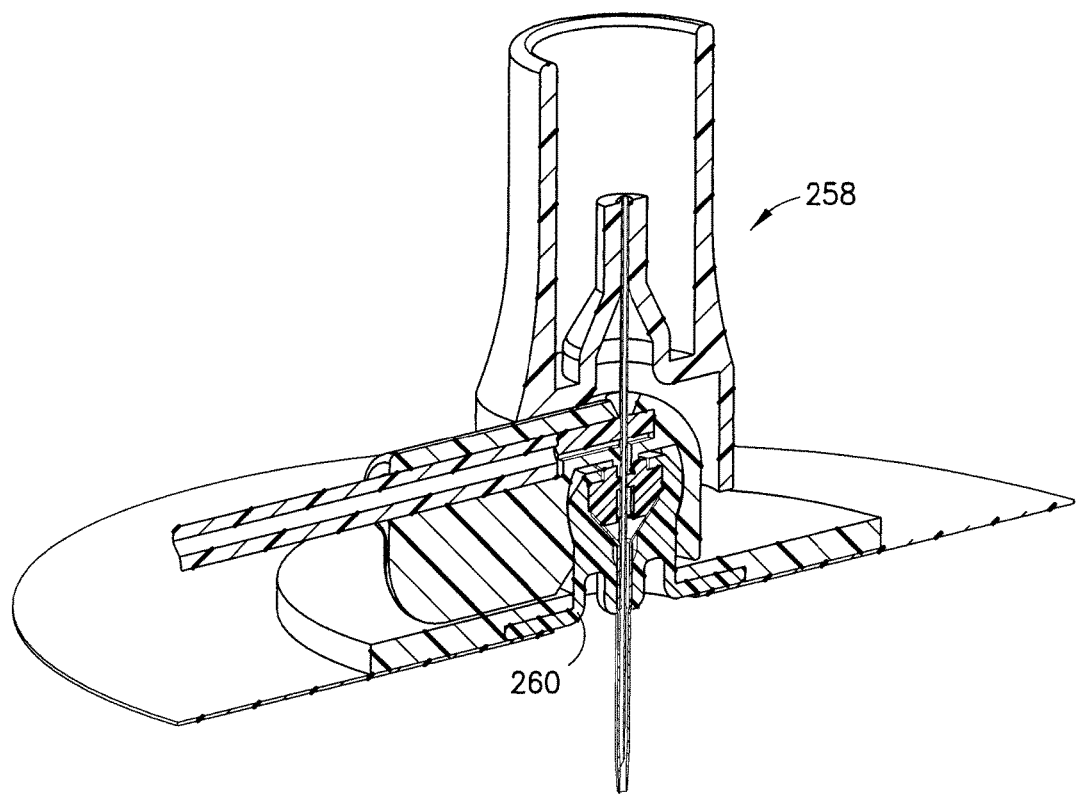
FIG. 55 is a perspective cross-sectional view of and introducer needle, a fluid connector, and a base fully engaged with each other in accordance with an exemplary embodiment of the present invention.
Figure 56:
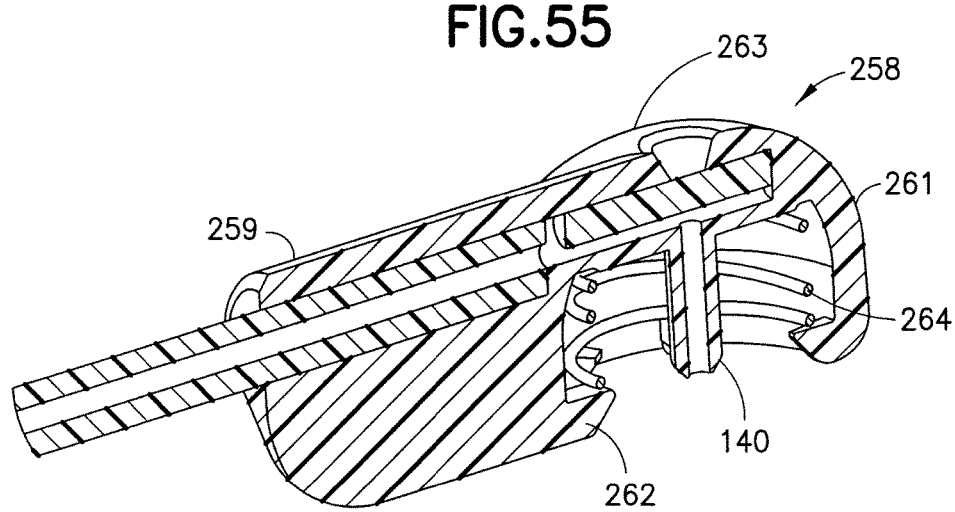
FIG. 56 is a perspective cross-sectional view of the fluid connector of FIG. 55.
Figure 57:
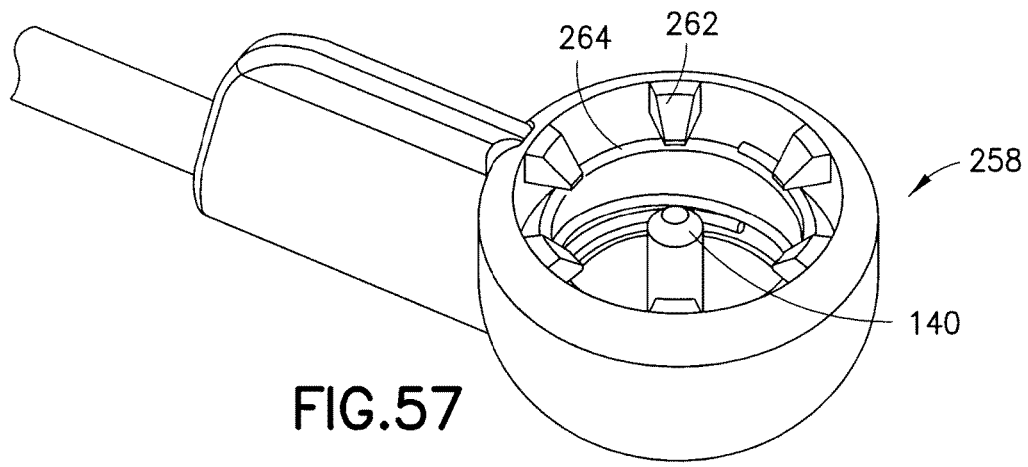
FIG. 57 is a bottom perspective view of the fluid connector of FIG. 55.

FIGS. 55-59 depict a locking fluid connector 258 that a user may place in, for example, six different rotational positions. FIG. 55 is a cross-sectional view of the locking fluid connector 258 and includes a base 260 that the locking fluid connector 258 locks onto. The fluid connector 258 includes a tubing portion 259 with a tubing port for connecting tubing thereto, and a hub portion 261 for connection with the base 260. The hub portion 261 has a domed portion 263. FIG. 56 is a cross-sectional view of the locking fluid connector 258 and includes engagement fingers 262 protruding radially inward at the distal opening of the domed portion. The molded cannula 140 extends from the domed portion and is in fluid communication with the tubing port. The engagement fingers 262 fix a tensile element such as, for example, a spring 264 within the locking fluid connector 258. The spring 264 in FIG. 56 may be biased or, alternatively, may be unbiased when the locking fluid connector 258 is not connected to the base 260. FIG. 57 is a bottom perspective view of the locking fluid connector 258 that illustrates that the spring 264 and the fingers are separate.

Figure 58:
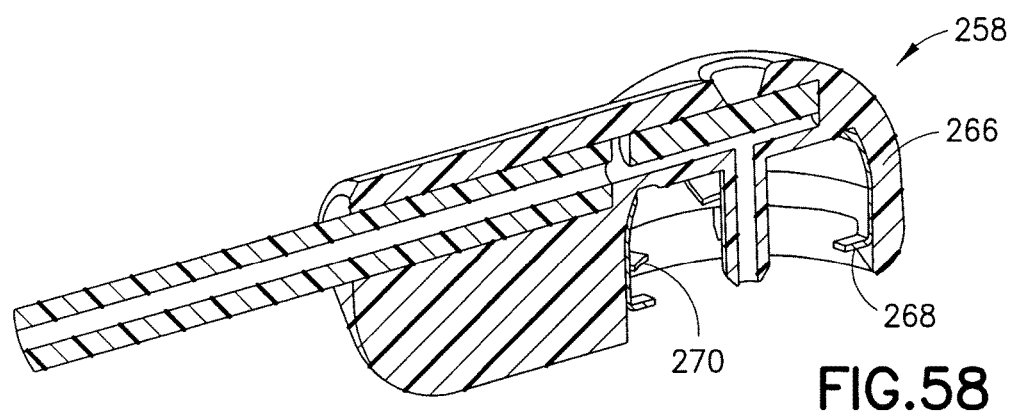
FIG. 58 is a perspective cross-sectional view of an alternative exemplary fluid connector of FIG. 55.
Figure 59:
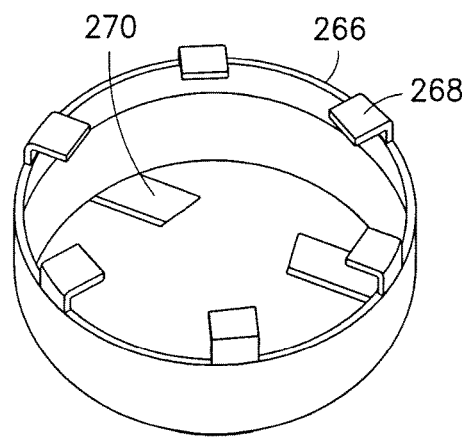
FIG. 59 is a connector disposed in the fluid connector hub of FIG. 58.
Figure 60:
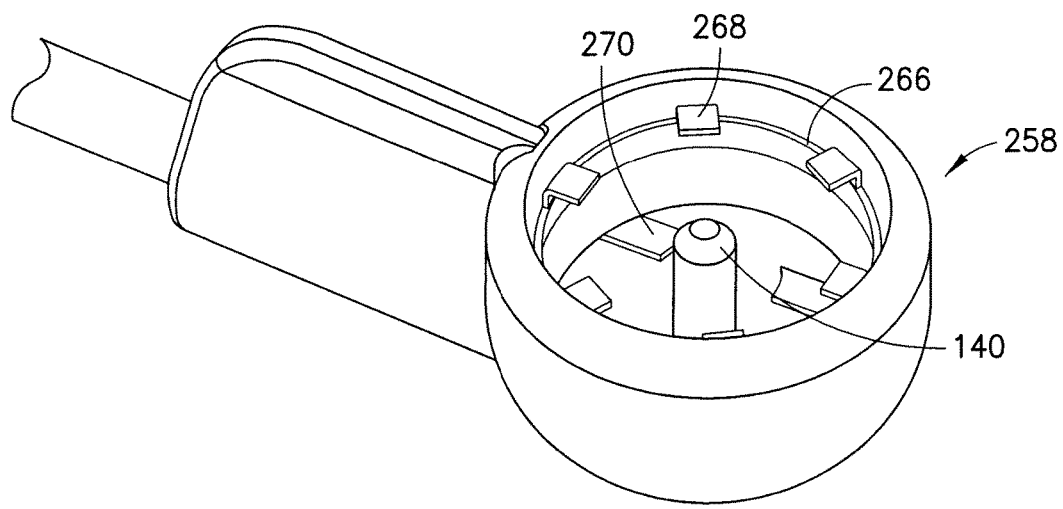
FIG. 60 is a bottom perspective view of the fluid connector of FIG. 58.

FIGS. 58-60 illustrate an alternative exemplary embodiment of the locking fluid connector 258. FIG. 58 is a cross-sectional view of the locking fluid connector 258 and illustrates that a connector 266 is disposed in the locking fluid connector 258. FIG. 59 illustrates that the connector 266 has fingers 268 and a leaf spring 270 integral therewith, in other words. In other words, in the embodiment of FIG. 59, the fingers and spring are integrally formed as one body. FIG. 60 is a bottom view of the locking fluid connector 258 with the connector 266 placed therein and illustrates that the leaf springs 270 are not biased when the locking fluid connector 258 is not connected to the base 260.

Figure 61:
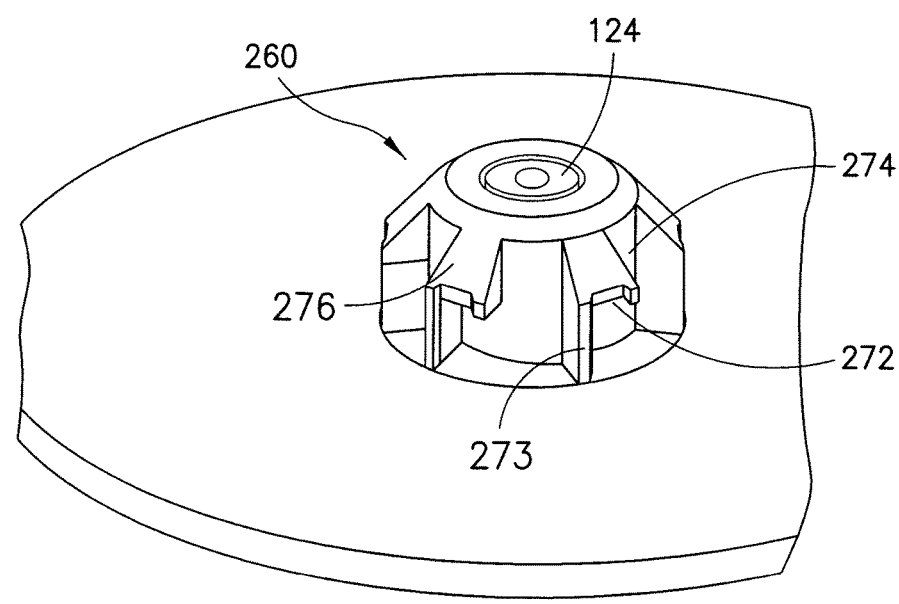
FIG. 61 is a perspective view of the base of FIG. 55.

FIG. 61 depicts the base 260 in more detail. The base 260 has a column that includes inverted J-shaped engagement structures or protrusions 273 having cantilevered ends and tapered edges that protrude in the radial direction from the column. The protrusions 273 include a notch to form engagement pockets 272 and are separated by slots 274. In the exemplary embodiment, the engagement pockets 272 and the slots 274 are configured to receive the engagement fingers of the locking fluid hub retention set 258 and lock it into a predetermined number of discrete rotational orientations (e.g., 6, 8, etc.).

Figure 62:
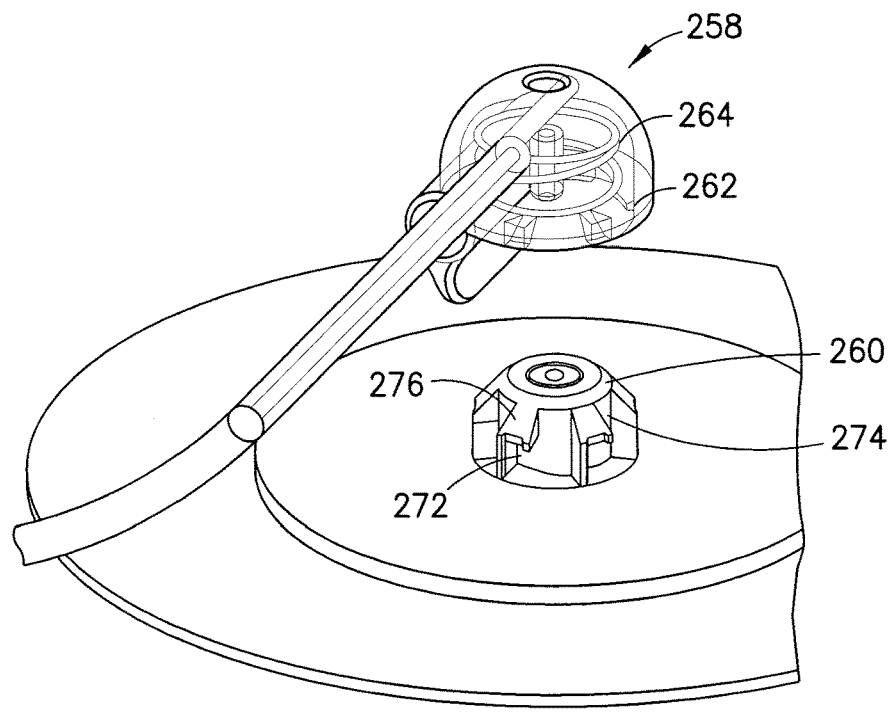
FIG. 62 is a perspective view illustrating the fluid connector of FIG. 55 ready to engage the base of FIG. 61.

FIG. 62 illustrates that, in the event that the engagement fingers 262 of the locking fluid connector 258 are aligned and placed into the slots 274, the spring 264 is in contact with a tapered top surface 276 of the base 260. A user then applies a force to bias the spring 264, causing the engagement fingers 262 to travel into the slots 274. The user then rotates locking fluid connector 258 and releases it, thereby allowing the spring 264 to partially unbias and move the engagement fingers 262 to move into contact with the base 260 via the engagement pockets 272. In this configuration, the locking fluid connector 258 is locked into base 260 via the engagement pockets 272 and can only be removed by pressing on the locking fluid connector 258, rotating it to align the engagement fingers 262 with the slots 274, and releasing the locking fluid connector 258.

The exemplary embodiment provides a locking retention fluid set 268 that can be easily removed and provides a fixed number of rotational positions to allow the user to select the best position of the extension tubing 134. The base 260 may also be made of a rigid or flexible material via a die-cut process, molding process, or a two-step molding process. Various shapes of shrouds may also be used to contour and minimize the potential to snag on objects (e.g., clothing, furniture, etc.) and optimized for ease of handling and intuitive use.

Figure 63:
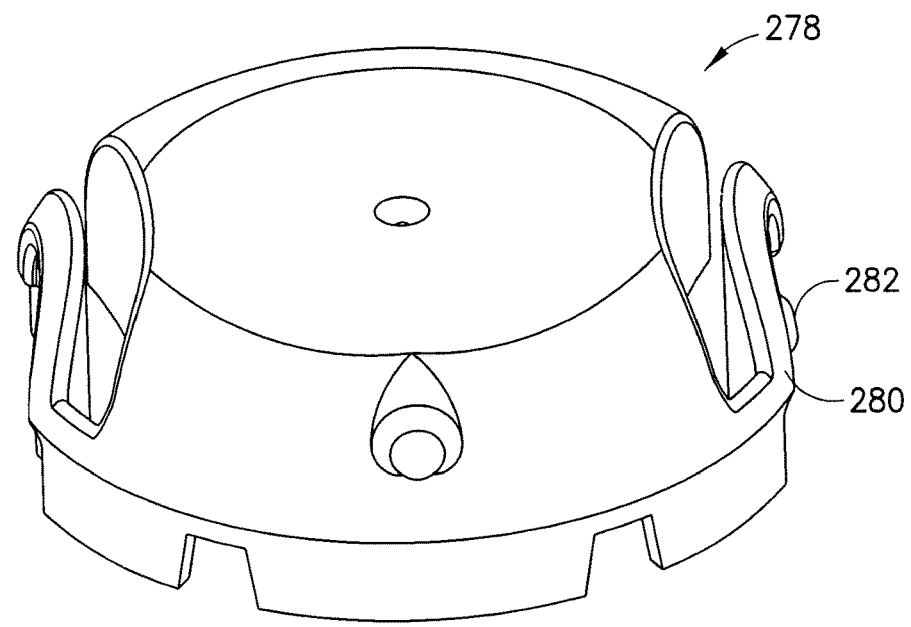
FIG. 63 is a perspective view of another exemplary fluid connector in accordance with an exemplary embodiment of the present invention.
Figure 64:
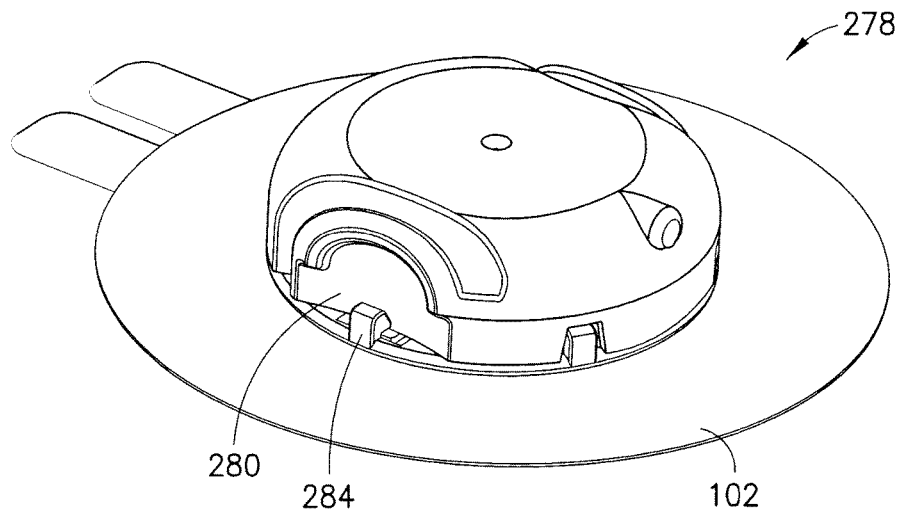
FIG. 64 is a perspective view of the fluid connector of FIG. 63 engaged with a base in accordance with an exemplary embodiment of the present invention.
Figure 65:
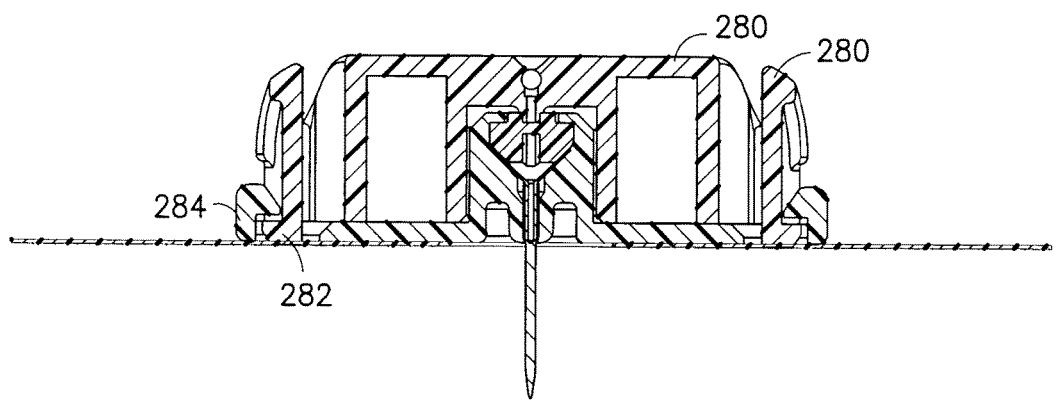
FIG. 65 is a cross-sectional view of the fluid connector and base of FIG. 64.

FIG. 63 illustrates another exemplary embodiment of a locking fluid connector 278 having levers 280 with a latch 282 integral thereto. FIG. 64 illustrates the locking fluid connector 278 fully engaged with the base 102, and ready for placement on the skin. The locking fluid connector 278 is locked into a substantially fixed position via a predetermined number of catches 284 disposed on the surface of the base 102. FIG. 65 illustrates a cross-sectional view of the locking fluid connector 278 and depicts one example of a latch 282 engaged with a catch 284.

Figure 66:
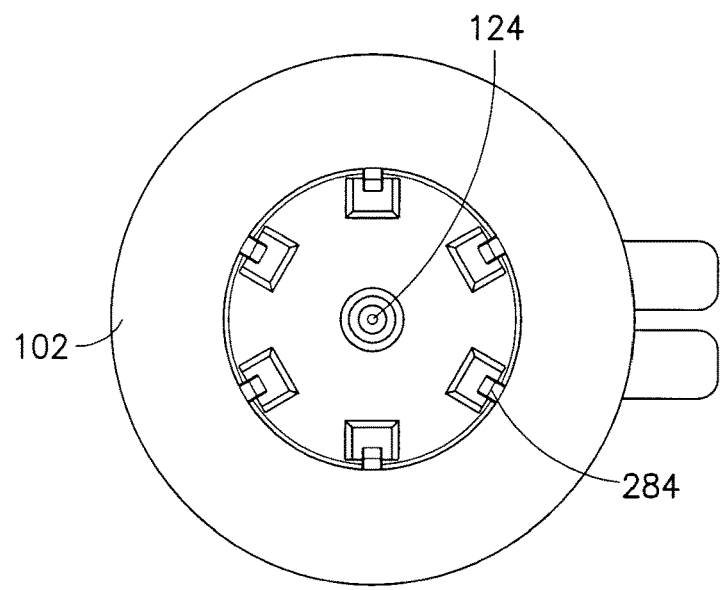
FIG. 66 is a top view of the base of FIG. 64.

FIG. 66 illustrates a base 102 having six different catches 284 to allow a user to place the locking fluid connector 278 in six different rotational positions. To remove the locking fluid connector 278, the user squeezes the levers 280 together to cause the latches 282 to disengage from the catches 284. The user then rotates the locking fluid connector 278 such that the latches 282 are not aligned with the catches 284 and releases the levers 280 and lifts off the locking fluid connector 278. In an alternative embodiment, the levers 280 can displace sufficiently to disengage the latches 282 from the catches 284 to permit the user to simply lift the fluid connector 278 from the base 102 without rotation.

Figure 67:
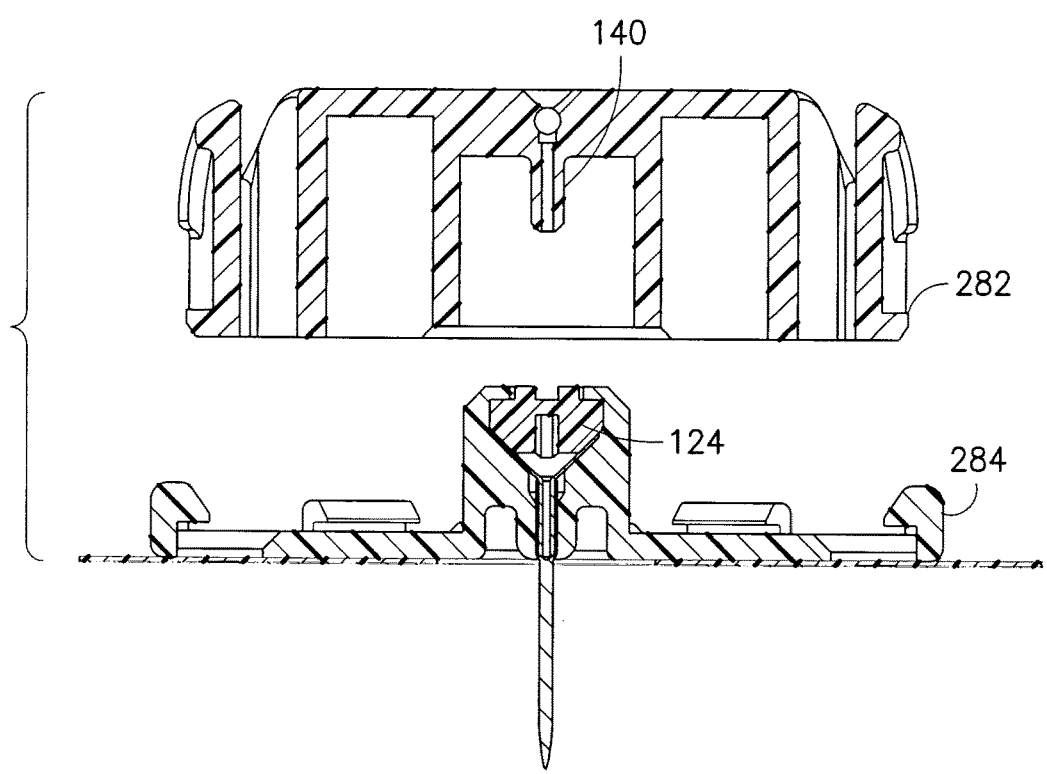
FIG. 67 is a cross-sectional view of the fluid connector and base of FIG. 63.

. The levers 280 are sufficiently displaceable that, if correctly aligned, the fluid connector 278 can be axially lowered onto the base 102 and the latches 282 can snap into engagement with the catches. As shown in FIG. 67 the blunt cannula 140 must be axially aligned with the septum 124 so that the latches 282 can be placed into the catch 284 to place the locking fluid connector 278 into a fixed position.

In an alternative embodiment, to lock the locking fluid connector 278, the user places the latches 282 such that they are not aligned with the catches 284, and then rotates the locking fluid connector 278 until at least one of the latches 282 engage with at least one of the catches 284

The squeeze action of the locking fluid connector 278 is more user friendly and intuitive compared to depressing a single button. Further, the release mechanism is more reliable because it requires fewer assembly tolerances.

Figure 68:
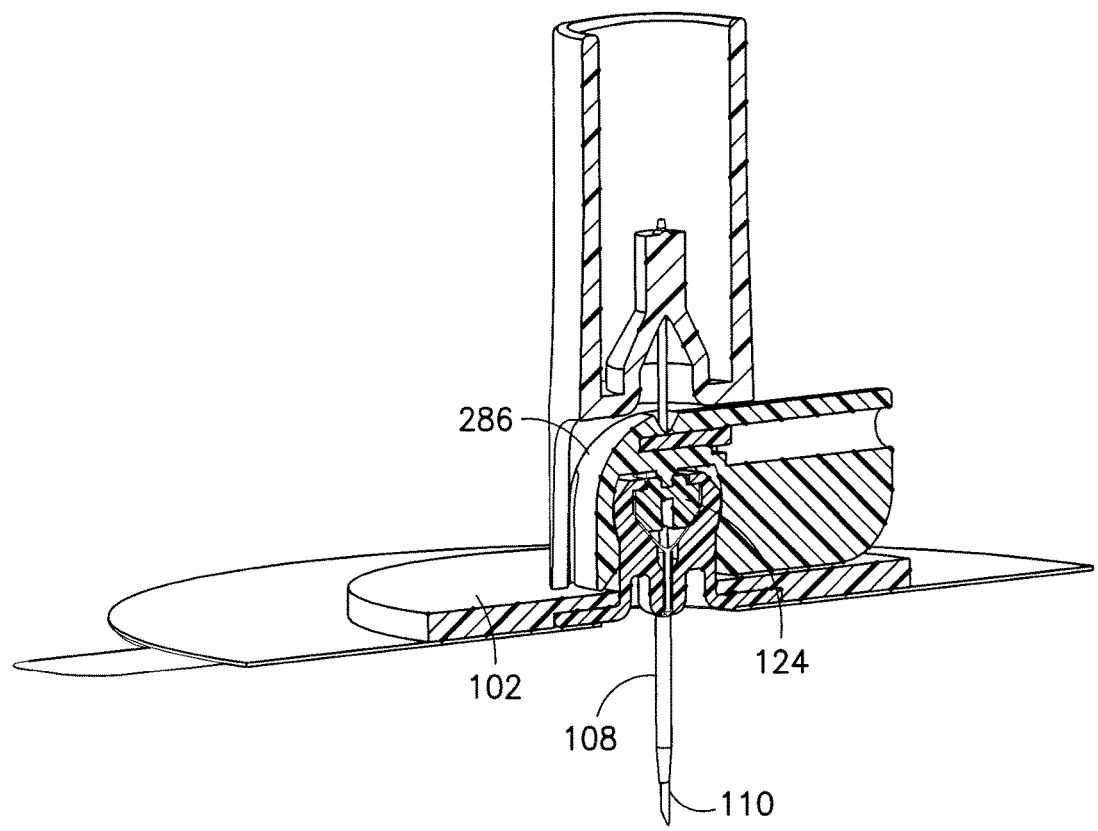
FIG. 68 is a perspective cross-sectional view of a fluid connector in accordance with an exemplary embodiment of the present invention.
Figure 69:
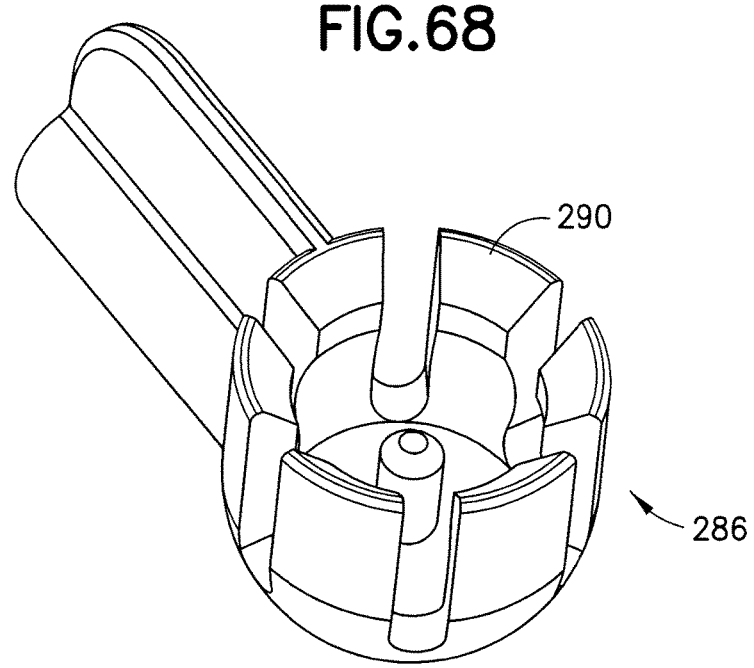
FIG. 69 is a bottom perspective view of the fluid connector of FIG. 68.
Figure 70:
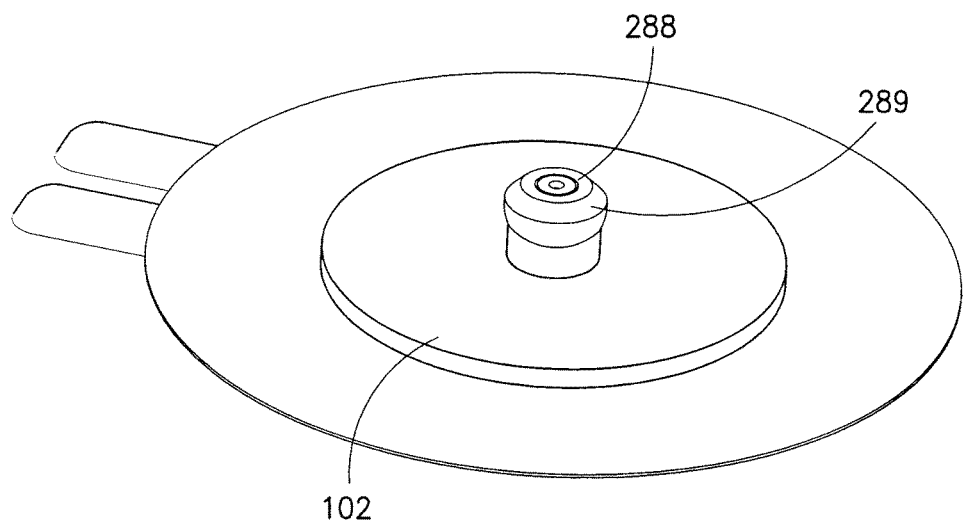
FIG. 70 is a perspective view of an exemplary base for engagement with the fluid connector of FIG. 68.

FIG. 68 is a cross-sectional view of exemplary embodiment of a fluid connector 286 fully engaged with the base 102, piercing the septum 124 and catheter 108 with the introducer needle 110 and ready for placement on the skin. FIG. 69 depicts the bottom of the fluid connector 286 and FIG. 70 illustrates a base latch 288 that the fluid connector 286 connects to. The fluid connector 286 includes at least one snap latch 290 having an angular profile to snap over the base latch 288. For example, FIG. 70 illustrates a spherically shaped post or ball 289 on the base latch 288 to receive the snap latches 290. The snap latches 290 are configured to unlatch from the ball 289 in the event that the fluid connector 286 experiences undesired force that would normally remove the catheter from the user. That is, the fluid connector 286 is designed to separate from the base 102 to prevent inadvertent removal of the catheter from the user's body in the event that, for example, the extension tubing 134 is accidentally pulled by an external object (e.g., a doorknob, furniture, etc.).

Figure 71:
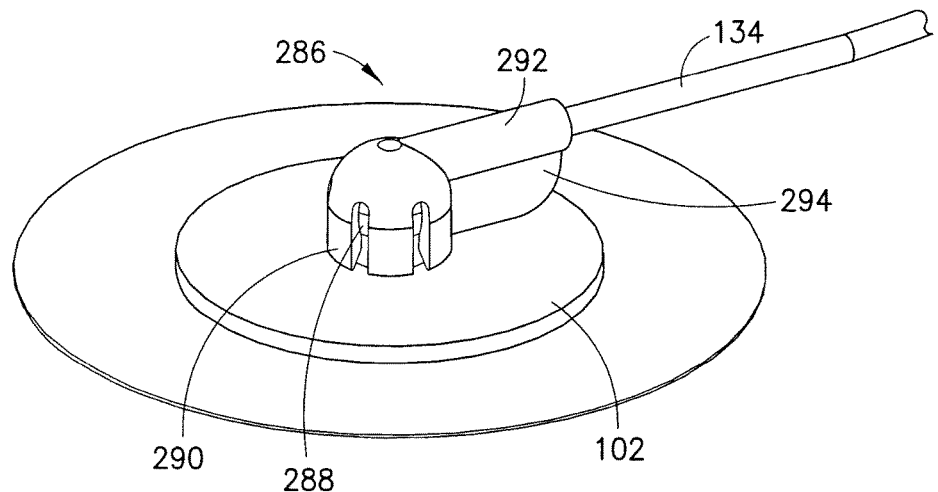
FIG. 71 is a perspective view of the fluid connector of FIG. 68 engaged with the base of FIG. 70.

FIG. 71 illustrates the fluid connector 286 connected to the base latch 288 and is able to rotate 360 degrees around the base latch 288, which may be partially exposed between the snap latches 290. The fluid connector 286 includes a sheath 292 that receives the extension tubing 134 and has a sheath base 294 that extends along the sheath 292. The sheath base 294 protrudes from the bottom surface of the sheath 292 toward the base 102. In the embodiment of FIG. 71, the sheath 292 and the sheath base 294 generally do not extend beyond the radius of the base 102. The sheath base 294 provides support to prevent the fluid connector 286 from unlatching in the event an undesired force is asserted on the sheath 292 or extension tubing 134.

Figure 72:
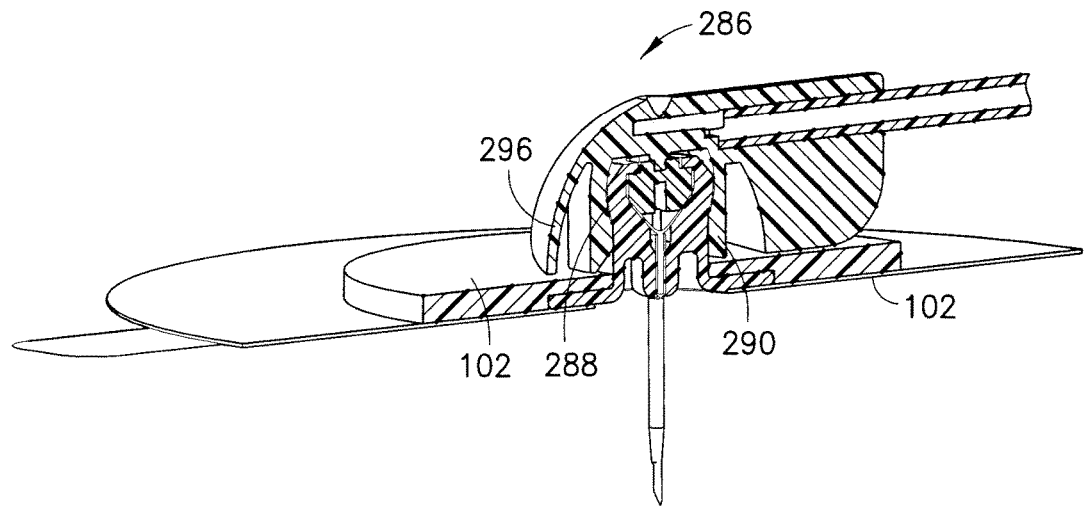
FIG. 72 is a perspective cross-sectional view of another exemplary fluid connector with a shroud in accordance with an embodiment of the present invention.
Figure 73:
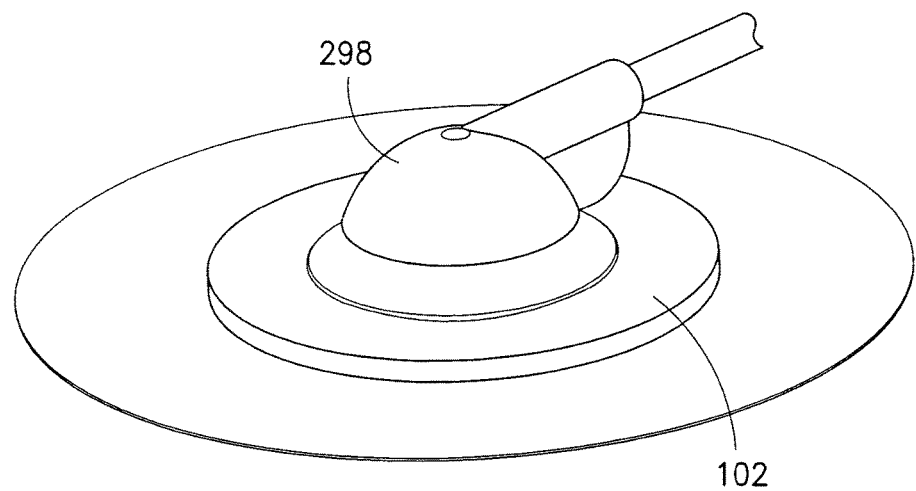
FIGS. 73 and 74 are additional exemplary embodiments of the fluid connector of FIG. 72.

FIG. 72 is a cross-sectional view that illustrates another exemplary embodiment of the fluid connector 286 having a shroud 296 with a hemispherical dome shape that extends over and substantially encloses the snap fingers 290. In FIG. 72, the radius of the shroud 296 is less than the radius of the base 102. FIG. 73 illustrates an exemplary embodiment of a tapered shroud 298 that tapers the edges to be substantially planar with the surface of the base 102. The purpose of the shroud 296 is to prevent the user from squeezing the snap latches 290 during removal, which would make it difficult to remove the fluid connector 286 from the base 102. Also, the low profile of the shroud 296 minimizes the potential for unintentionally snagging the fluid connector 286 on clothing or objects.

Figure 74:
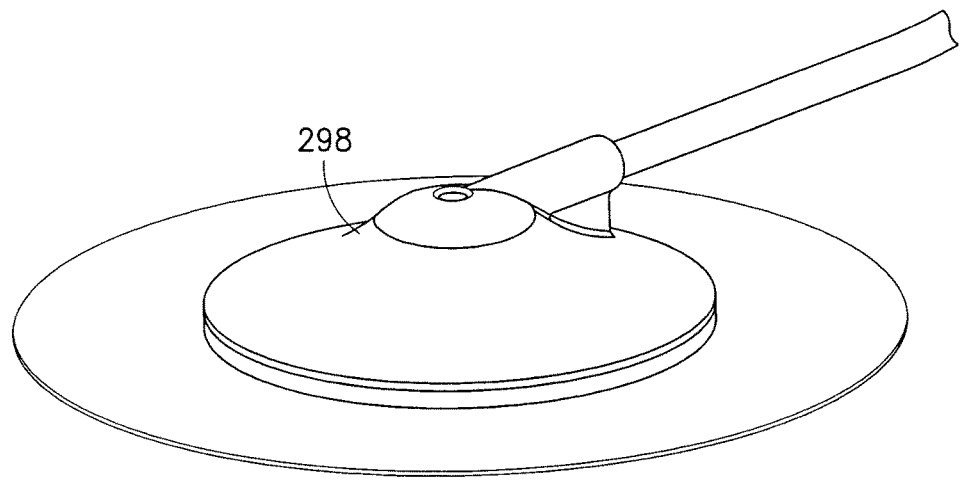

FIG. 74 illustrates another exemplary embodiment of a tapered shroud 298 with tapered edges that are substantially planar with the surface of the base 102. The tapered shroud 298 impedes accidental disengagement of fluid connector 286 from the user. In another exemplary embodiment of the fluid connector 286 illustrated in FIG. 73, the radius of the tapered shroud 298 is substantially equal to the radius of the base 102. In other embodiments, the shape of the tapered shroud 298 may be modified in any suitable manner for aesthetic purposes or to enhance the user's grip on the fluid connector 286.

The exemplary embodiment provides a fluid connector that separates from the user's body prior to removal of the catheter in the event that the fluid connector experiences an undesired external force. Further, the above-described example provides a shroud with a tapered edge that is substantially planar with the user's skin to facilitate engagement and impede accidental disengagement of the fluid retention set. The exemplary embodiment also includes a sheath with a base to prevent inadvertent removal of the fluid connector from the base 102 due to an undesired force experienced by the extension tubing.

Figure 75:
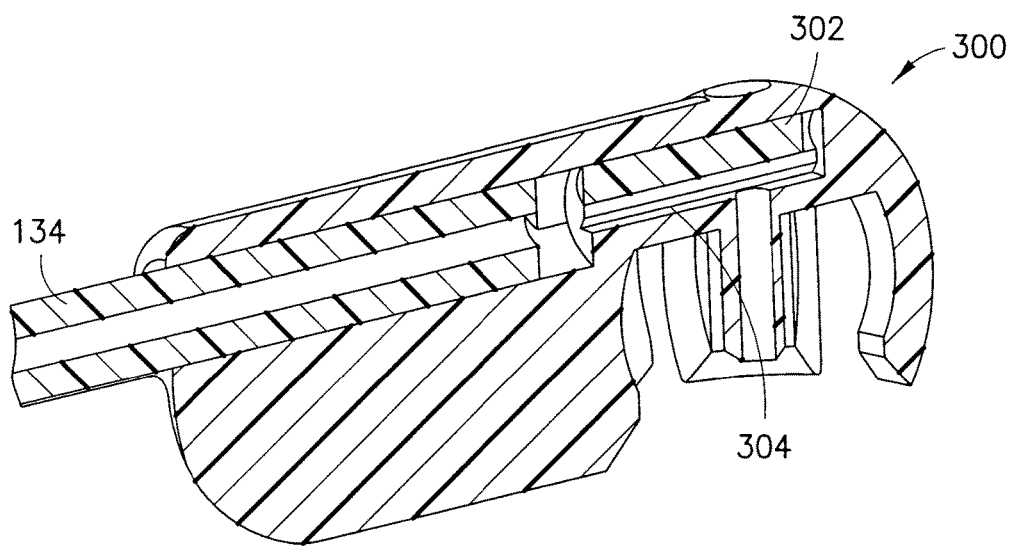
FIG. 75 is a sectional view of another exemplary fluid connector in accordance with an exemplary embodiment of the present invention.

FIG. 75 illustrates another exemplary embodiment of a fluid connector 300 having a septum 302 disposed therein to allow priming of an introducer needle (not shown) disposed in the fluid connector 300 before insertion. The septum 302 is cylindrical in shape and is placed in the axial direction of the extension set tubing 134 such that a fluid path 304 is formed below the septum 302. In this exemplary embodiment, the introducer needle is configured to receive the fluid so that the fluid connector 300 may be primed prior to insertion of the introducer needle.

Alternatively, the septum 302 can be the tubing 134, so long as the tubing material possesses sufficient healing (sealing) properties to prevent leakage due to the slit caused by the introducer needle 110, while still having suitable material properties to perform the other functions required of the tubing 134.

Figure 76:
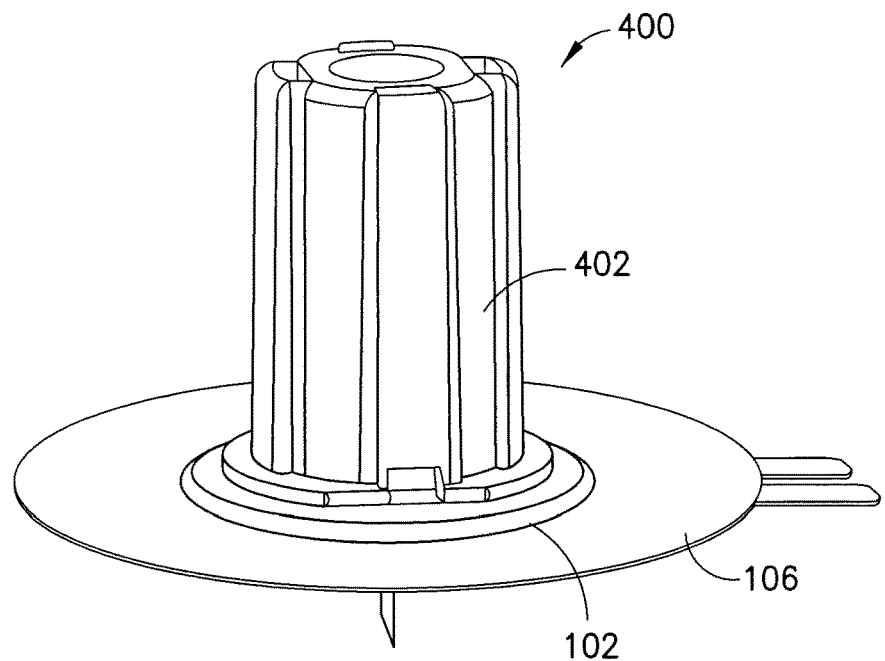
FIGS. 76 and 83 are perspective views of a needle shield device in accordance with an exemplary embodiment of the present invention.
Figure 77:
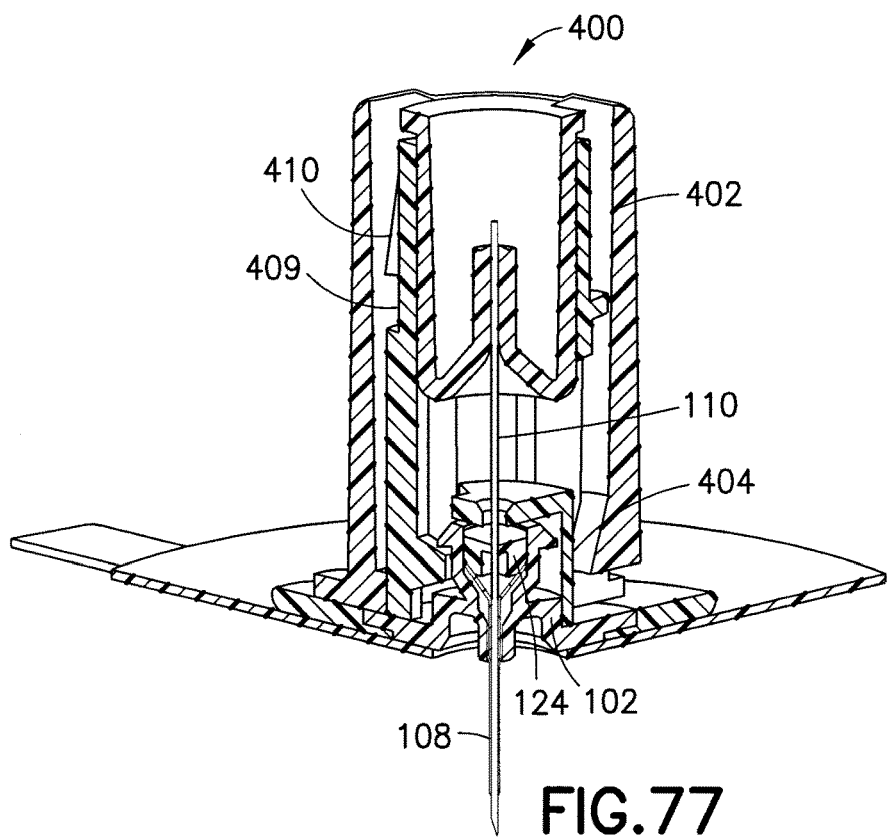
FIGS. 77-82 are perspective cross-sectional views illustrating operation of the needle shield device of FIG. 76.

FIG. 76 illustrates a passive needle shield device 400 connected to the base 102 and ready for placement on the skin. FIG. 77 is a cross-sectional view of the needle shield device 400 fully engaged with the base 102, piercing the septum 124 and the catheter 108 with the introducer needle 110. The needle shield device 400 includes a shield needle hub or outer shield 402 which surrounds and encloses an inner shield 404 and the introducer needle 110.

FIGS. 78-81 illustrate the sequence of steps that occur after the user has inserted the catheter 108. In other words, these figures illustrate the operation of removing the needle shield device 400 from the base 102. Briefly, the user simply pulls on the outer shield 402 in a direction away from the base 102 to remove the introducer needle 110. According to one embodiment, the outer shield 402 and inner shield 404 are both made of rigid plastic materials that have some degree of flexibility.

Figure 78:
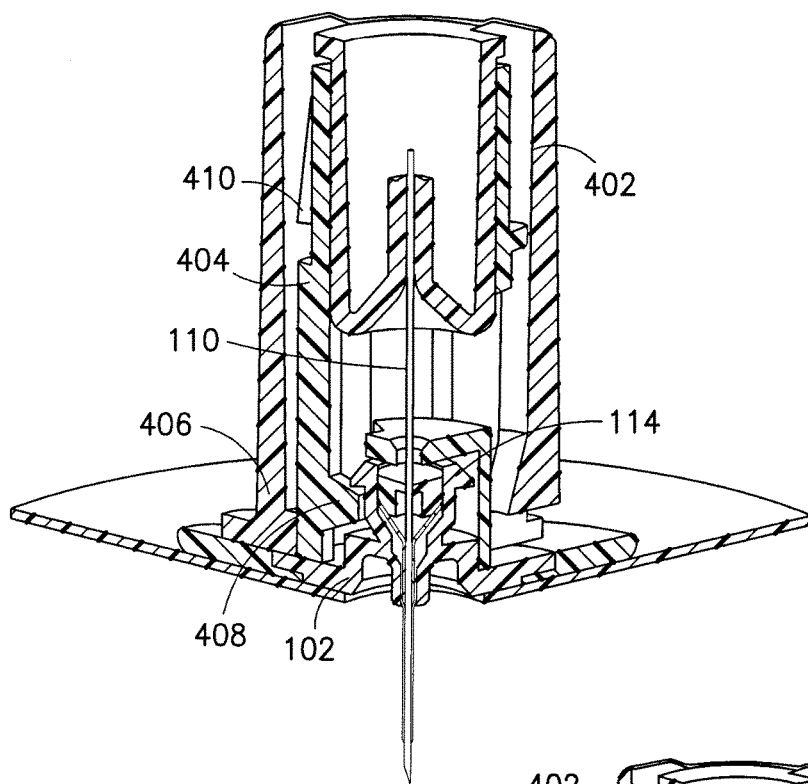

In more detail, FIG. 78 is a quarter-sectional view illustrating an initial state of the needle shield device 400 and a first position of the outer shield 402 relative to the inner shield 404, in which an outer shield hub latch 406 contacts the base 102 and also contacts a cantilevered latch beam 408 of the inner shield 400 to maintain engagement of the latch beam 408 with the base 102 beneath the base latch 114. According to one embodiment, the hub latch 406 biases the latch beam 408 radially inward.

Figure 79:
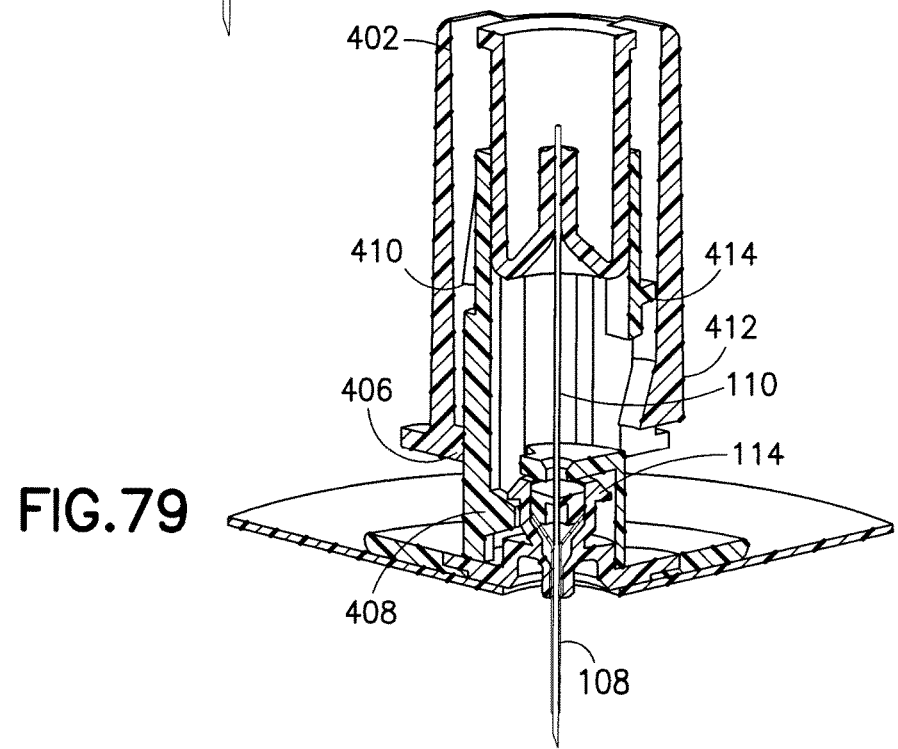

FIG. 79 illustrates the orientation of the needle shield device 400 while the user is axially displacing the outer shield 402, but before it has completed its stroke relative to the inner shield 404. In this state, the outer shield 402 continues to prevent the latch beam 408 from disengaging from the base 102. More specifically it is the hub latch 406 that holds the latch beam 408 in place against the base 102. Therefore, according to one embodiment, the inner shield 404 is locked onto the base 102 while the outer shield 402 is being axially displaced relative to the inner shield 404.

Figure 80:
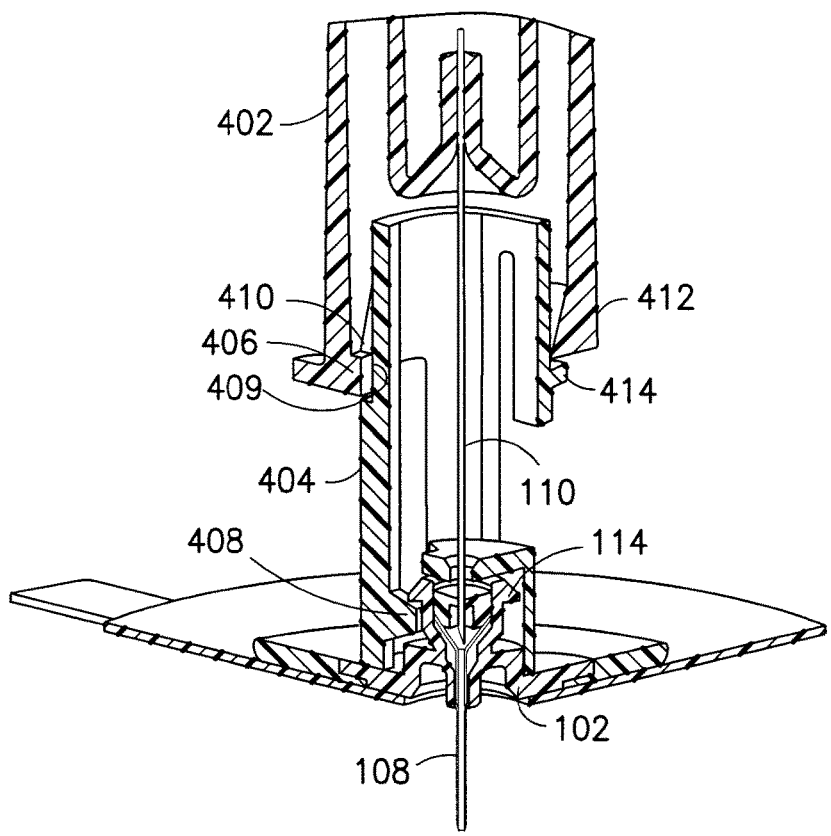

FIG. 80 illustrates the completely displaced position of the outer shield 402 with respect to the inner shield 404. In this state, the hub latch 406 no longer prevents the latch beam 408 from disengaging from the base 102. The hub latch 406 is instead disposed in an indent 409 (best shown in FIG. 77) on the inner shield 404 and engaged with a shield latch 410 formed on the inner shield 404. The shield latch 410 engages a top side of the hub latch 406, thereby preventing further proximal displacement of the outer shield 402 relative to the inner shield 404. Additionally, because the hub latch 406 is no longer pressing on the latch beam 408, the latch beam 408 can disengage from the base 102.

Further, a hub beam or outer shield latch 412 rides over an inner shield latch 414 and the bottom of the hub beam 412 engages the top of the inner shield latch 414 to prevent distal displacement of the outer shield 402 relative to the inner shield 404. According to one embodiment, the hub beam 412 is cantilevered.

The latch beam 408 is free to radially displace and disengage from the base 102 once the user continues to distally displace the needle shield device 400. The engagement of the shield latch 410 with the hub latch 406 and the engagement of the hub beam 412 with the inner shield latch 414 shields the introducer needle 110 and thereby reduces the possibility of an accidental needle stick.

According to one embodiment, the inner shield latch 414 is fixedly disposed on the inner shield 404. According to another embodiment, the inner shield latch 414 is disposed on a cantilevered inner shield latch beam 416 so that both the inner shield latch beam 416 and the hub beam 412 are cantilevered. According to yet another embodiment, the inner shield latch 414 is disposed on a cantilevered inner shield latch beam 416 and the hub beam is fixedly disposed on the outer shield 402.

In another alternative embodiment, the needle shield device 400 can also be attached to a fluid connector 126 and the base 102. Such an embodiment allows a user to prime the infusion set while it is outside the body and insert and remove the introducer needle 110 with the fluid connector 126 attached the entire time.

Figure 81:
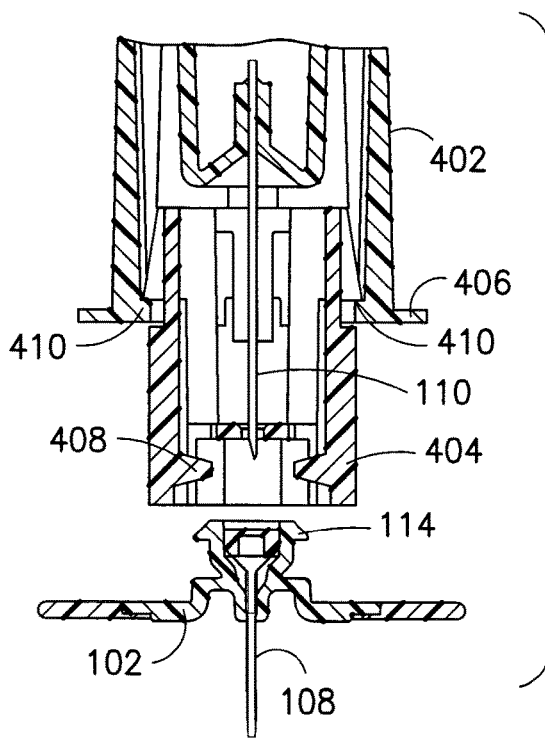
Figure 82:
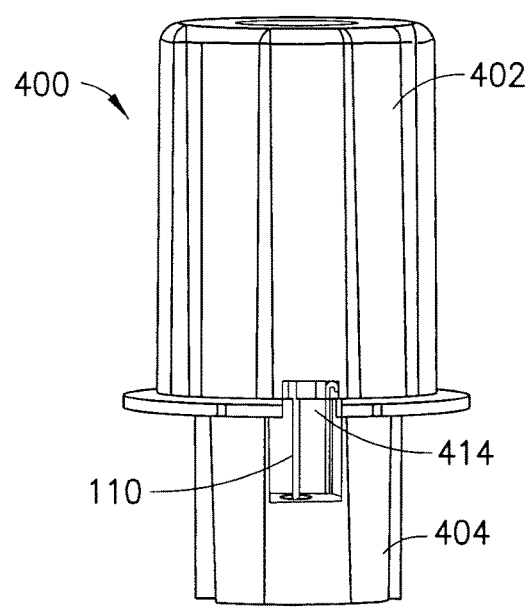

FIG. 81 illustrates a completely deployed needle shield device 400. The latch beam 408 is removed from the base 102 as the user continues to pull on the outer shield 402. FIG. 82 is a perspective view illustrating the needle shield 400 in the completely deployed state, removed from the base 102 and ready for disposal.

Figure 83:
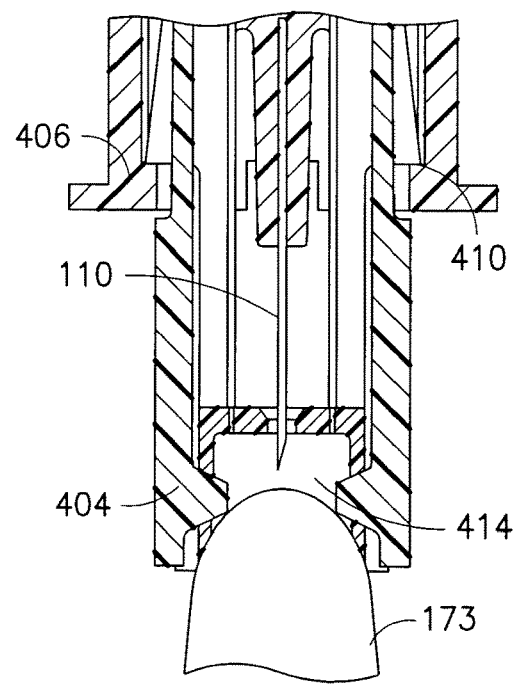

FIG. 83 illustrates how the introducer needle 110 within the needle shield device 400 is prevented from contacting a user's finger 173 during handling of the completely deployed needle shield device 400. The inner shield 404 forms a shield well 414 surrounding the exposed introducer needle 110 such that an average finger 173 will not fit through the shield well 414 opening and contact the exposed introducer needle 110.

In each of the herein disclosed embodiments and in other alternative embodiments, the components of the infusion set can be made of injection-molded polypropylene, polyethylene, polyesters, acrylonitrile-butadiene-styrene polymers, and/or bio-based resins such as polylactide, starch-filled polypropylene, or polyhydroxyalkanoates. The catheter can be a separate component or injection-molded as part of the base assembly, either as a single part or as a coinjection-molded part using two resins.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the appended claims and their equivalents.

What is claimed is:

1. An infusion set, comprising:
 a base, comprising:
  a base portion having a column extending proximally therefrom, the column having a plurality of inverted J-shaped engagement structures with cantilevered ends, the engagement structures forming engagement pockets therein and being circumferentially arrayed around the column and separated by a plurality of slots;
  a septum disposed within the column; and
  a cannula protruding distally from the base portion and being in fluid communication with a distal side of the septum; and
 a locking fluid connector, comprising:
  a tubing portion having a tubing port for connecting tubing thereto; and
  a hub portion for connecting with the base, the hub portion comprising:
   a domed portion;
   a blunt cannula for penetrating the septum, the blunt cannula extending from the domed portion and being fluidly connected with the tubing port;
   a plurality of engagement fingers protruding radially inward; and
   a spring element held within the domed portion by the engagement fingers;
 wherein:
 the engagement fingers are alignable with the aligning the slots;
 the locking fluid connector is displaceable toward the base when the blunt cannula is aligned with the septum and the engagement fingers are aligned with the slots, thereby compressing the spring element;
 the locking fluid connector is rotatable about the column once the engagement fingers have distally cleared the cantilevered ends of the engagement structures; and
 the locking fluid is displaceable away from the base under the force of the spring element with the engagement fingers disposed within the engagement pockets to lock the fluid connector to the base in one of a plurality of discrete circumferential orientations.

2. The infusion set according to claim 1, wherein:
 the hub portion has an introducer opening on a proximal portion of the hub portion for receiving an introducer needle, the introducer opening being in fluid communication with the blunt cannula; and an introducer septum disposed between the introducer opening and the blunt cannula to maintain the sterility of the blunt cannula fluid path.

3. The infusion set according to claim 1, wherein the engagement fingers and the spring element are formed as a unitary structure that is retainable within the domed portion.

4. An infusion set, comprising:
 a base, comprising:
  a base portion having a column extending proximally therefrom, the column having a ball-shaped base latch at its proximal end;
  septum disposed within the column; and
  a cannula protruding distally from the base portion and being in fluid communication with a distal side of the septum; and
 a fluid connector, comprising:
  a tubing portion having a tubing port for connecting tubing thereto; and
  a hub portion for connecting with the base, the hub portion comprising:
   a domed portion;
   a blunt cannula for penetrating the septum, the blunt cannula extending from the domed portion and being fluidly connected with the tubing port; and
   a plurality of distally cantilevered snap latches, each having an internal angular profile to snap over the base latch to connect the fluid connector with the base.

5. The infusion set according to claim 4, further comprising a sheath base extending distally from the tubing portion and radially from the domed portion, the sheath base providing support against the base to prevent the fluid connector from rocking on the base and unlatching from the base.

6. The infusion set according to claim 4, further comprising a shroud substantially enclosing the snap latches to prevent a user from squeezing the snap latches during removal of the fluid connector from the base.

* * * * *

UNITED STATES PATENT AND TRADEMARK OFFICE
CERTIFICATE OF CORRECTION

PATENT NO. : 10,112,006 B2
APPLICATION NO. : 15/445766
DATED : October 30, 2018
INVENTOR(S) : Ralph Sonderegger et al.

Page 1 of 1

It is certified that error appears in the above-identified patent and that said Letters Patent is hereby corrected as shown below:

In the Claims

Column 20, Line 58, after "fluid" insert -- connector --.

Signed and Sealed this
Twenty-sixth Day of February, 2019

Andrei Iancu
*Director of the United States Patent and Trademark Office*